(12) United States Patent
Binder

(10) Patent No.: US 8,183,030 B2
(45) Date of Patent: May 22, 2012

(54) USE OF CELL SURFACE DISPLAYS IN YEAST CELL CATALYST SUPPORTS

(75) Inventor: Thomas P. Binder, Decatur, IL (US)

(73) Assignee: Archer Daniels Midland Company, Decatur, IL (US)

(*) Notice: Subject to any disclaimer, the term of this patent is extended or adjusted under 35 U.S.C. 154(b) by 137 days.

(21) Appl. No.: 11/974,097

(22) Filed: Oct. 11, 2007

(65) Prior Publication Data

US 2008/0090282 A1    Apr. 17, 2008

Related U.S. Application Data

(60) Provisional application No. 60/851,434, filed on Oct. 13, 2006.

(51) Int. Cl.
*C12N 1/00* (2006.01)
*C12N 7/00* (2006.01)

(52) U.S. Cl. ............. 435/254.21; 435/254.2; 435/254.1; 435/243; 530/350; 546/210

(58) Field of Classification Search ............. 435/254.21, 435/254.2, 254.1, 243; 530/350; 546/210
See application file for complete search history.

(56) References Cited

U.S. PATENT DOCUMENTS

| | | | |
|---|---|---|---|
| 5,637,508 A | 6/1997 | Kidwell et al. | |
| 6,300,065 B1 | 10/2001 | Kieke et al. | |
| 6,423,538 B1 | 7/2002 | Wittrup et al. | |
| 6,699,658 B1 | 3/2004 | Wittrup et al. | |
| 7,488,593 B2 | 2/2009 | Belcher et al. | |
| 2004/0077090 A1* | 4/2004 | Short ........................... | 435/471 |
| 2005/0272067 A1 | 12/2005 | Macina et al. | |
| 2006/0003387 A1 | 1/2006 | Peelle et al. | |
| 2006/0009354 A1 | 1/2006 | Yeung et al. | |
| 2006/0246560 A1 | 11/2006 | Fatland-Bloom et al. | |
| 2008/0286750 A1* | 11/2008 | Xu et al. ........................... | 435/4 |
| 2009/0105083 A1* | 4/2009 | Hoogenboom et al. .......... | 506/9 |

FOREIGN PATENT DOCUMENTS

EP    1070537 A2    1/2001

OTHER PUBLICATIONS

Avidin-Biotin: "Chemistry: A Handbook".
Boder et al., "Yeast Surface Display of Nonconvalent MHC Class II Heterodimer Complexed with Antigenic Peptide", Univ. of Pennsylvania, Dept. of Chemical & Biomolecular Engineering, 2005, pp. 1-25.
Boder et al., "Yeast Surface Display for Screening Combinational Polypeptide Libraries", Nature Biotechnology, Jun. 1997, vol. 15, pp. 553-557.
Boder et al., "Yeast Surface Display for Directed Evolution of Protein Expression, Affinity, and Stability", Methods in Enzymology, 2000, vol. 328, pp. 430-444.
Shoseyov et al., "Cellulose Binding Domains—a Novel Fusion Technology for Efficient, Low Cost Purification and Immobiliation of Recombinant Proteins", Innovations Newsletter of Novagen, Inc., Advanced Products and Protocols for Molecular Biology Research, No. 7, Aug. 1997, pp. 1-3.
Interchem Product Flyer FT-UP10685.
Kim et al., "Bacterial Cell Surface Display of an Enzyme Library for Selective Screening of Improved Cellulase Variants", Applied and Environmental Microbiology, vol. 66, No. 2, Feb. 2000, pp. 788-793.
Li, "Applications of Display Technology in Protein Analysis", Nature Biotechnology, Dec. 2000, vol. 18, pp. 1251-1256.
Murai et al., "Construction of a Starch-Utilizing Yeast by Cell Surface Engineering", Applied and Environmental Microbiology, Apr. 2007, vol. 63, No. 4, pp. 1362-1366.
Narita et al., "Display of Active Enzymes on the Cell Surface of *Escherichia coli* Using PgsA Anchor Protein and Their Application to Bioconversion", Applied Genetics and Molecular Biotechnology.
Newman et al., "Gpi19, the *Saccharomyces cerevisiae* Homologue of Mammalian PIG-P, Is a Subunit of the Initial Enzyme for Glycosylphosphatidylinositol Anchor Biosynthesis", Eukaryotic Cell, Nov. 2005, vol. 4, No. 11, pp. 1801-1807.
Shimojyo et al., "Preparation of Yeast Strains Displaying IgG Binding Domain ZZ and Enhanced Green Fluorescent Protein for Novel Antigen Detection Systems", Journal of Bioscience and Bioengineering, 2003, vol. 96, No. 5, pp. 493-495.
Ueda et al., "Cell Surface Engineering of Yeast: Construction of Arming Yeast with Biocatalyst", Journal of Bioscience and Bioengineering, 2000, vol. 90, No. 2, pp. 125-136.
Van Der Vaart et al., "Comparison of Cell Wall Proteins of *Saccharomyces cerevisiae* as Anchors for Cell Surface Expression of Heterologous Proteins", Applied and Environmental Microbiology, Feb. 1997, vol. 63, No. 2, pp. 615-620.
Van Hoek et al., "Effects of Pyruvate Decarboxylase Overproduction on Flux Distribution at the Pyruvate Branch Point in *Saccharomyces cerevisiae*", Applied and Environmental Microbiology, Jun. 1998, vol. 64, No. 6, pp. 2133-2140.
Weaver-Feldhaus et al., "Directed Evolution for the Development of Conformation-Specific Affinity Reagents Using Yeast Display", Protein Engineering, Design & Selection, 2005, vol. 18, No. 11, pp. 527-536.
Zou et al., "Construction of a Combinatorial Protein Library Displayed on Yeast Cell Surface Using DNA Random Priming Method", Journal of Bioscience and Bioengineering, 2001, vol. 92, No. 4., pp. 393-396.
Owsik et al., "Immobilized Cu(II) Ions as the Oxidation Catalysts", Chemia [Zeszty naukowe—Politechnika Slaska chemia], 2001, vol. 146, pp. 113-116.
Kirihara et al., "Aerobic Oxidation Catalyzed by Polymer-Supported Vanadium Compounds", ITE Letters on Batteries, New Technologies & Medicine, 2004, Issue 5, pp. 479-482.
Franot et al., "A Polymer-Bound Oxazaborolidine Catalyst: Enantioselective Borane Reductions of Ketones", Tetrahedron: Asymmetry, 1995, vol. 6, Issue 11, pp. 2755-2766.

(Continued)

*Primary Examiner* — Teresa D. Wessendorf
(74) *Attorney, Agent, or Firm* — Mark W. Roberts

(57) ABSTRACT

Methods and compositions for providing novel catalyst supports are included herein. In one embodiment, included herein are yeast cell supports including one or more receptor proteins uniformly displayed on the surface of a yeast cell having the species *Saccharomyces cerevisiae*. Each receptor protein is anchored to a ligand that is selective for that protein, and each ligand is, in turn, bound to a catalyst. Both the catalyst support-catalyst combinations and the catalyst supports alone are contemplated by the invention.

8 Claims, 15 Drawing Sheets

OTHER PUBLICATIONS

Kang et al., "Catalytic Oxidation of Alcohols with Polymer-Supported Ruthenium Complex under Mild Conditions", Journal of Organometallic Chemistry, 2005, vol. 690, Issue 26, pp. 6309-6313.

Ferreira et al., "Catalytic Oxidation of Alcohols Using Molecular Oxygen Mediated by Poly(Ethyleneglycol)-Supported Nitroxyl Radicals", Applied Catalysis, B: Environmental, 2005, vol. 61, Issue 3-4, pp. 206-211.

Pomogailo et al., "Synthesis and Catalytic Properties of Polymer-Immobilized Noble Metal Clusters", PMSE Preprints, 2005, vol. 93, p. 945-EOA.

Moghadam et al., "A Convenient Preparation of Polymer-Supported Manganese Porphyrin and its Use as Hydrocarbon Mono Oxygenation Catalyst", Journal of Molecular Catalysis A: Chemical, 2004, vol. 217, Issue 1-2, pp. 9-12.

Finashina et al., "Oxidation of Catecholamines on Chitosan-Immobilized Co (II) Salen Complexes", Macromolecular Symposia (IUPAC 10th International Symposium on Macromolecule-Metal Complexes), 2003, vol. 204, pp. 205-217.

Hocke et al., "PS-PEG Resin-Supported Palladium-MOP complexes. Application is Asymmetric Pi-Allylic Reduction", Tetrahedron, 2004, vol. 60, Issue 41, pp. 9297-9306.

Lee et al., "Microbial Cell-Surface Display", Trends in Biotechnology, Jan. 2003, vol. 21, No. 1, pp. 45-52.

Sherman, "Getting Started with Yeast", Methods Enzymol., 2002, vol. 350, pp. 3-41.

Sherman, "An Introduction to the Genetics and Molecular Biology of the Yeast *Saccharomyces cerevisiae*", The Encyclopedia of Molecular Biology and Molecular Medicine, 1997, vol. 6, pp. 302-325.

T7Select System Manual, Novagen, Inc. 2002.

Wernerus et al., "Biotechnological Applications for Surface-Engineered Bacteria", Biotechnol. Appl. Biochem. 2004, vol. 40, pp. 209-228.

Little et al., "Bacterial Surface Presentation of Proteins and Peptides: An Alternative to Phage Technology?", Tibtech, Jan. 1993, vol. 11.

Lashkari et al., "Yeast Microarrays for Genome Wide Parallel Genetic and Gene Expression Analysis", Proc. Natl. Acad. Sci. USA, Nov. 1997, vol. 94, pp. 13057-13062.

Willats et al., "Phage Display: Practicalities and Prospects", Plant Molecular Biology, 2002, vol. 50, pp. 837-854.

Stears et al., "Trends in Microarray Analysis", Nature Medicine, Jan. 2003, vol. 9, No. 1, pp. 140-145.

Zucconi et al., "Selection of Ligands by Panning of Domain Libraries Displayed on Phage Lambda Reveals New Potential Partners of Synaptojanin 1", J. Mol. Biol., 2001, vol. 307, pp. 1329-1339.

Lee et al., "Display of Bacterial Lipase on the *Escherichia coli* Cell Surface by Using FadL as an Anchoring Motif and Use of the Enzyme in Enantioselective Biocatalysts", Applied and Environmental Microbiology, Sep. 2004, vol. 70, No. 9, pp. 5074-5080.

Steidler et al., "Functional Display of a Heterologous Protein on the Surface of *Lactococcus lactis* by Means of the Cell Wall Anchor of *Staphylococcus aureas* Protein A", Applied and Environmental Microbiology, Jan. 1998, vol. 64, No. 1, pp. 342-345.

Breitling et al., "A Surface Expression Vector for Antibody Screening", Gene., 1991, vol. 104, pp. 147-153.

Scott et al., "Searching for Peptide Ligands with an Epitope Library", Science, Jul. 27, 1990, vol. 249, pp. 386-390.

McCafferty et al., "Phage Antibodies: Filamentous Phage Displaying Antibody Variable Domains", Nature, Dec. 6, 1990, vol. 348, pp. 552-554.

Bass et al., "Hormone Phage: An Enrichment Method for Variant Proteins with Altered Binding Properties", Proteins: Strcture, Function, and Genetics, 1990, vol. 8, pp. 309-314.

Smith, "Filamentous Fusion Phage: Novel Expression Vectors That Display Cloned Antigens on the Virion Surface", Science, Jun. 14, 1985, vol. 228, pp. 1315-1317.

International Search Report dated Nov. 19, 2008.

Brown et al., "A Genetic Analysis of Crystal Growth", J. Mol. Biol. (2000), vol. 299, pp. 725-735.

Murai T et al., Development of an arming yeast strain for efficient utilization of starch by co-display of sequential amylolytic enzymes on the cell surface, Applied Microbiology and Biotechnology, Springer Verlag, Berlin, DE, vol. 51, No. 1, Jan. 1, 1999, pp. 65-70.

Shigechi Hisayori et al., Efficient ethanol production from starch through development of novel flocculent yeast strains displaying glucoamylase and co-displaying or secreting alpha-amylase, Journal of Molecular Catalysis. B, Enzymatic, Elsevier, Amsterdam, NL, vol. 17, No. 3-5, Jun. 7, 2002, pp. 179-187.

Thomas CH M et al., Aqueous oxidation of alcohols catalyzed by artificial metalloenzymes based on the biotin-avidin technology, Journal of Organometallic Chemistry, Elsevier-Sequoia S.A. Lausanne, CH, vol. 690, Jan. 1, 2005, pp. 4488-4491.

Collot Jerome et al., Artificial metalloenzymes for enantioselective catalysis based on biotin-avidin, Journal of the American Chemical Society, American Chemical Society, New York, USA, vol. 125, No. 30, Jul. 3, 2003, pp. 9030-9031.

Wilson M E et al., Conversion of a protein to a homogeneous asymmetric hydrogenation catalyst by site specific modification with a di phosphino rhodium i moiety, Journal of the American Chemical Society, American Chemical Society, New York, USA, vol. 100, No. 1, Jan. 4, 1978, pp. 306-307.

Letondor Christophe et al., Artificial metalloenzymes based on biotin-avidin technology for the enantioselective reduction of ketones by transfer hydrogenation, Proceedings of the National Academy of Sciences of USA. (PNAS), National Academy of Science, Washington, DC, US, vol. 102, No. 13, Mar. 29, 2005, pp. 4683-4687.

Ward Thomas R, Artificial metalloenzymes for enantioselective catalysis based on the noncovalent incorporation of organometallic moieties in a host protein, Chemistry—A European Journal, Wiley—V C H Verlag GMBH & Co. KGAA, Weinheim, DE, vol. 11, No. 13, Jun. 20, 2005, pp. 3798-3804.

Kondo A et al., Yeast cell-surface display—applications of molecular display, Applied Microbiology and Biotechnology, Springer Verlag, Berlin, DE, vol. 64, No. 1, Mar. 1, 2004, pp. 28-40.

Ciriminna R et al., Sol-gel entrapped tempo for the selective oxidation of methyl alpha-d-glucopyranoside, Chemical Communications—Chemcom, Royal Society of Chemistry, GB, Jan. 1, 2000.

Anonymous, Amylase, Wikipedia, http://en.wikipedia.org/wiki/Amylase, retrieved from the internet on Mar. 18, 2010.

European Search Report dated May 17, 2010 for EP Application No. 07870778.3-2403 / 2078198 PCT/ US2007/021729.

Avidin-Biotin: "Chemistry: A Handbook", Jan. 1992.

Interchem Product Flyer FT-UP10685, Nov. 7, 2003.

Narita et al., "Display of Active Enzymes on the Cell Surface of *Escherichia coli* Using PgsA Anchor Protein and Their Application to Bioconversion", Applied Genetics and Molecular Biotechnology, vol. 70(5), 564-572, 2006.

* cited by examiner

*Not drawn to scale

*Not drawn to scale

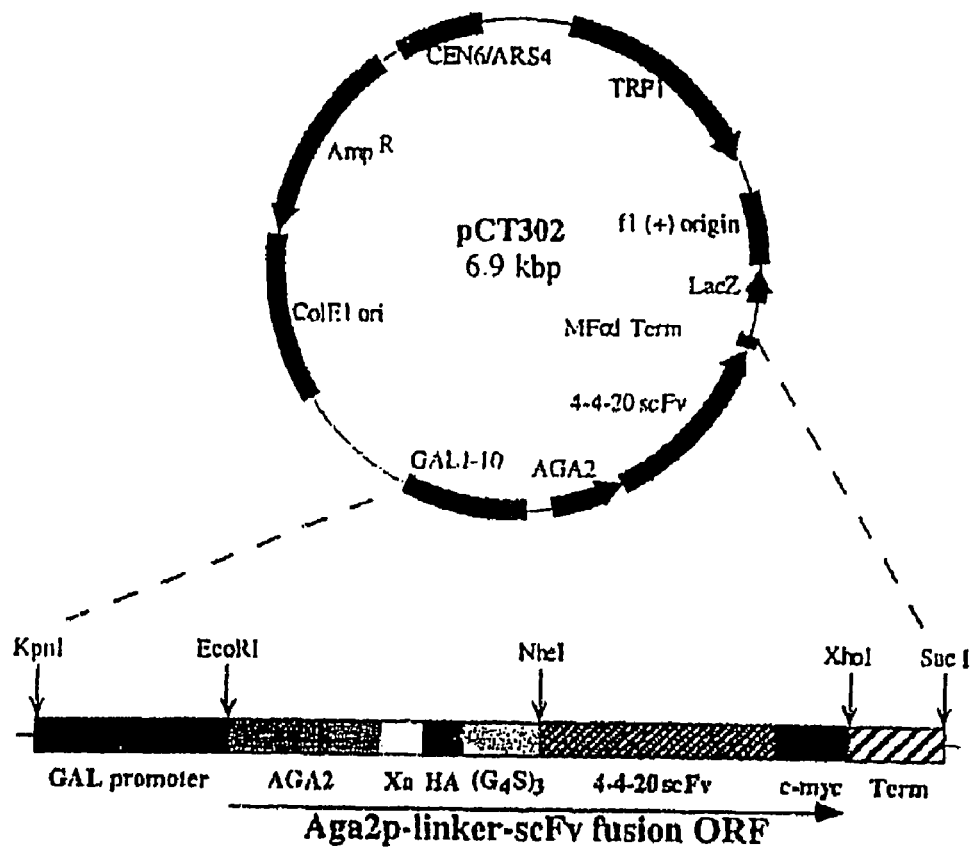

N-terminal flanking sequence:

```
ATAAACACACAGTATGTTTTTAAGGACAATAGCTCGACGATTGAAGGTAGATACCCATAC
 I  N  T  Q  Y  V  F  K  D  N  S  S  T  I  E  G  R  Y  P  Y  -
     Aga2p  <-|->  Linker  <- |Factor Xa^|-> HA
```

```
                    PstI/
GACGTTCCAGACTACGCTCTGCAGGCTAGTGGTGGTGGTGGTTCTGGTGGTGGTGGTTCT
 D  V  P  D  Y  A  L  Q  A  S  G  G  G  G  S  G  G  G  G  S  -
   epitope tag <-|->              Linker
```

```
             NheI/    AatII/
GGTGGTGGTGGTTCTGCTAGCGACGTCGTTATGACTCAAACACCACTATCACTTCCTGTT
 G  G  G  G  S  A  S  D  V  V  M  T  Q  T  P  L  S  L  P  V  -
               <-|-> VL of 4-4-20 scFv    (SEQ ID NO:4)
```

C-terminal flanking sequence:

```
                                      XhoI/    /BglII
TCCTCAGAACAAAAGCTTATTTCTGAAGAAGACTTGTAATAGCTCGAGATC
 S  S  E  Q  K  L  I  S  E  E  D  L  * (SEQ ID NO:5)-
<-|    |-> c-myc epitope tag <-|
```

Figure 4

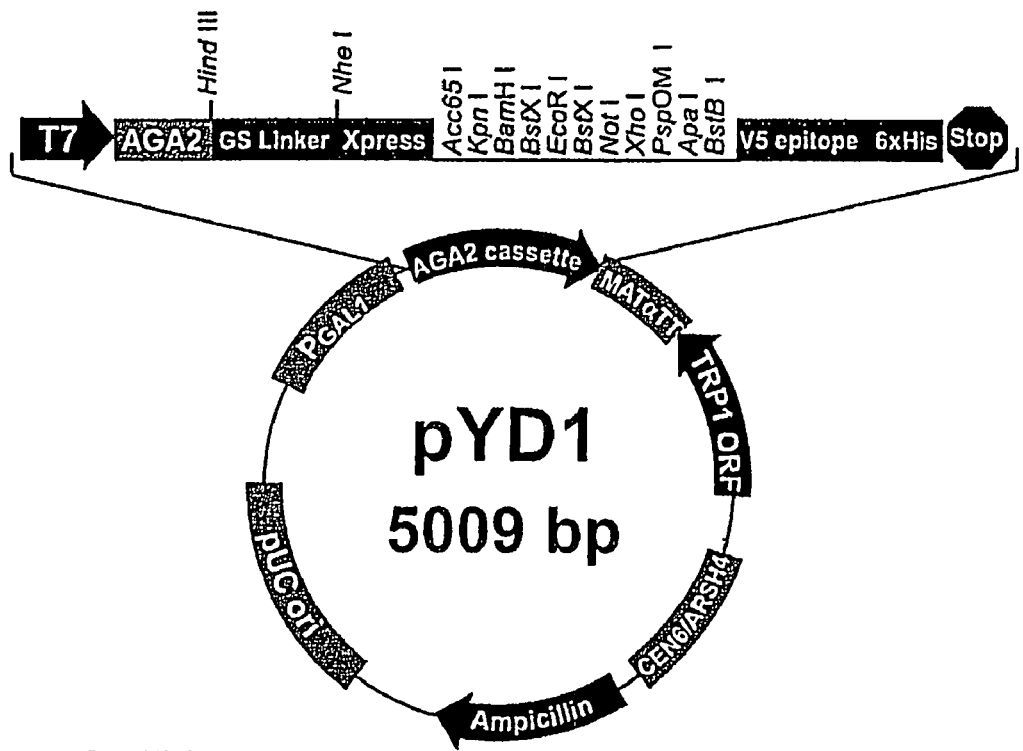

Comments for pYD1
5009 nucleotides

*GAL1* promoter: bases 1-451
T7 promoter priming site: bases 475-494
*AGA2* ORF: bases 534-794
pYD1 Forward priming site: bases 751-770
Gly/Ser Linker: bases 807-857
Xpress™ epitope: bases 891-914
Multiple cloning site: bases 914-992
V5 epitope: bases 993-1034
Polyhistidine region: bases 1044-1061
pYD1 Reverse priming site: bases 1114-1093 (C)
MATα transcription termination region: bases 1385-1098 (C)
*TRP1* ORF: bases 2107-1433 (C)
*CEN6/ARS4*: bases 2797-2282 (C)
Ampicillin resistance gene (ORF): bases 2931-3791
pUC origin: bases 3936-4609

Figure 5

```
                                                                          transcriptional start
320  AAACTGCAT AACCACTTTA ACTAATACTT TCAACATTTT CGGTTTGTAT TACTTCTTAT TCAAATGTAA TAAAAGTATC 400  AACAAAAAAT TGTTAATATA CCTCTATACT TTAACGTCAA GGAGAAAAAA CCCCGGATCG GACTACTAGC AGCTGTAATA
     ──T7 promoter/priming site──                                              ──Aga2 signal peptide──
480  CGACTCACTA TAGGGAATAT TAAGCTAATT CTACTTCATA CATTTTCAAT TAAG ATG CAG TTA CTT CGC TGT TTT
                                                                 Met Gln Leu Leu Arg Cys Phe ──Start of Aga2 mature peptide
565  TCA ATA TTT TCT GTT ATT GCT TCA GTT TTA GCA CAG GAA CTG ACA ACT ATA TGC GAG CAA ATC CCC
     Ser Ile Phe Ser Val Ile Ala Ser Val Leu Ala Gln Glu Leu Thr Thr Ile Cys Glu Gln Ile Pro
                                              ▲
                                         Cleavage site 621  TCA CCA ACT TTA GAA TCG ACG CCG TAC TCT TTG TCA ACG ACT ACT ATT TTG GCC AAC GGG AAG GCA
     Ser Pro Thr Leu Glu Ser Thr Pro Tyr Ser Leu Ser Thr Thr Thr Ile Leu Ala Asn Gly Lys Ala ──pYD1 Forward priming site──
687  ATG CAA GGA GTT TTT GAA TAT TAC AAA TCA GTA ACG TTT GTC AGT AAT TGC GGT TCT CAC CCC TCA
     Met Gln Gly Val Phe Glu Tyr Tyr Lys Ser Val Thr Phe Val Ser Asn Cys Gly Ser His Pro Ser End of Aga2 mature peptide ── Hind III      Pst I*
753  ACA ACT AGC AAA GGC AGC CCC ATA AAC ACA CAG TAT GTT TTT AAG CTT CTG CAG GCT AGT GGT GGT
     Thr Thr Ser Lys Gly Ser Pro Ile Asn Thr Gln Tyr Val Phe Lys Leu Leu Gln Ala Ser Gly Gly ──Gly-Ser Linker──                      Nhe I
819  GGT GGT TCT GGT GGT GGT GGT TCT GGT GGT GGT GGT TCT GCT AGC ATG ACT GGT GGA CAG CAA ATG
     Gly Gly Ser Gly Gly Gly Gly Ser Gly Gly Gly Gly Ser Ala Ser Met Thr Gly Gly Gln Gln Met ──Xpress™ epitope──    Acc65 I Kpn I  BamH I         BstX I  EcoR I    Pst I*
885  GGT CGG GAT CTG TAC GAC GAT GAC GAT AAG GTA CCA GGA TCC AGT GTG GTG GAA TTC TGC AGA TAT
     Gly Arg Asp Leu Tyr Asp Asp Asp Asp Lys Val Pro Gly Ser Ser Val Val Glu Phe Cys Arg Tyr
                   Enterokinase recognition site ▲ Enterokinase cleavage site BstX I  Not I   Xho I    Xba I  PspOM I Apa I BstB I                ──V5 epitope──
951  CCA GCA CAG TGG CGG CCG CTC GAG TCT AGA GGG CCC TTC GAA GGT AAG CCT ATC CCT AAC CCT CTC
     Pro Ala Gln Trp Arg Pro Leu Glu Ser Arg Gly Pro Phe Glu Gly Lys Pro Ile Pro Asn Pro Leu ──Polyhistidine region──       Pme I
1017 CTC GGT CTC GAT TCT ACG CGT ACC GGT CAT CAT CAC CAT CAC CAT TGA GTTTA AACCCGCTGA
     Leu Gly Leu Asp Ser Thr Arg Thr Gly His His His His His His ***

──pYD1 Reverse priming site──
1080 TCTGATAACA ACAGTGTAGA TGTAACAAAA TCGACTTTGT TCCCACTGTA CTTTTAGCTC GTACAAAATA CAAATATACTT 1160 TTCATTTCTC CGTAAACAAC ATGTTTTCCC ATGTAATATC CTTTTCTATT TTTCGTTCCG TTACCAACTT TACACATACT
     *The two Pst I sites are unique to the multiple cloning site                (SEQ ID.NO:7)
```

Figure 6

Restriction Map

| Enzyme | # of cuts | Positions |
|---|---|---|
| Acc65I | 1 | 915 |
| AccI | 1 | 2140 |
| AciI | 35 | 14 21(c) 108 737(c) 963(c) 967 1074 1504 2035(c) 2056 2828(c) 2875 2974(c) 3083(c) 3160(c) 3204 3325(c) 3371 3562(c) 3653(c) 4015 4024(c) 4159 4269(c) 4390(c) 4409(c) 4564(c) 4655 4676 4683 4726(c) 4750 4760 4816(c) 4919(c) |
| AcsI | 8 | 937 1320 1456 1940 2206 2344 2456 2756 |
| AcyI | 3 | 640 1562 3179 |
| AflIII | 3 | 1033 1179 4607 |
| AgeI | 2 | 72 1039 |
| AluI | 22 | 145 472 504 798 1137 1248 1347 1576 1593 1711 2116 3366 3429 3529 4050 4307 4443 4669 4787 4946 4968 5001 |
| Alw44I | 3 | 1393 3047 4293 |
| AlwI | 14 | 463 899 917(c) 930 2294 2651(c) 3080 3084(c) 3401 3864(c) 3865 3961(c) 3963 4049 |
| AlwNI | 2 | 594 4198 |
| AosI | 1 | 3496 |
| ApaI | 1 | 986 |
| ApaLI | 3 | 1393 3047 4293 |
| ApoI | 8 | 937 1320 1456 1940 2206 2344 2456 2756 |
| AseI | 6 | 271 2095 2608 3544 4779 4838 |
| AsnI | 6 | 271 2095 2608 3544 4779 4838 |
| Asp700 | 2 | 2598 3119 |
| Asp718 | 1 | 915 |
| AspEI | 1 | 3719 |

Figure 7a

| | | | |
|---|---|---|---|
| AspHI | | 7 | 1397 2028 2048 2153 3051 3136 4297 |
| AsuII | | 1 | 989 |
| AvaI | | 2 | 970 1596 |
| AvaII | | 4 | 2074 2796 3355 3577 |
| AviII | | 1 | 3496 |
| BamHI | | 1 | 922 |
| BanI | | 3 | 915 3766 4863 |
| BanII | | 2 | 986 1604 |
| BbrPI | | 2 | 2148 2785 |
| BbsI | | 4 | 49 59(c) 2222 2567(c) |
| BbvI | | 14 | 481 779 1280(c) 1698(c) 2103(c) 3285(c) 3676 3979(c) 4185(c) 4188(c) 4278 4697 4715 4796 |
| BcgI | | 4 | 526(c) 868(c) 1843 3181(c) |
| BfaI | | 12 | 142 466 758 809 860 977 2021 2664 3526 3861 4114 5006 |
| BglI | | 1 | 3601 |
| BmyI | | 10 | 986 1397 1604 1987 2028 2048 2153 3051 3136 4297 |
| BpmI | | 1 | 3650 |
| BpuAI | | 4 | 49 59(c) 2222 2567(c) |
| BsaAI | | 3 | 2138 2148 2785 |
| BsaHI | | 3 | 640 1562 3179 |
| BsaI | | 2 | 1027 3653 |
| BsaJI | | 6 | 451 1017 1771 2799 4447 4868 |
| BsaWI | | 5 | 72 1039 3423 4254 4401 |
| BsgI | | 2 | 1697(c) 1830 |
| BsiEI | | 7 | 77 967 2204 3201 3350 4273 4697 |
| BsiHKAI | | 7 | 1397 2028 2048 2153 3051 3136 4297 |
| BslYI | | 10 | 20 38 457 991 1018 4129 4408 4574 4592 4766 |
| BsII | | 10 | 20 38 457 991 1018 4129 4408 4574 4592 4766 |
| BsmAI | | 4 | 1027 1497 2877(c) 3653 |
| BsmFI | | 1 | 1642(c) |
| Bsp120I | | 1 | 982 |

Figure 7b

| | | | |
|---|---|---|---|
| Bsp1286I | | 10 | 986 1397 1604 1987 2028 2048 2153 3051 3136 4297 |
| BspHI | | 3 | 2260 2879 3887 |
| BspMI | | 1 | 1671 |
| BspWI | | 13 | 324 767 1599 2032 2052 2627 3601 3989 4561 4675 4742 4826 4870 |
| BsrBI | | 5 | 21 969(c) 2877(c) 4678(c) 4919 |
| BsrDI | | 3 | 692 3485 3659(c) |
| BsrFI | | 3 | 72 1039 3634 |
| BsrI | | 13 | 873 926(c) 1620(c) 1767 3074 3244(c) 3513 3556 3674 4080 4192(c) 4205(c) 4813 |
| Bst1107I | | 1 | 2141 |
| BstBI | | 1 | 989 |
| BstNI | | 7 | 182 920 2801 4448 4461 4582 4870 |
| BstUI | | 11 | 79 105 1035 2310 2828 3160 3653 3983 4564 4762 4764 |
| BstXI | | 2 | 933 959 |
| BstYI | | 8 | 891 922 3072 3089 3857 3869 3955 3966 |
| Bsu36I | | 1 | 1863 |
| CfoI | | 16 | 107 1543 2312 2828 3160 3497 3590 3983 4092 4266 4366 4433 4703 4736 4764 4829 |
| Cfr10I | | 3 | 72 1039 3634 |
| Csp45I | | 1 | 989 |
| Csp6I | | 9 | 645 897 916 1037 1128 1141 2473 3237 5009 |
| DdeI | | 13 | 1274 1376 1422 1440 1537 1717 1863 2278 2615 3218 3758 3924 4333 |
| DpnI | | 20 | 296 457 893 924 1080 2288 2658 3038 3074 3091 3349 3395 3413 3754 3859 3871 3949 3957 3968 4043 |
| DpnII | | 20 | 294 455 891 922 |

Figure 7c

| | | |
|---|---|---|
| | | 1078 2286 2656 3036 3072 3089 3347 3393 3411 3752 3857 3869 3947 3955 3966 4041 |
| DraI | 6 | 1069 2452 2761 3141 3833 3852 |
| DraII | 4 | 982 983 2225 2796 |
| DrdI | 1 | 4505 |
| DsaV | 12 | 180 451 918 1957 2799 3181 3532 4228 4446 4459 4580 4868 |
| EaeI | 4 | 671 964 3326 4768 |
| EagI | 1 | 964 |
| Eam1105I | 1 | 3719 |
| EarI | 5 | 154(c) 2407(c) 2620(c) 2920(c) 4724(c) |
| EclXI | 1 | 964 |
| Eco57I | 3 | 560(c) 3053 4065(c) |
| EcoO109I | 4 | 982 983 2225 2796 |
| EcoRI | 1 | 937 |
| EcoRII | 7 | 180 918 2799 4446 4459 4580 4868 |
| EcoRV | 2 | 949 1823 |
| Fnu4HI | 26 | 14 108 470 768 964 967 1294 1712 2036 2056 2117 2975 3204 3299 3326 3665 3993 4199 4202 4267 4410 4565 4683 4686 4704 4785 |
| FnuDII | 11 | 79 105 1035 2310 2828 3160 3653 3983 4564 4762 4764 |
| FokI | 5 | 241 1842(c) 3280 3567 3748 |
| FspI | 1 | 3496 |
| HaeII | 2 | 4367 4737 |
| HaeIII | 16 | 185 673 966 984 2038 2181 2227 3328 3595 3675 4133 4536 4567 4585 4596 4770 |
| HgaI | 6 | 47(c) 648 1551(c) 3187 3917(c) 4495(c) |
| HgiAI | 7 | 1397 2028 2048 2153 3051 3136 4297 |
| HhaI | 16 | 107 1543 2312 2828 |

Figure 7d

|  |  |  | 3160 3497 3590 3983 4092 4266 4366 4433 4703 4736 4764 4829 |
|---|---|---|---|
| HinP1I |  | 16 | 105 1541 2310 2826 3158 3495 3588 3981 4090 4264 4364 4431 4701 4734 4762 4827 |
| HincII |  | 2 | 656 3177 |
| HindII |  | 2 | 656 3177 |
| HindIII |  | 1 | 796 |
| HinfI |  | 19 | 45 130 208 482 634 973 1027 1366 1371 1474 1672 1749 1798 2017 2667 4237 4633 4708 4773 |
| HpaII |  | 14 | 73 453 1040 1958 3182 3424 3534 3601 3635 4039 4229 4255 4402 4891 |
| HphI |  | 15 | 36 62(c) 614(c) 736(c) 1042(c) 1048(c) 1538(c) 1643(c) 2058(c) 2152(c) 2992(c) 3027 3233(c) 3649 3876 |
| ItaI |  | 26 | 14 108 470 768 964 967 1294 1712 2036 2056 2117 2975 3204 3299 3326 3665 3993 4199 4202 4267 4410 4565 4683 4686 4704 4785 |
| KpnI |  | 1 | 919 |
| Ksp632I |  | 5 | 154(c) 2407(c) 2620(c) 2920(c) 4724(c) |
| MaeI |  | 12 | 142 466 758 809 860 977 2021 2664 3526 3861 4114 5006 |
| MaeII |  | 8 | 434 721 2137 2147 2784 3117 3490 3906 |
| MaeIII |  | 18 | 24 176 539 717 1101 1219 2158 2298 2416 3058 3246 3399 3457 3788 4071 4187 4250 4846 |
| MboI |  | 20 | 294 455 891 922 1078 2286 2656 |

Figure 7e

| | | | |
|---|---|---|---|
| | | | 3036 3072 3089 3347 3393 3411 3752 3857 3869 3947 3955 3966 4041 |
| MboII | | 15 | 54 59(c) 171 2227 2424 2439 2567(c) 2637 2671(c) 2937 3046 3124 3879 3950(c) 4741 |
| McrI | | 7 | 77 967 2204 3201 3350 4273 4697 |
| MfeI | | 1 | 1964 |
| MluI | | 1 | 1033 |
| MluNI | | 1 | 673 |
| MnlI | | 32 | 43 61 72 111 155(c) 431 630 759 973(c) 1022 1027 1511 1690(c) 1766(c) 1869 2049 2180 2184 2193 2238 2323 3346(c) 3552(c) 3699 3780 4180 4430(c) 4504 4713(c) 4763 4861 4991 |
| MscI | | 1 | 673 |
| MseI | | 37 | 216 271 301 338 413 431 500 530 794 1068 1285 1408 1532 1756 2095 2131 2254 2324 2451 2511 2531 2608 2707 2733 2751 2760 3140 3505 3544 3779 3832 3846 3851 3903 4779 4838 4976 |
| MslI | | 4 | 1806 2948 3307 3466 |
| MspA1I | | 6 | 472 1076 3083 4024 4269 4787 |
| MspI | | 14 | 73 453 1040 1958 3182 3424 3534 3601 3635 4039 4229 4255 4402 4891 |
| MunI | | 1 | 1964 |
| MvaI | | 7 | 182 920 2801 4448 4461 4582 4870 |
| MvnI | | 11 | 79 105 1035 2310 2828 3160 3653 3983 4564 4762 4764 |
| MwoI | | 13 | 324 767 1599 2032 |

Figure 7f

| | | | |
|---|---|---|---|
| | | | 2052 2627 3601 3989 4561 4675 4742 4826 4870 |
| NciI | | 5 | 453 1959 3183 3534 4230 |
| NdeII | | 20 | 294 455 891 922 1078 2286 2656 3036 3072 3089 3347 3393 3411 3752 3857 3869 3947 3955 3966 4041 |
| NheI | | 1 | 859 |
| NlaIII | | 12 | 867 1183 1193 2264 2883 3276 3312 3390 3400 3891 4611 4957 |
| NlaIV | | 14 | 186 917 924 984 2798 2832 3422 3633 3674 3768 4535 4579 4865 4895 |
| NotI | | 1 | 964 |
| NspI | | 2 | 1183 4611 |
| NspV | | 1 | 989 |
| PaeR7I | | 1 | 970 |
| PinAI | | 2 | 72 1039 |
| PleI | | 9 | 39(c) 476(c) 981 1482 1757 1792(c) 2675 4231(c) 4716 |
| PmaCI | | 2 | 2148 2785 |
| PmeI | | 1 | 1069 |
| PmlI | | 2 | 2148 2785 |
| PpuMI | | 1 | 2796 |
| Psp1406I | | 3 | 721 3117 3490 |
| PstI | | 2 | 806 946 |
| PvuI | | 1 | 3350 |
| PvuII | | 2 | 472 4787 |
| RcaI | | 3 | 2260 2879 3887 |
| RsaI | | 9 | 1 646 898 917 1038 1129 1142 2474 3238 |
| SapI | | 2 | 2620(c) 4724(c) |
| Sau3AI | | 20 | 294 455 891 922 1078 2286 2656 3036 3072 3089 3347 3393 3411 3752 3857 3869 3947 3955 3966 4041 |
| Sau96I | | 12 | 184 982 983 2074 2180 2225 2796 3355 3577 3594 3673 4534 |

Figure 7g

| | | |
|---|---|---|
| ScaI | 1 | 3238 |
| ScrFI | 12 | 182 453 920 1959 2801 3183 3534 4230 4448 4461 4582 4870 |
| SfaNI | 7 | 524(c) 1552 2020 3018(c) 3267 3458(c) 4510(c) |
| SfcI | 6 | 488 802 942 3473 4151 4342 |
| SfuI | 1 | 989 |
| SnoI | 3 | 1393 3047 4293 |
| SspI | 4 | 498 560 706 2914 |
| SwaI | 1 | 2761 |
| TaqI | 11 | 637 971 989 1025 1111 1369 1631 2200 2527 3065 4509 |
| TfiI | 10 | 130 208 634 1027 1366 1371 1672 2017 4633 4773 |
| ThaI | 11 | 79 105 1035 2310 2828 3160 3653 3983 4564 4762 4764 |
| Tru9I | 37 | 216 271 301 338 413 431 500 530 794 1068 1285 1408 1532 1756 2095 2131 2254 2324 2451 2511 2531 2608 2707 2733 2751 2760 3140 3505 3544 3779 3832 3846 3851 3903 4779 4838 4976 |
| Tsp509I | 35 | 168 213 268 407 506 527 732 937 1280 1286 1309 1320 1329 1382 1456 1940 1964 2092 2206 2336 2344 2456 2598 2708 2734 2756 2762 2768 3286 3541 3847 4835 4910 4927 4973 |
| XbaI | 2 | 976 2020 |
| XhoI | 1 | 970 |
| XhoII | 8 | 891 922 3072 3089 3857 3869 3955 3966 |
| XmaIII | 1 | 964 |
| XmnI | 2 | 2598 3119 |

Figure 7h

No cuts: AatI, AatII, AccIII, AflII, AscI, AspI, AvrII, BclI, BfrI, BglII, BlnI, Bpu1102I, BsaBI, BseAI, BsiWI, BsmI, BspDI, BspEI, BsrGI, BssHII, BstEII, CelII, ClaI, DraIII, DsaI, Ecl136II, Eco47III, EcoNI, Esp3I, EspI, HpaI, KasI, KspI, MamI, MroI, NaeI, NarI, NcoI, NdeI, NgoMI, NruI, NsiI, PacI, PflMI, Ppu10I, RsrII, SacI, SacII, SalI, ScxAI, SfiI, SgrAI, SmaI, SnaBI, SpeI, SphI, SspBI, StuI, StyI, Tth111I, Van91I, XcmI, XmaI

Figure7i

USE OF CELL SURFACE DISPLAYS IN YEAST CELL CATALYST SUPPORTS

CROSS-REFERENCE TO RELATED APPLICATION

This Application claims the benefit of priority to U.S. Provisional Patent Application Ser. No. 60/851,434, filed on Oct. 13, 2006. U.S. Provisional Patent Application Ser. No. 60/851,434 is incorporated by reference into this Application as if fully rewritten herein.

BACKGROUND OF THE INVENTION

1. Field of the Invention

The present invention relates to the use of surface display technology as a uniform catalyst support for synthetic catalysts. Catalyst supports of the invention include uniform layers of catalyst on their surface, allowing catalysis with properties of homogeneous catalysts, while still allowing efficient separation and recycling of the catalyst. Although a variety of biological supports are taught herein, yeast cell-supported catalysts are particularly preferred.

2. Background

A. Cell Surface Displays

A number of microorganisms and virions may be engineered so that proteins are genetically displayed on their surface. The yeast Saccharomyces cerevisiae is often used for this process. A number of methods, structures, and applications of yeast cell-surface display have been reported. Kondo, A., and Ueda, M., "Yeast Cell-Surface Display—Applications of Molecular Display," Appl. Microbiol. Biotechnol. 64:28-40 (2004); Ueda, M. & Tanaka, A., "Cell Surface Engineering of Yeast: Construction of Arming Yeast with Biocatalyst" J. Biosci. and Bioeng. 90(2): 125-136 (2000).

Boder and Wittrup report that S. cerevisiae is ideal for cell surface display of proteins, because S. cerevisiae possesses both secretory machinery and protein folding mechanisms that are similar to those of mammalian cells. (Boder, E. T. & Wittrup, D. K., "Yeast Surface Display for Screening Combinatorial Polypeptide Libraries," Nature Biotech. 15:553-557 (1997)). Other benefits include large numbers of surface fusions per cell and the ability to test the cells using flow cytometry. (Boder, et al.). Yeast cells may display proteins of differing stability and expression level, as reported by Park, et al., "Limitations of Yeast Surface Display in Engineering Proteins of High Thermostability," PEDS, 19(5): 211-217 (2006).

Yeast cell surface display technology is further reported in U.S. Pat. No. 6,423,538, to Wittrup, et al., "Yeast Cell Surface Display of Proteins and Uses Thereof." Wittrup, et al., reports a genetic method for anchoring polypeptides to a yeast cell wall. U.S. Pat. No. 6,300,065, to Kieke, et al., "Yeast Cell Surface Display of Proteins and Uses Thereof," reports a method for the fusion of the N-terminus of a "polypeptide of interest" to the C-terminus of the yeast Aga2p cell wall protein.

Kieke's method may purportedly be used for anchoring an scFv antibody fragment to exterior of the yeast cell wall. Yeast cell surface display has also been reported for use in antibody epitope mapping. Chao, et al., "Fine Epitope Mapping of Anti-Epidermal Growth Factor Receptor Antibodies Through Random Mutagenesis and Yeast Surface Display," J. Mol. Biol., 342(2): 539-550 (2004); see also Colby, et al., "Development of a Human Light Chain Variable Domain ($V_L$) Intracellular Antibody Specific for the Amino Terminus of Huntingtin via Yeast Surface Display," J. Molec. Biol. 342(3): 901-912 (2004); Min Li, "Applications of Display Technology in Protein Analysis," Nature Biotech. 18:1251-1256 (2000); Feldhaus, M. J. & Siegel, R. W., "Yeast Display of Antibody Fragments: A Discovery and Characterization Platform," J. Immunol. Methods 290(1-2): 69-80 (2004); Weaver-Feldhaus, et al., "Directed Evolution for the Development of Conformation-Specific Affinity Reagents using Yeast Display" 18(11): 527-536 (2005); Little, et al., "Bacterial Surface Presentation of Proteins and Peptides: An Alternative to Phage Technology?" Trends in Biotechnology 11 (1993).

Cell surface display has also reportedly been used for absorption of environmental metals. Wernerus, H. & Stahl, S., "Biotechnological Applications for Surface-Engineered Bacteria" Biotechnol. Appl. Biochem. 40:209-228 (2004). Cell surface display has also reportedly been used to bind eukaryotic cell display libraries to solid surfaces. Peelle, et al., U.S. Pat. Appl'n No. U.S.2006/0003387, "Cell Display Libraries"; Andres, et al., "Immobilization of Saccharomyces cerevisiae Cells to Protein G-Sepharose by Cell Wall Engineering" J. Mol. Microbiol. & Biotech. 5(3) 161-166 (2003). Expression of the ZZ domain from Staphylococcus aureus, which binds to the Fc part of immunoglobulin G (IgG) has also been reported. Shimojyo, et al., "Preparation of Yeast Strains Displaying IgG Binding Domain ZZ and Enhanced green Fluorescent Protein for Novel Antigen Detection Systems" J. Biosci & Bioeng. 96(5):493-495 (2003).

Kondo reports that yeast cell surface display has been used for biocatalysis; however, Kondo's biocatalysts have a number of disadvantages that hinder their general applicability. For example, the biocatalysts are bound directly to the surface of the yeast cell. Such catalysts may not be interchanged for other catalysts as the need arises, and familial yeast lines are limited to a single biocatalyst configuration. Furthermore, biocatalyst that is adsorbed to an unwanted target is difficult or impossible to remove or separate from a cell without irrevocably damaging the cell. Biocatalysts are also traditionally limited to those catalysts that may be expressed directly on the cell surface, such as protein molecules or enzymes.

Cell surface display using microorganisms other than yeast has also been reported. For example, Wang, et al., "Specific Adhesion to Cellulose and Hydrolysis of Organophosphate Nerve Agents by a Genetically Engineered Escherichia coli Strain with a Surface-Expressed Cellulose-Binding Domain and Organophosphorus Hydrolase," App. and Env. Microbiol. 68(4): 1684-1689 (2002), reports degradation of parathion and paraoxon using a strain of E. coli displaying organophosphorus hydrolase (OPH) and a cellulose-binding domain. The OPH was expressed on the cell surface using the Lpp-OmpA fusion system or the truncated ice nucleation protein anchor.

B. Catalyst Supports

There is a need for catalyst supports that are uniform in size and that have the catalyst distributed evenly over the surface of the catalyst support. Uniform supports offer a number of advantages, including minimizing the effects of diffusion and differences between catalyst sites. Catalyst supports may also aid in convenient handling of some catalysts.

One example of generally uniform inorganic catalyst supports may be found in United States Patent Application Publication No. 2006/0009354, to Yueng, et al. The '354 publication reports a catalytic material comprising a metal catalyst anchored to a metal oxide crystal. The metal catalyst is anchored to the surface of the metal oxide by interacting with a hydroxyl group on the surface of the metal oxide.

Catalysts such as those reported in the '354 publication have a number of disadvantages. For example, they may be unsuitable for organic use. Furthermore, they may allow only the use of metal catalysts. Their production may also be expensive, and their construction may make catalyst regeneration difficult. Each support may be limited to a single catalyst.

Embodiments of the invention provide catalysts and catalyst supports that may address one or more of the above disadvantages of the prior art. Methods of construction, use, and regeneration of those catalysts are also provided.

SUMMARY OF THE INVENTION

The present invention provides a catalytic material comprising one or more receptor proteins disposed from the surface of a biological support. In a typical embodiment, the receptor proteins are disposed uniformly over the surface of the biological support. The receptor proteins may be identical proteins, or they may be different proteins. Each receptor protein is linked to an anchoring protein that is engaged with surface of the biological support.

In a typical practice, the receptor protein is linked to the anchoring protein in the form of a fusion protein, whereby amino acids of the anchoring protein domain are linked as a continuous polypeptide sequence with amino acids of the receptor protein, thereby forming a heterologous fusion protein having an anchoring domain from the anchoring protein and ligand binding domain from the receptor protein. The anchoring domain may engage the surface of the biological support by binding to, being adsorbed within, or being cross-linked to, other proteins or carbohydrates disposed on the surface of the biological support. Typically, when the biological support is a cell, the anchoring domain is embedded in the outer membrane of the cell or binds to a cell wall protein or carbohydrate. Depending on the anchoring protein used, the anchoring domain may be partly disposed within the surface of the biological support, for example in the form of a peripheral membrane protein, or may extend through the biological support surface, for example, in the form of an integral membrane protein. Each receptor protein contains a ligand binding domain that is further bound to a ligand, and each ligand in turn is bound to a catalyst. Receptor-ligand binding and ligand-catalyst binding may be accomplished by covalent (e.g. chemical cross-linking) or non-covalent binding The invention further provides a catalyst support system comprising one or more receptor proteins displayed on the surface of a biological support. The receptor proteins are thereby typically displayed uniformly over the surface. The receptor proteins may be identical proteins or different proteins. The receptor proteins are selected to bind to a selected ligand, which in turn is selected to bind to a selected catalyst to be supported.

The invention also provides a method for making a catalytic material and/or a catalyst support system as described above. One or more receptor proteins are expressed as fusion proteins with anchoring proteins and distributed about the surface of a biological support. In one embodiment the proteins are identical proteins, and in another embodiment they are one or more different proteins. In one embodiment the proteins are displayed uniformly about the surface of a biological support, forming a catalyst support material. One or more catalyst molecules are bound to respective ligands to form ligand/catalyst constructs. The ligands are designed or chosen to selectively bind or be cross-linked to the binding domain of the receptor proteins, referred to herein as "tethering". The ligand/catalyst constructs and the biological supports displaying the receptor protein(s) are mixed, allowing the ligand/catalyst constructs to be tethered to the receptor proteins, forming a catalytic material.

Biological supports may be selected from, for example, virions and microorganisms. Microorganisms may be, for example, bacteria or yeasts. Bacteria may be, for example, from the genus *Escherichia, Corynebacterium, Bacillus*, or *Lactococcus. Escherichia coli* is a preferred bacterium. Yeasts for use in the invention may include those, for example, from the genus *Saccharomyces, Pichia* or *Candida*. A preferred yeast is *Saccharomyces cerevisiae*.

BRIEF DESCRIPTION OF THE SEVERAL VIEWS OF THE DRAWINGS

FIG. 4 shows plasmid pCT302 (Boder & Wittrup), which may be used to express a receptor protein as a fusion to the yeast Aga2p agglutinin mating protein under the control of the GAL 1,10 galactose-inducible promoter. The N-terminal flanking sequence of pCT302 is shown as SEQ ID NO: 4, and the C-terminal flanking sequence is shown as SEQ ID NO: 5.

FIG. 5 shows a map of plasmid pYD1 (SEQ ID NO: 6).

FIG. 6 shows the polylinker of plasmid pYD1 (SEQ ID NO: 7).

FIGS. 7*a-i* show a restriction map of plasmid pYD1.

DETAILED DESCRIPTION OF THE INVENTION

The description that follows makes citation to various references that may aid one of ordinary skill in the art to understand or practice various aspects of the present invention. Citation to such references is intended as a short-hand method to direct the skilled person to more detailed techniques and example materials and systems of the prior art that may be used to practice the present invention. Accordingly, each such reference is incorporated herein by reference to the extent necessary to accomplish that purpose. Citation of a reference herein is not an admission that such a reference constitutes prior art for any determination of patentability.

As used herein, the singular forms "an," "a," and "the" used in the specification and claims include both singular and plural unless the content clearly dictates otherwise. In particular, those skilled in the art will recognize that while design and creation of catalytic materials and catalytic supports are described in terms of a single cell or other biological support, more effective systems will include one or more cells or biological supports each expressing one or more receptor proteins.

As used herein, the term "anchoring protein" means a polypeptide sequence having an amino acid sequence domain, or combination of domains, that function(s) to engage the polypeptide with the surface of a biological particle, such as a cell, virus or virion shell. The polypeptide sequence need not, and typically does not, embody an entire protein as it would occur naturally in nature, but rather need only include a fragment or fragments of such proteins carrying a sufficient amount of the amino acid sequence as necessary to provide the anchoring domains. It is understood by one of skill in the art, that in certain cases, anchoring domains may include two or more contiguous sequences of amino acids that engage within a membrane of a cell separated by one or more contiguous sequences that do not engage with the membrane. In such cases, only the domains that engage with membrane and are necessary to provide the anchoring function need be included, while the amino acid sequences that do not engage with the membrane may be deleted altogether, or replaced by sequences that are heterologous to the naturally occurring protein.

One aspect of the invention provides a catalytic support material including a biological support that displays one or more receptor proteins on the biological support surface. This catalytic support provides uniform availability to catalysts bound to a ligand that will be tethered to a receptor protein. These catalysts may be organic or inorganic. Unlike prior art surface display catalysis technology, the catalysts are not limited to enzymes or proteins that can be fused to natural anchoring proteins and expressed by the biological support.

Figure 3:
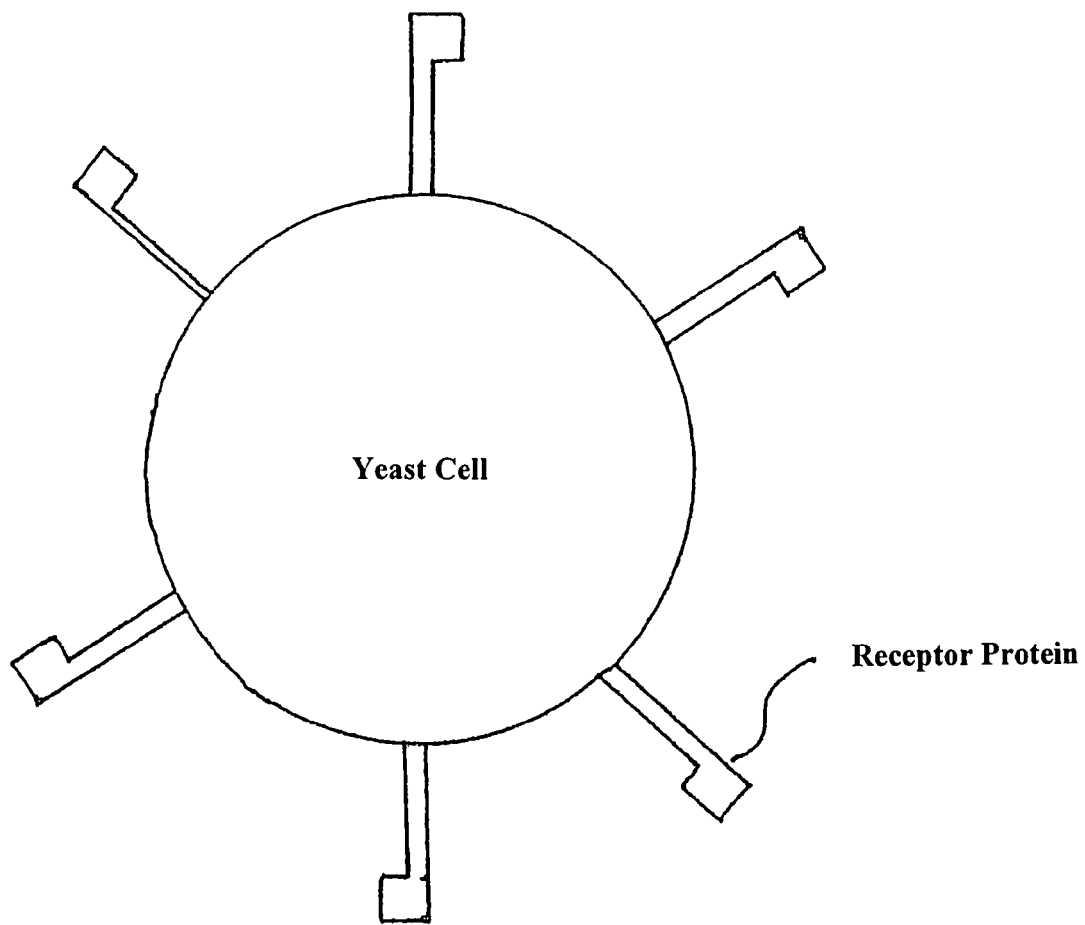
FIG. 3 shows a catalytic support material comprising a yeast cell and one or more of receptor proteins exhibited on the surface of the yeast cell.

In one embodiment, the catalytic support material comprises a yeast cell and one or more receptor proteins displayed on the surface of the yeast cell, as represented by FIG. 3. The receptor proteins are anchored to the surface of the cell by fusion to proteins that anchor to the cell wall by operation of native yeast cell mechanisms. For example, the agglutinin system and the flocculin system are well known to those skilled in the art and may be used in embodiments of the invention. Anchoring may be accomplished, for example, by creation of fusion proteins in which (1) the receptor proteins are fused to the C-terminal half of an α-agglutinin construct; (2) the receptor proteins are fused to the N-terminal half of an a-agglutinin construct; (3) the receptor proteins are fused to the C-terminal region of Flo1p; or (4) the receptor proteins are fused to the flocculation functional domain of Flo1p. Possible receptor proteins include avidin (SEQ ID NO: 26), a cellulose binding domain, a lectin, and antibody binding domains.

In one embodiment of the invention, the receptor proteins are introduced to the yeast cell by expression of one or more genes that have either been added to the yeast cell or added to a parent of the yeast cell. Genes may be added, for example, by transformation using lithium salts, spheroplasts, a gene gun, or electroporation.

Methods of making catalytic support materials are also provided herein. In one embodiment of the invention, a biological support expresses a receptor protein fused to a native yeast protein that is exported to the outer membrane of the yeast cell. One or more receptor proteins are displayed about the surface of the yeast cell. The receptor proteins may be identical proteins or they may be different proteins. The receptor proteins may be distributed uniformly about the surface of the yeast cell. The receptor proteins will bind to ligands that may be attached to catalysts to be supported by the catalyst support systems.

In a further embodiment the invention includes a catalytic material. The catalytic material includes an organic or an inorganic catalyst bound to a ligand, which is in turn tethered to a receptor protein on a yeast catalytic support material as described herein. A catalytic material of the invention is shown in two-dimensional view in FIG. 1. The catalyst forms a mono-layer on the yeast cell surface. This gives the properties of homogeneous catalysis, yet still allows efficient separation and ready recycling of the catalyst.

I. Cells and Other Biological Supports

A variety of biological cells are suitable for use in embodiments of the invention. Those skilled in the art will recognize that many strains of microorganisms are suitable for use in embodiments of the invention. Strains of yeast are preferred. Strains of the yeast *Saccharomyces cerevisiae* are particularly suitable in embodiments of the invention, in part because their genome has been extensively studied, and because they enjoy GRAS ("Generally Regarded As Safe") status with the Food and Drug Administration. *Saccharomyces cerevisiae* is recognized as a model eukaryote capable of rapid growth and with a versatile DNA transformation system.

Background information and exemplary methods and media for growing, testing and preserving yeast in general and *S. cerevisiae* in particular may be found, for example, in Sherman, F., "Getting Started with Yeast," Dept. of Biochem. and Biophysics, Univ. of Rochester Med. Sch. (August 2003) (adapted from Sherman, F., "Getting Started with Yeast," *Methods Enzymol.*, 350:3-41 (2002) (hereinafter "Sherman (I)"); and in Sherman, F., "An Introduction to the Genetics and Molecular Biology of the Yeast *Saccharomyces cerevisiae*," Dept. of Biochem. and Biophysics, Univ. of Rochester Med. Sch. (1998) (modified from Sherman, F., "Yeast Genetics," *The Encyclopedia of Molecular Biology and Molecular Medicine*," 6:302-325 (edited by R. A. Meyers, Weinheim, Germany, 1997); and Burke, D., et al., "Methods in Yeast Genetics: A Cold Spring Harbor Laboratory Course Manual" (Cold Spring Harbor Laboratory Press, Cold Spring Harbor, N.Y., 2000); Colby, et al. "Engineering Antibody Affinity by Yeast Surface Display" *Methods Enzymol.* 388:348-58 (2004).

Some non-yeast microorganisms and virions also have display mechanisms that have been studied and that may be useful in embodiments of the invention. For example, *Escherichia coli* may be used for surface display of enzymes with the aid of a PgsA anchor. Narita, et al., "Display of Active Enzymes on the Cell Surface of *Escherichia coli* using PgsA Anchor Protein and Their Application to Bioconversion," *Appl. Microbiol. Biotechnol.* (2005). Display of lipase using fadL as an anchor has been reported. Lee, S. H., et al., "Display of Bacterial Lipase on the *Escherichia coli* Cell Surface by Using FadL as an Anchoring Motif and Use of the Enzyme in Enantioselective Biocatalysis" *Appl. & Env. Microbiol.* 70(9): 5074-80 (2004). Cell surface display of proteins on *Lactococcus lactis* has also been reported. Steidler, et al., "Functional Display of a Heterologous Protein on the Surface of *Lactococcus lactis* by Means of the Cell Wall Anchor of *Staphylococcus aureus* Protein A" *Appl. & Env. Microbiol.* 64(1): 342-345 (1998).

In other embodiments, the biological support can be a virion. Virions may be eukaryotic viruses or bacteriophages, either as complete virion particles, or as so called "naked" virions, which are viral particles devoid of the viral genome. Suitable eukaryotic viruses include those commonly used for genetic engineering purposes, including, for example, baculovirus, adenoviruses, adeno-associated viruses and retroviruses. Similarly, suitable bacteriophages include, for example, λ phage (Lysogen), T4 phage, T7 phage, R17 phage, M13 phage, MS2 phage, G4 phage, P1 phage, P2 phage, N4 phage, φ6 phage, and φ429 phage. The filamentous phage of the M13, including but not limited to M13, fd, and fl, are preferred. Methods of displaying receptors on the surface of bacteriophages are well known in the art. Phage display is reported, for example, in Willats, W. G. T., "Phage Display: practicalities and prospects," *Plant Mol. Biol.* 50: 873-54 (2002); Bass, et al., "Hormone Phage: An Enrichment Method for Variant Proteins with Altered Binding Properties," *Proteins: Structure, Function, and Genetics,* 8:309-314 (1990); and Zucconi, et al., "Selection of Ligands by Panning of Domain Libraries Displayed on Phage Lambda Reveals New Potential Partners of Synaptojanin 1," *J. Mol. Biol.* 307: 1329-1339 (2001), all of which are incorporated by reference herein. Creation and use of avidin-displaying Baculovirus is reported by Räty, et al., "Enhanced Gene Delivery by Avidin-Displaying Baculovirus" *Mol. Therapy.* 9(2):282-291 (2004). Surface display using bacteriophage T7 is reported in the "T7 Select® System Manual," TB178 Rev.B0203, copyright 2003 by Novagen, Inc.

II. Anchoring Proteins

Those skilled in the art will recognize that a variety of anchoring proteins may be used in embodiments of the invention. Ideally, anchoring proteins will not be essential to cellular functions or structures, thereby avoiding growth defects or functional issue with the cell or other biological support. Lee, et al., "Microbial Cell-Surface Display" *Trends in Biotech.* 21(1): 45-52 (2003). Lee, et al. reports beneficial characteristics of anchoring proteins:

A successful carrier should meet the following four requirements: it should have an efficient signal peptide or transporting signal to allow premature fusion protein to go through the inner membrane; it should have strain anchoring structure to keep fusion proteins on the cell surface without detachment; it should be compatible with the foreign sequences to be inserted or fused (i.e. the carrier should not become unstable on the insertion or fusion of heterologous sequences); and it should be resistant to attack by proteases present in the periplasmic space or medium.

Boder and Wittrup (supra) report two cell-surface receptors that may be fused to proteins of interest and anchored to the cell wall. These receptors, a-agglutinin and α-agglutinin, are normally used by the yeast to enable cell fusion prior to diploid formation.

Boder and Wittrup report using a-agglutinin in the development of yeast cell surface display of a functional antifluorescein scFv and c-myc epitope tag on the cell wall of *S. cerevisiae*. They claim that this was accomplished by C-terminal fusion of the protein of interest to the Aga2 protein (SEQ ID NO: 8). The Aga2 protein is linked to the Aga1 protein subunit (SEQ ID NO: 2) by disulfide bonds. In turn, the Aga1 subunit is anchored to the cell wall by β-glucan covalent bonding. Boder and Wittrup further report construction of a vector in which the Aga2-scFv fusion is placed under the control of the inducible GAL1 promoter (SEQ ID NO: 9). A nucleic acid sequence encoding the Aga1 protein is given in SEQ ID NO: 10. A nucleic acid sequence encoding the Aga2 protein is given in SEQ ID NO: 11. A nucleic acid sequence encoding an α-agglutinin gene (sag1) is reported in SEQ ID NO: 12.

Figure 1:
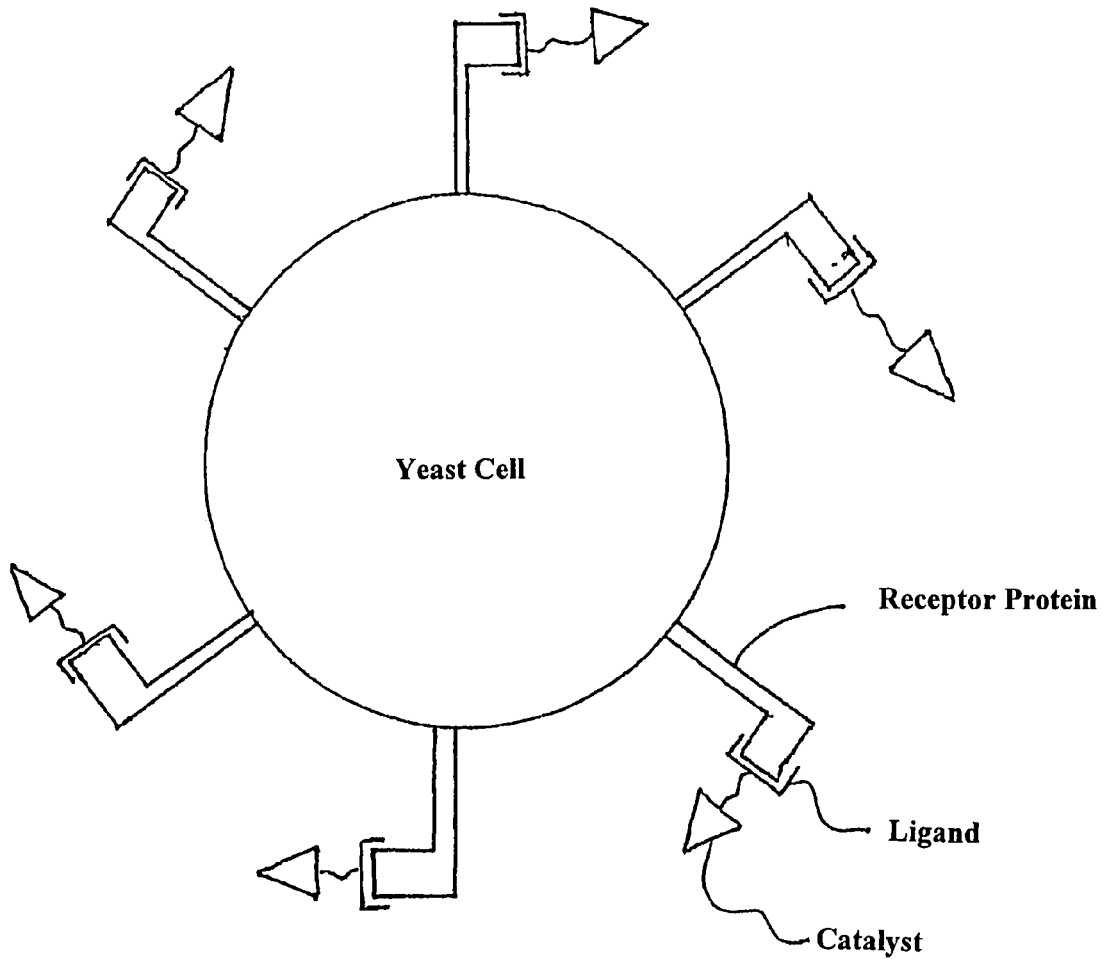
FIG. 1 schematically depicts a two-dimensional view of a single yeast cell surface display catalyst system of the invention.
Figure 2:
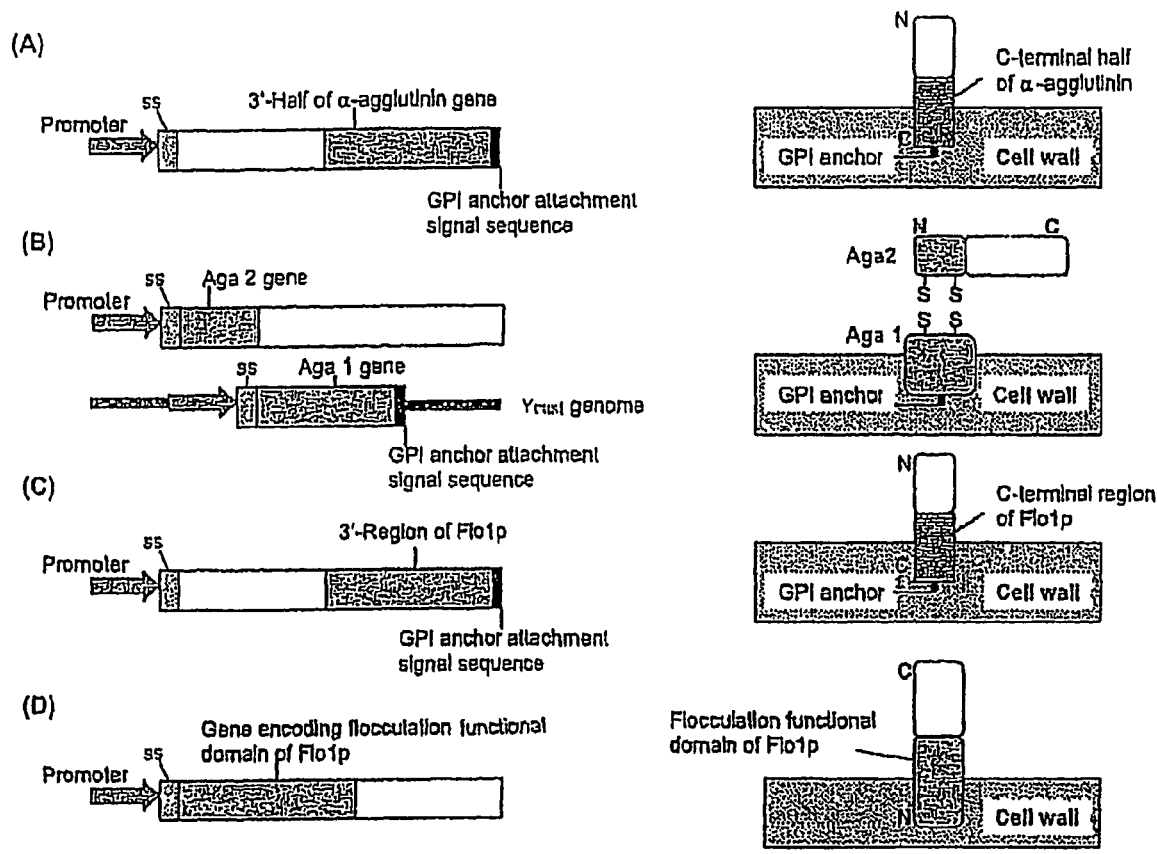
FIG. 2 shows yeast cell surface display systems using A a-agglutinin (SEQ ID NO: 1), B a-agglutinin (SEQ ID NO: 2), C C-terminus region of Flo1p (SEQ ID NO: 3), and D N-terminus flocculation function domain of Flo1p (SEQ ID NO: 3). (Kondo, supra.; and van der Vaart, J. M., et al., "Comparison of Cell Wall Proteins of *Saccharomyces cerevisiae* as anchors for Cell Surface Expression of Heterologous Proteins," *App. & Env. Microbiol.* 63(2): 615-620 (1997)).

A number of methods for anchoring these proteins have been described, as shown in FIG. 1. These methods include glycosylphosphatidylinositol (GPI) anchor attachment of the C-terminal half of α-agglutinin, GPI anchor attachment of the N-terminal half of a-agglutinin (combined with sulfur bonding to the C-terminal portion), GPI anchoring of the C-terminal region of flocculin Flo1p, and N-terminal anchoring of flocculin Flo1p (without GPI anchoring). The GPI anchor length of the C-terminal region of flocculin Flo1p (SEQ ID NO: 3) may have a length, for example, of 42, 102, 146, 318, 428, and 1326 amino acids. Flo1p is encoded by, for example, the nucleic acid sequence of SEQ ID NO: 13. GPI anchors, which have a conserved core structure of protein-CO—NH—CH$_2$—CH$_2$—PO4-6-mannose (Man)α1,2-Man-α1,6-Man-α1,4-GlcN-α1,6-inositol-PO4-lipid, are discussed in Newman, et al., "Gpi19, the *Saccharomyces cerevisiae* Homologue of Mammalian PIG-P, Is a Subunit of the Initial Enzyme for Glycosylphosphatidylinositol Anchor Biosynthesis," *Eukaryotic Cell,* 4(11): 1801-1807 (2005); Eisenhaber, et al., "Enzymes and Auxiliary Factors for GPI Lipid Anchor Biosynthesis and Post-translational Transfer to Proteins," *BioEssays,* 25: 367-385 (2003); Kinoshita, T. & Inoue, N., "Dissecting and Manipulating the Pathway for Glycosylphosphatidylinositol-anchor Biosynthesis," *Curr. Opin. Chem. Biol.* 4: 632-638 (2000); McConville, M. J. & Menon, A. K., "Recent Developments in the Cell Biology and Biochemistry of Glycosylphosphatidylinositol Lipids," *Mol. Membr. Biol.* 17: 1-17 (2000); Orlean, P., "Biogenesis of Yeast Wall and Surface Components," p. 229-362, in Pringle, et al. (eds.), "Molecular and Cellular Biology of the Yeast *Saccharomyces cerevisiae*" Cold Spring Harbor Press, Cold Spring Harbor, N.Y.; and Tiede, et al., "Biosynthesis of Glycosylphosphatidylinositols in Mammals and Unicellular Microbes," *Biol. Chem.* 380:503-523. (1999).

Other anchoring proteins useful in yeast cells may be used in embodiments of the invention. These include, for example, but are not limited to, C-terminal end fragments of Cwp1p (SEQ ID NO: 14), encoded, for example, by the nucleic acid sequence of SEQ ID NO: 21; Cwp2p (SEQ ID NO: 15), encoded, for example, by the nucleic acid sequence of SEQ ID NO: 22; Tip1p (SEQ ID NO: 16), encoded, for example, by the nucleic acid sequence of SEQ ID NO: 23; Tir1p (SEQ ID NO: 17), encoded, for example, by the nucleic acid sequence of SEQ ID NO: 24; Sed1p (SEQ ID NO: 18), encoded, for example, by the nucleic acid sequence of SEQ ID NO: 38; YCR89-313 (SEQ ID NO: 19), which is a fragment of YCR89 (SEQ ID NO: 25); YCR89-744 (SEQ ID NO:20), Flo1p-344, and Flo1p-596. Methods for use of these anchoring proteins and their efficacy are reported in van der Vaart, J. M., et al., "Comparison of Cell Wall Proteins of *Saccharomyces cerevisiae* as anchors for Cell Surface Expression of Heterologous Proteins," *App. & Env. Microbiol.* 63(2): 615-620 (1997).

III. Receptor Proteins

A wide range of proteins have been reportedly displayed on cell surfaces. These proteins may be displayed outside the cell either by extension through the cell's plasma membrane or by covalent or noncovalent interactions with the cell membrane surface. Typically, yeast cells are armed by expressing a protein on the surface of the cell by fusing the protein with one of the anchoring proteins described above. Although it is not necessary, ideally a gene encoding the fused proteins may be incorporated into the genome of the yeast cell. This incorporation may be accomplished by methods known to those skilled in the art. For example, the yeast cell may be transformed using lithium salt methods, integrative replicative vectors, spheroplasts, a "gene gun," or electroporation.

According to Kondo, supra, proteins that have reportedly been displayed on the surface of yeast cells using α-agglutinin bonding include *Rhizopus oryzae* glucoamylase, *Bacillus stearothermophilus* α-amylase, *Aspergillus aculeatus* β-glucosidase, *Trichoderma reesei* endoglucanase, *Rhizopus oryzae* lipase, and *Aequorea victoria* GFP (including BFP, ECFP, EYFP, Apoaequorin, Hexa-His, ZZ, and Fab fragment of antibody). Proteins displayed using the a-Agglutinin system include single-chain antibodies and single-chain T-cell receptors. Proteins displayed using the C-terminus region of Flo1p include *Rhizopus oryzae* glucoamylase and EGFP. Proteins displayed using the flocculation functional domain of Flo1p include *Rhizopus oryzae* lipase and EGFP. Those skilled in the art will, with the benefit of this disclosure, recognize other proteins that may be displayed.

The identity of a suitable binding ligand will vary depending on the receptor protein exhibited by the catalytic support material. For example, if the catalyst support displays a lectin, an organic catalyst may be modified so that a glycan that bonds with that lectin is attached to a side chain on the catalyst.

The catalyst support may also display one member of an antigen antibody binding pair. The term "antibody" is used herein in the broadest scope to include any protein molecule having a variable region and a constant region where the variable region binds an antigen. Thus, the term antibody includes ScFv molecules of the IgG, IgM, and IgA class, single chain T-cell receptor molecules, as well as multi chain versions of the same linked by disulfide bonds. When the catalyst support includes an anchoring protein fused to an antibody, the antibody is preferably a ScFv., and in most such cases, the ligand will be the corresponding antigen. The antigen will include at least the epitope tag that binds the antibody, and may also contain one or more non epitope regions that can be used to tether the ligand or ligand catalyst pair. Kieke, et al. reports a number of polypeptide sequences that can be used as epitope tags. The proteins reported by Kieke can be fused to surface proteins and bound by antibodies. With the advantage of the disclosure herein, one skilled in the art would note that the antibodies of Kieke could be bound to catalysts and, in turn, tethered to a cell surface that displays those epitope tags.

Those skilled in the art will contemplate other receptor/ligand combinations that may be suitable for use in the invention. These include, for example avidin/biotin and streptavidin/biotin combinations.

A yeast cell expressing a receptor protein could serve as a catalytic support material for any catalyst that could be bound to the ligand designated to bind to the displayed receptor protein. A single yeast line could therefore be used to support, in turn, multiple catalysts.

Biotin/Avidin Interaction

In a preferred embodiment, biotin/avidin binding is used to tether the catalyst to the receptor protein. Biotin/streptavidin binding may also be used. These may be accomplished, for example, by displaying avidin or streptavidin on the surface of a yeast cell as the receptor protein and binding biotin to the catalyst. The cell and the catalyst are mixed, and the strong biotin/avidin or biotin/streptavidin binding interaction tethers the catalyst to the cell.

The biotin/avidin interaction has been extensively studied, as have the procedures and reagents needed for biotinylation. Biotin/avidin chemistry and biotin/streptavidin chemistry, including reagents and methods for biotinylation as well as detection of biotinylated molecules, is discussed in M. D. Savage, et al., "Avidin-Biotin Chemistry: A Handbook" (Pierce Chemical Co., 1992). Creation of metalloenzymes using biotinylated metal catalysts incorporated with streptavidin is reported in Skander, et al., "Chemical Optimization of Artificial Metalloenzymes Based on the Biotin-Avidin Technology: (S)-selective and Solvent-tolerant Hydrogenation Catalysts via the Introduction of Chiral Amino Acid Spacers" *Chem. Commun.*, 4815-4817 (2005).

Biotinylation of proteins (both antigens and antibodies) is used extensively in ELISA/EIA procedures. This extensive use provides a library of methods and reagents for those skilled in the art to determine how to best biotinylate a molecule. With the benefit of this disclosure, those skills may be used to biotinylate catalysts to be tethered to yeast cells. For example, Alpha Diagnostic International reports the following reagents and methods for biotinylation of a protein using long-arm biotin (Aminohexanoyl-biotin N-hydroxysuccinimide). The ADI biotinylation requires at least one free amino group on the biotinylated protein, and ideally the protein is free of amine-containing buffers (such as Tris) to improve coupling efficiency:

Reagents Provided in the ADI Kit:
1. 1 vial of Biotin (10 mg; Cat # 80301)
2. Conjugation Buffer, pH, 8.4, 100 ml, Cat # 80302
3. Stabilizing Buffer; 5 ml., Cat # 80303

Reagents Required But not Provided in the ADI Kit:
1. PBS, pH 7.4 for Dialyzing the conjugate (dissolve 0.26 g KH2PO4, 2.17 g Na2HPO4.7H2O, and 8.71 g of NaCl in 1 L H2O).
2. Dialysis bag (Cut off size <10,000 kDa)
3. DMF for dissolving Biotin Procedure
1. Dialyze the protein to be coupled in 1× conjugation buffer (0.1 M NaHCO3, pH 8.4) extensively. The protein concentration should be 1-10 mg/ml. If the protein is in pure form or in saline or in H2O, it is possible to adjust the pH by adding 10× conjugation buffer and omitting dialysis.
2. Dissolve biotin in DMF at 10 mg/ml before use. Add dissolved biotin protein solution at a predetermined ratio to the protein solution slowly under continuous mixing. A ratio of 1:10 (biotin:protein) may be used for goat or rabbit antibodies. Mix it at room temp. for 1 h or overnight at 4° C.
3. Dialyzed the biotin-conjugate extensively against PBS at 4° C.
4. Add stabilizing buffer to the dialyzed conjugate (add 2 ml for each 500 ul of starting protein volume).
5. The conjugate can be kept at 4° C. for up to 6 months. Avoid freezing and thawing.

A typical nucleic acid sequence encoding avidin is provided in SEQ ID NO: 28. A typical nucleic acid sequence encoding streptavidin is provided in SEQ ID NO: 29. A typical amino acid sequence of avidin is provided in SEQ ID NO: 26. A typical amino acid sequence of streptavidin is provided in SEQ ID NO: 27.

IV. Plasmids

A number of plasmids are suitable for expression of anchoring proteins, receptor proteins and fusions of the same. Many plasmids are also available for integration of the nucleic acids encoding these proteins into the yeast genome and for expression of the coding sequence. Expression plasmids typically contain a promoter element for expression of the nucleic acid encoding the protein. Expression plasmids may also contain signal peptides and transit peptide sequences for fusion to coding sequences so as to direct the expressed protein into the cellular transport machinery for export of the protein to the cell surface. Boder, E. T. & Wittrup, K. D., "Yeast Surface Display for Directed Evolution of Protein Expression, Affinity, and Stability," *Methods in Enzymology,* 25:430-444 (2000) (hereinafter "Boder & Wittrup (II)") reports construction of the pCT302 plasmid. The pCT302 plasmid (shown in FIG. 4) allows expression, of a protein fusion to the Aga2p agglutinin mating protein. Expression is under the control of the GAL 1,10 galactose-inducible promoter. Both the 5' flanking sequence (SEQ ID NO: 4) and 3' flanking sequence (SEQ ID NO: 5) of the promoter have been reported. Boder & Wittrup (II) also reports methods for detection of protein anchored on the cell surface through use of the reported plasmid.

Another plasmid useful for yeast cell surface display is the pYD1 Yeast Display Vector Kit offered by Invitrogen. A map of pYD1 (SEQ ID NO: 6) is included as FIG. 5. The polylinker of pYD1 (SEQ ID NO: 7) is included as FIG. 6, and a restriction map is included as FIG. 7. According to Invitrogen, "pYD1 is a 5.0 kb expression vector designed for expression, secretion, and display of proteins on the extracellular surface of *Saccharomyces cerevisiae* cells. Features of this vector allow regulated expression, secretion, and detection of expressed proteins . . . ". The vector contains the following elements:
- (a) AGA2 gene from *Saccharomyces cerevisiae*. This gene encodes one of the subunits of the a-agglutinin receptor. Fusion of the gene of interest to AGA2 allows secretion and display of the protein of interest.
- (b) GAL1 promoter for regulated expression of the AGA2 gene fusion.
- (c) Xpress™ epitope and V5 epitope for detection of the displayed protein.
- (d) Polyhistidine (6×His) tag for detection and possible purification on metal chelating resin.
- (e) TRPI gene for selection in *Saccharomyces cerevisiae*.
- (f) CEN6/ARS4 for stable, episomal replication in yeast.
- (g) Ampicillin resistance gene and the pUC origin for selection and replication in *E. coli*.

Methods of preparation and use of the pYD1 plasmid are presented in "pYD1 Yeast Display Vector Kit," Catalog No. V835-01, Version D, Dec. 10, 2002, 25-0259, Invitrogen.

V. Catalysts

A variety of catalysts are useful in embodiments of the invention. To be suitable for use in the invention, catalysts should be able to be modified so that they are bound to a ligand that will be tethered (for example, either adsorbed or bound) to a receptor protein, which is in turn anchored to the cell surface. Ideally, catalysts should also not be harmful to or destructive of the yeast cell. Catalysts may be inorganic or organic.

For example, [{N,N'-Bis(3,5-di-tert-butylsalicylidene) 1,2-cyclohexanediaminato(-2-)}cobalt(2)] can be modified so that a glycan is attached on a side chain of the catalyst. The appropriate lectin for this glycan is displayed on the yeast catalyst support. The glycan-bearing cobalt catalyst and the lectin-displaying yeast support are mixed, allowing the cobalt catalyst to adsorb to the yeast support. This immobilizes the cobalt catalyst on the yeast, allowing the cobalt catalyst to be used in oxidation reactions.

A number of useful catalysts for oxidation and reduction reactions may be bound to a ligand and tethered to a cell surface, particularly a yeast cell surface, as taught herein. For example, a catalyst may be a transition metal, a nitroxyl radical, or a supported noble metal. The following supported catalysts may be biotinylated according to methods known to those skilled in the art and set forth herein, then tethered to an avidin- or streptavidin-displaying yeast cell. The yeast cell would act as the support described in each case. Each catalyst is followed by a publication that describes that catalyst: chloromethyl polystyrene resin-1,10-phenanthroline ruthenium (Kang, Q., et al., "Catalytic Oxidation of Alcohols with Polymer-supported Ruthenium Complex under Mild Conditions," *J. Organometallic Chem.*, 26:690 (2005)); poly(ethylene glycol)-supported nitroxyl radicals of the 2,2,6,6-tetramethylpiperidine-1-oxyl (TEMPO) family (Ferreira, P., et al., "Catalytic Oxidation of Alcohols using Molecular Oxygen Mediated by Poly(ethyleneglycol)-supported Nitroxyl Radicals," *Applied Catalysis*, 61:3-4 (2005)) and Ciriminna, et al., "Sol-gel Entrapped TEMPO for the Selective Oxidation of Methyl α-D-glucopyranoside," *Chem. Commun.*, 1441-1442 (2000); Rh6- and Os6-cluster catalysts (Pomogailo, S. I., et al., "Synthesis and Catalytic Properties of Polymer-immobilized Noble Metal Clusters," *PMSE Preprints*, 93:945 (2005)); vanadium catalysts (Kirihara, M., et al., "Aerobic Oxidation catalyzed by Polymer-supported Vanadium Compounds," *ITE Letters*, 5(5): 479-482 (2004); manganese porphyrin (Moghadam, M., et al., "A Convenient Preparation of Polymer-supported Manganese Porphyrin and Its Use as Hydrocarbon Monooxygenation Catalyst," *J. Mol. Catalysis*, 217(1-2): 9-12 (2004); the Co(II) complex of bis(salicylideneethylenediamine) (CoSalen) (Finashina, E. D., et al., "Oxidation of Catecholamines on Chitosan-immobilized Co(II) Salen Complexes," *Macromolecular Symposia*, 204: 205-217 (2003); copper (ii) ions (Owsid, I., et al. "Immobilized Cu(II) Ions as the Oxidation Catalysts," *Zeszyty Naukowe Politechniki Slaskiej, Chemia*, 146:113-116 (2001); homochiral palladium complexes polymeric 2'-,6- and 6'-anchored 2-diphenylphosphino-1-1'-binaphthyl (MOP) ligands (Hocke, H. & Uozumi, Y., "PS-PEG Resin-supported Palladium-MOP Complexes. Application in Asymmetric n-allylic Reduction," *Tetrahedron*, 60(41): 9297-9306 (2004); oxazaborolidine (Franot, C., et al., "A Polymer-bound Oxazaborolidine Catalyst: Enantioselective Borane Reductions of Ketones," *Tetrahedron. Asymmetry*, 6(11):2755-66 (1995).

Multiple catalysts may be tethered to a single cell surface. If the cell bears only a single type of receptor protein, then this may be accomplished by binding each catalyst to identical ligands. For example, if the cell surface displays avidin, then two or more distinct catalysts may be attached to separate biotin molecules. A similar result may be accomplished by expressing more than one kind of receptor protein on the surface of a cell, then providing different catalysts that are bound to different ligands; each ligand may be designed to bind to a different receptor protein.

EXAMPLES

The following examples are intended to guide those skilled in the art in the practice of this invention. They should not be construed to limit the scope of the invention, which is defined by the claims.

Example 1

Example 1 provides amino sulfonamide ruthenium complex oxidation of sec-phenethyl alcohol. The catalyst biotin complex is prepared by a method reported in J. Collot, et al., *J. Am. Chem. Soc.* 125 (2003). This complex is mixed with an avidin displaying yeast in water to prepare the immobilized inorganic catalyst/yeast complex, and the yeast is separated from any unbound catalyst by centrifugation. The oxidations are carried out under the following conditions: nitrogen atmosphere at room temperature for 90 hours: 62.5 millimoles of phenethyl alcohol, and 75 millimoles of tert-butylhydroperoxide are mixed in a mixture of 500 ml of water and 100 ml of acetone. To this mixture is added the immobilized complex which has 0.25 millimoles of the biotin metalloenzyme complex. On completion of the reaction oxidized phenethyl alcohol is observed. The yeast metalloenzyme complex is removed from the reaction mixture by filtration or centrifugation.

Example 2

Example 2 provides biotinylated catalyst synthesis. Biotin (0.1 mol) is dissolved in 90 mL of N,N-dimethylformamide at 60° C. (One synthesis of the amide is reported in S. Amslinger, et al., *Tetrahedron* 60 (2004) 11565-11569.) The solution is then cooled to room temperature and 0.1 mol of N,N'-carbonyldiimidazole is added under nitrogen (approximately 7 hours). Carbon dioxide evolution ceases when the reaction is complete. An equimolar amount (0.1 mol) of the given NH$_2$—R, where R is an appropriate catalytic site, is added in 125 mL of DMF and stirred for 24 hours. For example, the NH$_2$—R compound could be amino-TEMPO (2,2,6,6-Tetramethyl-1-oxy-4-piperidinyl)amine. DMF is then removed under vacuum at 60° C. and the product can then be purified by flash chromatography, column chromatography or recrystallization.

Example 3

Example 3 reports construction of an avidin yeast cell surface display plasmid. Truncated avidin DNA (SEQ ID NO: 41), encoding truncated avidin protein (SEQ ID NO: 42) is made by 30 cycles of PCR amplification using the following primers: Forward, CGAACTGGATCCTCTCCCAGAAA-GTGCTCGCTG (SEQ ID NO: 30) and reverse, CGGATC-CTCGAGTCACTCCTTCTGTGTGCG (SEQ ID NO: 31) using a chicken avidin cDNA clone as a template for PCR. The amplified DNA is cut with BamHI and XhoI and ligated into the vector pYD1 (Invitrogen) cut with BamHI and XhoI.

The resulting clones are transformed into *E. coli* and transformants are isolated and sequenced to verify the proper in frame fusion of avidin and the aga2 protein. A correct construct is then transformed into *Saccharomyces cerevisiae* EBY100 (Invitrogen) using the Invitrogen S.c. EasyComp Kit for preparing competent *S. cerevisiae* cells. The expression of avidin-Aga2 fusion protein is accomplished by growing transformed cells in YNB-CAA medium containing 2% galactose for at least about 4 hours according to the Invitrogen instructions. Cell surface display of the avidin molecule is verified using biotin conjugated with a fluorescence molecule such as Atto 425-biotin, available from Fluka.

Example 4

Example 4 provides TEMPO catalyzed oxidation of glucopyranoside. A tempo/biotin complex is prepared by the method of Example 2. This complex is then mixed with a suspension of yeast cells displaying the avidin protein to form the immobilized Tempo complex; uncomplexed Tempo is separated from the yeast by centrifugation. The complex is mixed with a aqueous solution of alpha methyl glucoside (25 mM) and NaOCl (50 mM) at pH 10 and 2° C. On completion of the reaction, alpha methyl glucuronic acid is observed. The catalyst complex is easily separated from the mixture by centrifugation. Further information on the TEMPO catalyst may be obtained, for example, from R. Ciriminna, et al., "Sol-gel entrapped TEMPO for the selective oxidation of methyl-α-D-glucopyranoside," *J. Chem. Soc., Chem. Comm.*, 1441-1442 (2000).

Example 5

Example 5 presents coupled enzyme reactions. Biotinylated forms of glucose oxidase and catalase are prepared as discussed above. These are mixed in a ratio of 6 IU of catalase to 1 IU of glucose oxidase. Yeast cells displaying avidin are added to this mixture in an amount that absorbs all of the enzymatic activities. The catalytic complex is added to a 10% dextrose solution with the pH controlled at 6.0 at about 25° C. Aeration is applied for about 24 hours. Upon completion of this reaction gluconic acid is observed and all of the hydrogen peroxide produced during the reaction will have been degraded by the catalase. The catalyst complexes are easily recovered by filtration.

Further guidance on enzyme behavior and catalyst creation in general may be obtained from M. T. Reetz, "Controlling the Enantioselectivity of Enzymes by Directed Evolution: Practical and Theoretical Ramifications," *Proc. Natl. Acad. Sci. U.S.A.*, 101: 5716-5722 (2004), Wilson, M. E. and Whitesides, G. M., "Conversion of a Protein to a Homogeneous Asymmetric Hydrogenation Catalyst by Site-Specific Modification with a Diphosphinerhodium(I) Moiety", *J. Am. Chem. Soc.*, 100: 306-307 (1978); and C. M. Thomas, et al., "Aqueous Oxidation of Alcohols Catalyzed by Artificial Metalloenzymes based on the Biotin-Avidin Technology," *J. Organomet. Chem.*, 690: 4488 (2005).

Example 6

Example 6 presents construction of a T7 bacteriophage with streptavidin displayed on its surface. Truncated streptavidin DNA (SEQ ID NO: 43), encoding truncated streptavidin protein (SEQ ID NO: 44), is made by 30 cycles of PCR amplification using the following primers: forward, GCGAATTCAGACCCCTCCAAGGACTCG (SEQ ID NO: 32) and reverse, GCAAGCTTCTACTGCTGAACGGCGTC (SEQ ID NO: 33) and using *Streptomyces avidinii* (ATCC 27419D) genomic DNA as a template.

The amplified DNA is cut with EcoRI and HindIII and ligated into Novagen's T7Select 10-3b EcoRI/HindIII vector arms supplied in the T7Select Cloning Kit from Novagen. The ligation reactions are added to the T7 packaging extracts for in vitro packaging according to the procedure supplied by Novagen. Various clones are selected for sequencing and ones that had the proper fusion of the streptavidin gene to the T7 capsid protein 10B are selected for further work. Correct T7 phage with avidin displayed on their surface were amplied and phage particles recovered.

Example 7

Example 7 reports construction of a plasmid for display of streptavidin on the cell surface of a strain of *E. coli* A truncated fadL gene (SEQ ID NO: 40) is cloned by PCR amplification using the following primers: forward, GGAAT-TCATGGTCATGAGCCAGAAAACC (SEQ ID NO: 34) and reverse, GCTCTAGAACGATTCTGTGCAGGAAC (SEQ ID NO: 35), and using *E. coli* genomic DNA (ATCC 700926D).

This PCR product is cut with EcoRI and XbaI and cloned into pTrc99A cut with EcoRI and XbaI to make a plasmid called pTrcFadL. The streptavidin DNA is made by PCR using the following primers: forward, GCTCTAGAGAC-CCCTCCAAGGACTCG (SEQ ID NO: 36), and reverse, GCAAGCTTCTACTGCTGAACGGCGTC (SEQ ID NO: 33) and using *Streptomyces avidinii* (ATCC 27419D) genomic DNA as a template.

The streptavidin DNA is cut with XbaI and HindIII and ligated into pTrcFadL digested with XbaI and HindIII. This produces a plasmid called pTrcFadL-streptavidin (SEQ ID NO: 37) which is an inframe fusion of the fadL gene product (SEQ ID NO: 40) and the streptavidin protein. The plasmid is transformed into TOP10 *E. coli* competent cells (Invitrogen) and selected on LB with ampicillin (100 mg/l). Individual colonies are tested to determine if the expression of the steptavidin on the cell surface is achieved by growing the transformed cells in LB with ampicillin (50 mg/l) and isopropyl β-D-1 thiogalactopyranoside (IPTG).

The cell surface display of the streptavidin molecule is verified using biotin conjugated with a fluorescence molecule such as Atto 425-biotin (available from Fluka). Correct *E. coli* with streptavidin displayed on the cell surface is grown in the presence of ampicillin (50 mg/l) and various concentrations of IPTG to make cells with streptavidin displayed on their cell surface.

The start codon of the truncated fadL gene used herein begins at base 8 of SEQ ID NO: 39. Avidin and streptavidin used in this and other examples are truncated due to the removal of peptide leader sequences. One skilled in the art would recognize, based on the PCR primer sequences, that these proteins would be produced in truncated form.

Whereas particular embodiments of this invention have been described for purposes of illustration, it will be evident to those persons skilled in the art that numerous variations of the details of the present teaching may be made without departing from the invention as defined in the appended claims. Those patents and publications discussed herein should be viewed as indicative of the level of skill in the art, though no admission is made that any document is a prior art reference. All of the foregoing patents and publications discussed herein are hereby incorporated by reference.

I claim:

1. A composition consisting of a yeast catalytic support with anchored receptor proteins uniformly displayed on the yeast cell support surface selected from the group consisting of avidin and streptavidin wherein bound to the anchored receptor protein is a ligand which is biotin; and a non-biological catalyst bound to the biotin selected from the group consisting of TEMPO, and [{N,N'-Bis(3,5-di-tert-butylsalicylidene)1,2-cyclohexanediaminato(-2-)}cobalt(2)].

2. The composition of claim 1-wherein yeast cell is a strain of *Saccharomyces cerevisiae*.

3. The composition of claim 1 wherein said receptor protein is anchored by being fused to an anchoring protein disposed on the yeast surface, wherein said anchoring protein comprises polypeptide components selected from the group consisting of a glycosylphosphatidylinositol (GPI) anchor fused to a-agglutinin; a GPI anchor fused to an N-terminal region of a-agglutinin combined with disulfide bonding of a C-terminal region of α-agglutinin on the cell surface; a GPI-anchor fused to a C-terminal region of Flo1p; and a N-terminal anchoring of the flocculation functional domain of Flo1p without GPI.

4. A method for catalyzing a chemical reaction comprising contacting a reactant for the reaction with the composition of claim 1; separating the catalyst composition from the reactant; and observing the catalyzed reactant.

5. A method for making the composition of claim 1 comprising forming a recombinant nucleic acid encoding the receptor protein selected from said avidin and streptavidin fused in-frame to a nucleic acid encoding an anchoring protein to form a fusion protein when expressed in the yeast; growing the yeast to express said fusion protein in the yeast and display the receptor protein on the yeast cell support surface; binding the biotin to the receptor protein; and linking said non-biological catalyst to the biotin.

6. The method of claim 5 including wherein said is anchoring protein comprises polypeptide components selected from the group consisting of a glycosylphosphatidylinositol (GPI) anchor fused to a-agglutinin; a GPI anchor fused to a N-terminal region of a-agglutinin combined with disulfide bonding of a C-terminal region of α-agglutinin on the cell surface; a GPI-anchor fused to a C-terminal region of Flo1p;

and a N-terminal anchoring of the flocculation functional domain of Flo1p without GPI.

7. The method of claim 5 including wherein said nucleic acid encoding said anchoring protein is operably configured with a promoter sequence to express said fusion protein in the yeast cell and said nucleic acid encoding the anchoring protein includes transport sequence encoding a peptide domain operable to transport the anchoring protein fused to the receptor protein to the surface of the yeast cell.

8. The method of claim 5 including wherein the recombinant nucleic acid is integrated into a chromosome of the cell.

* * * * *

SEQUENCE LISTING

```
<160> NUMBER OF SEQ ID NOS: 44

<210> SEQ ID NO 1
<211> LENGTH: 650
<212> TYPE: PRT
<213> ORGANISM: Saccharomyces cerevisiae

<400> SEQUENCE: 1

Met Phe Thr Phe Leu Lys Ile Ile Leu Trp Leu Phe Ser Leu Ala Leu
1               5                   10                  15

Ala Ser Ala Ile Asn Ile Asn Asp Ile Thr Phe Ser Asn Leu Glu Ile
            20                  25                  30

Thr Pro Leu Thr Ala Asn Lys Gln Pro Asp Gln Gly Trp Thr Ala Thr
        35                  40                  45

Phe Asp Phe Ser Ile Ala Asp Ala Ser Ser Ile Arg Glu Gly Asp Glu
    50                  55                  60

Phe Thr Leu Ser Met Pro His Val Tyr Arg Ile Lys Leu Leu Asn Ser
65                  70                  75                  80

Ser Gln Thr Ala Thr Ile Ser Leu Ala Asp Gly Thr Glu Ala Phe Lys
                85                  90                  95

Cys Tyr Val Ser Gln Gln Ala Ala Tyr Leu Tyr Glu Asn Thr Thr Phe
            100                 105                 110

Thr Cys Thr Ala Gln Asn Asp Leu Ser Ser Tyr Asn Thr Ile Asp Gly
        115                 120                 125

Ser Ile Thr Phe Ser Leu Asn Phe Ser Asp Gly Gly Ser Ser Tyr Glu
    130                 135                 140

Tyr Glu Leu Glu Asn Ala Lys Phe Phe Lys Ser Gly Pro Met Leu Val
145                 150                 155                 160

Lys Leu Gly Asn Gln Met Ser Asp Val Val Asn Phe Asp Pro Ala Ala
                165                 170                 175

Phe Thr Glu Asn Val Phe His Ser Gly Arg Ser Thr Gly Tyr Gly Ser
            180                 185                 190

Phe Glu Ser Tyr His Leu Gly Met Tyr Cys Pro Asn Gly Tyr Phe Leu
        195                 200                 205

Gly Gly Thr Glu Lys Ile Asp Tyr Asp Ser Ser Asn Asn Asn Val Asp
    210                 215                 220

Leu Asp Cys Ser Ser Val Gln Val Tyr Ser Ser Asn Asp Phe Asn Asp
225                 230                 235                 240

Trp Trp Phe Pro Gln Ser Tyr Asn Asp Thr Asn Ala Asp Val Thr Cys
                245                 250                 255

Phe Gly Ser Asn Leu Trp Ile Thr Leu Asp Glu Lys Leu Tyr Asp Gly
            260                 265                 270

Glu Met Leu Trp Val Asn Ala Leu Gln Ser Leu Pro Ala Asn Val Asn
        275                 280                 285
```

```
Thr Ile Asp His Ala Leu Glu Phe Gln Tyr Thr Cys Leu Asp Thr Ile
        290                 295                 300

Ala Asn Thr Thr Tyr Ala Thr Gln Phe Ser Thr Thr Arg Glu Phe Ile
305                 310                 315                 320

Val Tyr Gln Gly Arg Asn Leu Gly Thr Ala Ser Ala Lys Ser Ser Phe
                325                 330                 335

Ile Ser Thr Thr Thr Asp Leu Thr Ser Ile Asn Thr Ser Ala Tyr
                340                 345                 350

Ser Thr Gly Ser Ile Ser Thr Val Glu Thr Gly Asn Arg Thr Thr Ser
            355                 360                 365

Glu Val Ile Ser His Val Val Thr Thr Ser Thr Lys Leu Ser Pro Thr
        370                 375                 380

Ala Thr Thr Ser Leu Thr Ile Ala Gln Thr Ser Ile Tyr Ser Thr Asp
385                 390                 395                 400

Ser Asn Ile Thr Val Gly Thr Asp Ile His Thr Thr Ser Glu Val Ile
                405                 410                 415

Ser Asp Val Glu Thr Ile Ser Arg Glu Thr Ala Ser Thr Val Val Ala
                420                 425                 430

Ala Pro Thr Ser Thr Thr Gly Trp Thr Gly Ala Met Asn Thr Tyr Ile
                435                 440                 445

Ser Gln Phe Thr Ser Ser Ser Phe Ala Thr Ile Asn Ser Thr Pro Ile
            450                 455                 460

Ile Ser Ser Ser Ala Val Phe Glu Thr Ser Asp Ala Ser Ile Val Asn
465                 470                 475                 480

Val His Thr Glu Asn Ile Thr Asn Thr Ala Ala Val Pro Ser Glu Glu
                485                 490                 495

Pro Thr Phe Val Asn Ala Thr Arg Asn Ser Leu Asn Ser Phe Cys Ser
            500                 505                 510

Ser Lys Gln Pro Ser Ser Pro Ser Ser Tyr Thr Ser Ser Pro Leu Val
        515                 520                 525

Ser Ser Leu Ser Val Ser Lys Thr Leu Leu Ser Thr Ser Phe Thr Pro
    530                 535                 540

Ser Val Pro Thr Ser Asn Thr Tyr Ile Lys Thr Lys Asn Thr Gly Tyr
545                 550                 555                 560

Phe Glu His Thr Ala Leu Thr Thr Ser Ser Val Gly Leu Asn Ser Phe
                565                 570                 575

Ser Glu Thr Ala Val Ser Ser Gln Gly Thr Lys Ile Asp Thr Phe Leu
            580                 585                 590

Val Ser Ser Leu Ile Ala Tyr Pro Ser Ser Ala Ser Gly Ser Gln Leu
    595                 600                 605

Ser Gly Ile Gln Gln Asn Phe Thr Ser Thr Ser Leu Met Ile Ser Thr
610                 615                 620

Tyr Glu Gly Lys Ala Ser Ile Phe Phe Ser Ala Glu Leu Gly Ser Ile
625                 630                 635                 640

Ile Phe Leu Leu Leu Ser Tyr Leu Leu Phe
                645                 650

<210> SEQ ID NO 2
<211> LENGTH: 725
<212> TYPE: PRT
<213> ORGANISM: Saccharomyces cerevisiae
```

```
<400> SEQUENCE: 2

Met Thr Leu Ser Phe Ala His Phe Thr Tyr Leu Phe Thr Ile Leu Leu
1               5                   10                  15

Gly Leu Thr Asn Ile Ala Leu Ala Ser Asp Pro Glu Thr Ile Leu Val
            20                  25                  30

Thr Ile Thr Lys Thr Asn Asp Ala Asn Gly Val Val Thr Thr Thr Val
        35                  40                  45

Ser Pro Ala Leu Val Ser Ser Thr Ile Val Gln Ala Gly Thr Thr
    50                  55                  60

Thr Leu Tyr Thr Thr Trp Cys Pro Leu Thr Val Ser Thr Ser Ser Ala
65                  70                  75                  80

Ala Glu Ile Ser Pro Ser Ile Ser Tyr Ala Thr Thr Leu Ser Arg Phe
                85                  90                  95

Ser Thr Leu Thr Leu Ser Thr Glu Val Cys Ser His Glu Ala Cys Pro
                100                 105                 110

Ser Ser Ser Thr Leu Pro Thr Thr Thr Leu Ser Val Thr Ser Lys Phe
            115                 120                 125

Thr Ser Tyr Ile Cys Pro Thr Cys His Thr Thr Ala Ile Ser Ser Leu
130                 135                 140

Ser Glu Val Gly Thr Thr Thr Val Val Ser Ser Ser Ala Ile Glu Pro
145                 150                 155                 160

Ser Ser Ala Ser Ile Ile Ser Pro Val Thr Ser Thr Leu Ser Ser Thr
                165                 170                 175

Thr Ser Ser Asn Pro Thr Thr Thr Ser Leu Ser Ser Thr Ser Thr Ser
            180                 185                 190

Pro Ser Ser Thr Ser Thr Ser Pro Ser Ser Thr Ser Thr Ser Ser Ser
        195                 200                 205

Ser Thr Ser Thr Ser Ser Ser Ser Thr Ser Thr Ser Ser Ser Ser Thr
210                 215                 220

Ser Thr Ser Pro Ser Ser Thr Ser Thr Ser Ser Ser Leu Thr Ser Thr
225                 230                 235                 240

Ser Ser Ser Ser Thr Ser Thr Ser Gln Ser Ser Thr Ser Thr Ser Ser
                245                 250                 255

Ser Ser Thr Ser Thr Ser Pro Ser Ser Thr Ser Thr Ser Ser Ser Ser
            260                 265                 270

Thr Ser Thr Ser Pro Ser Ser Lys Ser Thr Ser Ala Ser Ser Thr Ser
        275                 280                 285

Thr Ser Ser Tyr Ser Thr Ser Thr Ser Pro Ser Leu Thr Ser Ser Ser
        290                 295                 300

Pro Thr Leu Ala Ser Thr Ser Pro Ser Ser Thr Ser Ile Ser Ser Thr
305                 310                 315                 320

Phe Thr Asp Ser Thr Ser Ser Leu Gly Ser Ser Ile Ala Ser Ser Ser
                325                 330                 335

Thr Ser Val Ser Leu Tyr Ser Pro Ser Thr Pro Val Tyr Ser Val Pro
            340                 345                 350

Ser Thr Ser Ser Asn Val Ala Thr Pro Ser Met Thr Ser Ser Thr Val
        355                 360                 365

Glu Thr Val Ser Ser Gln Ser Ser Ser Glu Tyr Ile Thr Lys Ser
        370                 375                 380

Ser Ile Ser Thr Thr Ile Pro Ser Phe Ser Met Ser Thr Tyr Phe Thr
385                 390                 395                 400

Thr Val Ser Gly Val Thr Thr Met Tyr Thr Thr Trp Cys Pro Tyr Ser
                405                 410                 415
```

```
Ser Glu Ser Glu Thr Ser Thr Leu Thr Ser Met His Glu Thr Val Thr
                420                 425                 430

Thr Asp Ala Thr Val Cys Thr His Glu Ser Cys Met Pro Ser Gln Thr
            435                 440                 445

Thr Ser Leu Ile Thr Ser Ser Ile Lys Met Ser Thr Lys Asn Val Ala
        450                 455                 460

Thr Ser Val Ser Thr Ser Thr Val Glu Ser Ser Tyr Ala Cys Ser Thr
465                 470                 475                 480

Cys Ala Glu Thr Ser His Ser Tyr Ser Ser Val Gln Thr Ala Ser Ser
                485                 490                 495

Ser Ser Val Thr Gln Gln Thr Thr Ser Thr Lys Ser Trp Val Ser Ser
                500                 505                 510

Met Thr Thr Ser Asp Glu Asp Phe Asn Lys His Ala Thr Gly Lys Tyr
            515                 520                 525

His Val Thr Ser Ser Gly Thr Ser Thr Ile Ser Thr Ser Val Ser Glu
        530                 535                 540

Ala Thr Ser Thr Ser Ser Ile Asp Ser Glu Ser Gln Glu Gln Ser Ser
545                 550                 555                 560

His Leu Leu Ser Thr Ser Val Leu Ser Ser Ser Leu Ser Ala Thr
                565                 570                 575

Leu Ser Ser Asp Ser Thr Ile Leu Leu Phe Ser Ser Val Ser Ser Leu
            580                 585                 590

Ser Val Glu Gln Ser Pro Val Thr Thr Leu Gln Ile Ser Ser Thr Ser
                595                 600                 605

Glu Ile Leu Gln Pro Thr Ser Ser Thr Ala Ile Ala Thr Ile Ser Ala
            610                 615                 620

Ser Thr Ser Ser Leu Ser Ala Thr Ser Ile Ser Thr Pro Ser Thr Ser
625                 630                 635                 640

Val Glu Ser Thr Ile Glu Ser Ser Ser Leu Thr Pro Thr Val Ser Ser
                645                 650                 655

Ile Phe Leu Ser Ser Ser Ser Ala Pro Ser Ser Leu Gln Thr Ser Val
            660                 665                 670

Thr Thr Thr Glu Val Ser Thr Thr Ser Ile Ser Ile Gln Tyr Gln Thr
                675                 680                 685

Ser Ser Met Val Thr Ile Ser Gln Tyr Met Gly Ser Gly Ser Gln Thr
        690                 695                 700

Arg Leu Pro Leu Gly Lys Leu Val Phe Ala Ile Met Ala Val Ala Cys
705                 710                 715                 720

Asn Val Ile Phe Ser
                725

<210> SEQ ID NO 3
<211> LENGTH: 1537
<212> TYPE: PRT
<213> ORGANISM: Saccharomyces cerevisiae

<400> SEQUENCE: 3

Met Thr Met Pro His Arg Tyr Met Phe Leu Ala Val Phe Thr Leu Leu
1               5                   10                  15

Ala Leu Thr Ser Val Ala Ser Gly Ala Thr Glu Ala Cys Leu Pro Ala
                20                  25                  30

Gly Gln Arg Lys Ser Gly Met Asn Ile Asn Phe Tyr Gln Tyr Ser Leu
            35                  40                  45

Lys Asp Ser Ser Thr Tyr Ser Asn Ala Ala Tyr Met Ala Tyr Gly Tyr
        50                  55                  60
```

```
Ala Ser Lys Thr Lys Leu Gly Ser Val Gly Gln Thr Asp Ile Ser
 65              70                  75                  80

Ile Asp Tyr Asn Ile Pro Cys Val Ser Ser Gly Thr Phe Pro Cys
                 85                  90                  95

Pro Gln Glu Asp Ser Tyr Gly Asn Trp Gly Cys Lys Gly Met Gly Ala
            100                 105                 110

Cys Ser Asn Ser Gln Gly Ile Ala Tyr Trp Ser Thr Asp Leu Phe Gly
            115                 120                 125

Phe Tyr Thr Thr Pro Thr Asn Val Thr Leu Glu Met Thr Gly Tyr Phe
        130                 135                 140

Leu Pro Pro Gln Thr Gly Ser Tyr Thr Phe Lys Phe Ala Thr Val Asp
145                 150                 155                 160

Asp Ser Ala Ile Leu Ser Val Gly Gly Ala Thr Ala Phe Asn Cys Cys
                165                 170                 175

Ala Gln Gln Gln Pro Pro Ile Thr Ser Thr Asn Phe Thr Ile Asp Gly
            180                 185                 190

Ile Lys Pro Trp Gly Gly Ser Leu Pro Pro Asn Ile Glu Gly Thr Val
        195                 200                 205

Tyr Met Tyr Ala Gly Tyr Tyr Tyr Pro Met Lys Val Val Tyr Ser Asn
210                 215                 220

Ala Val Ser Trp Gly Thr Leu Pro Ile Ser Val Thr Leu Pro Asp Gly
225                 230                 235                 240

Thr Thr Val Ser Asp Asp Phe Glu Gly Tyr Val Tyr Ser Phe Asp Asp
                245                 250                 255

Asp Leu Ser Gln Ser Asn Cys Thr Val Pro Asp Pro Ser Asn Tyr Ala
            260                 265                 270

Val Ser Thr Thr Thr Thr Thr Thr Glu Pro Trp Thr Gly Thr Phe Thr
        275                 280                 285

Ser Thr Ser Thr Glu Met Thr Thr Val Thr Gly Thr Asn Gly Val Pro
        290                 295                 300

Thr Asp Glu Thr Val Ile Val Ile Arg Thr Pro Thr Thr Ala Ser Thr
305                 310                 315                 320

Ile Ile Thr Thr Thr Glu Pro Trp Asn Ser Thr Phe Thr Ser Thr Ser
                325                 330                 335

Thr Glu Leu Thr Thr Val Thr Gly Thr Asn Gly Val Arg Thr Asp Glu
            340                 345                 350

Thr Ile Ile Val Ile Arg Thr Pro Thr Thr Ala Thr Ala Ile Thr
        355                 360                 365

Thr Thr Glu Pro Trp Asn Ser Thr Phe Thr Ser Thr Ser Thr Glu Leu
        370                 375                 380

Thr Thr Val Thr Gly Thr Asn Gly Leu Pro Thr Asp Glu Thr Ile Ile
385                 390                 395                 400

Val Ile Arg Thr Pro Thr Thr Ala Thr Ala Met Thr Thr Gln
            405                 410                 415

Pro Trp Asn Asp Thr Phe Thr Ser Thr Ser Thr Glu Leu Thr Thr Val
            420                 425                 430

Thr Gly Thr Asn Gly Leu Pro Thr Asp Glu Thr Ile Ile Val Ile Arg
        435                 440                 445

Thr Pro Thr Thr Ala Thr Ala Met Thr Thr Gln Pro Trp Asn
450                 455                 460

Asp Thr Phe Thr Ser Thr Ser Thr Glu Leu Thr Thr Val Thr Gly Thr
465                 470                 475                 480

Asn Gly Leu Pro Thr Asp Glu Thr Ile Ile Val Ile Arg Thr Pro Thr
            485                 490                 495
```

```
Thr Ala Thr Thr Ala Met Thr Thr Gln Pro Trp Asn Asp Thr Phe
            500                 505                 510

Thr Ser Thr Ser Thr Glu Ile Thr Val Thr Gly Thr Asn Gly Leu
            515                 520                 525

Pro Thr Asp Glu Thr Ile Ile Val Ile Arg Pro Thr Thr Ala Thr
530                 535                 540

Thr Ala Met Thr Thr Pro Gln Pro Trp Asn Asp Thr Phe Thr Ser Thr
545                 550                 555                 560

Ser Thr Glu Met Thr Thr Val Thr Gly Thr Asn Gly Leu Pro Thr Asp
                565                 570                 575

Glu Thr Ile Ile Val Ile Arg Thr Pro Thr Thr Ala Thr Ala Ile
            580                 585                 590

Thr Thr Thr Glu Pro Trp Asn Ser Thr Phe Thr Ser Thr Ser Thr Glu
            595                 600                 605

Met Thr Thr Val Thr Gly Thr Asn Gly Leu Pro Thr Asp Glu Thr Ile
            610                 615                 620

Ile Val Ile Arg Thr Pro Thr Thr Ala Thr Ala Ile Thr Thr Thr
625                 630                 635                 640

Gln Pro Trp Asn Asp Thr Phe Thr Ser Thr Ser Thr Glu Met Thr Thr
                645                 650                 655

Val Thr Gly Thr Asn Gly Leu Pro Thr Asp Glu Thr Ile Ile Val Ile
            660                 665                 670

Arg Thr Pro Thr Thr Ala Thr Thr Ala Met Thr Thr Gln Pro Trp
            675                 680                 685

Asn Asp Thr Phe Thr Ser Thr Ser Thr Glu Ile Thr Val Thr Gly
            690                 695                 700

Thr Thr Gly Leu Pro Thr Asp Glu Thr Ile Ile Val Ile Arg Thr Pro
705                 710                 715                 720

Thr Thr Ala Thr Thr Ala Met Thr Thr Gln Pro Trp Asn Asp Thr
            725                 730                 735

Phe Thr Ser Thr Ser Thr Glu Met Thr Thr Val Thr Gly Thr Asn Gly
            740                 745                 750

Val Pro Thr Asp Glu Thr Val Ile Val Ile Arg Thr Pro Thr Ser Glu
            755                 760                 765

Gly Leu Ile Ser Thr Thr Glu Pro Trp Thr Gly Thr Phe Thr Ser
770                 775                 780

Thr Ser Thr Glu Met Thr Thr Val Thr Gly Thr Asn Gly Gln Pro Thr
785                 790                 795                 800

Asp Glu Thr Val Ile Val Ile Arg Thr Pro Thr Ser Glu Gly Leu Val
            805                 810                 815

Thr Thr Thr Thr Glu Pro Trp Thr Gly Thr Phe Thr Ser Thr Ser Thr
            820                 825                 830

Glu Met Thr Thr Ile Thr Gly Thr Asn Gly Val Pro Thr Asp Glu Thr
            835                 840                 845

Val Ile Val Ile Arg Thr Pro Thr Ser Glu Gly Leu Ile Ser Thr Thr
850                 855                 860

Thr Glu Pro Trp Thr Gly Thr Phe Thr Ser Thr Ser Thr Glu Met Thr
865                 870                 875                 880

Thr Ile Thr Gly Thr Asn Gly Gln Pro Thr Asp Glu Thr Val Ile Val
            885                 890                 895

Ile Arg Thr Pro Thr Ser Glu Gly Leu Ile Ser Thr Thr Glu Pro
            900                 905                 910

Trp Thr Gly Thr Phe Thr Ser Thr Ser Thr Glu Met Thr His Val Thr
            915                 920                 925
```

-continued

```
Gly Thr Asn Gly Val Pro Thr Asp Glu Thr Val Ile Val Ile Arg Thr
930                 935                 940

Pro Thr Ser Glu Gly Leu Ile Ser Thr Thr Thr Glu Pro Trp Thr Gly
945                 950                 955                 960

Thr Phe Thr Ser Thr Ser Thr Glu Val Thr Ile Thr Gly Thr Asn
                965                 970                 975

Gly Gln Pro Thr Asp Glu Thr Val Ile Val Ile Arg Thr Pro Thr Ser
                980                 985                 990

Glu Gly Leu Ile Ser Thr Thr Thr Glu Pro Trp Thr Gly Thr Phe Thr
            995                 1000                1005

Ser Thr Ser Thr Glu Met Thr Thr Val Thr Gly Thr Asn Gly Gln
    1010                1015                1020

Pro Thr Asp Glu Thr Val Ile Val Ile Arg Thr Pro Thr Ser Glu
    1025                1030                1035

Gly Leu Val Thr Thr Thr Thr Glu Pro Trp Thr Gly Thr Phe Thr
    1040                1045                1050

Ser Thr Ser Thr Glu Met Ser Thr Val Thr Gly Thr Asn Gly Leu
    1055                1060                1065

Pro Thr Asp Glu Thr Val Ile Val Val Lys Thr Pro Thr Thr Ala
    1070                1075                1080

Ile Ser Ser Ser Leu Ser Ser Ser Ser Ser Gly Gln Ile Thr Ser
    1085                1090                1095

Ser Ile Thr Ser Ser Arg Pro Ile Ile Thr Pro Phe Tyr Pro Ser
    1100                1105                1110

Asn Gly Thr Ser Val Ile Ser Ser Ser Val Ile Ser Ser Ser Val
    1115                1120                1125

Thr Ser Ser Leu Phe Thr Ser Ser Pro Val Ile Ser Ser Ser Val
    1130                1135                1140

Ile Ser Ser Ser Thr Thr Thr Ser Thr Ser Ile Phe Ser Glu Ser
    1145                1150                1155

Ser Lys Ser Ser Val Ile Pro Thr Ser Ser Thr Ser Gly Ser
    1160                1165                1170

Ser Glu Ser Glu Thr Ser Ser Ala Gly Ser Val Ser Ser Ser Ser
    1175                1180                1185

Phe Ile Ser Ser Glu Ser Ser Lys Ser Pro Thr Tyr Ser Ser Ser
    1190                1195                1200

Ser Leu Pro Leu Val Thr Ser Ala Thr Thr Ser Gln Glu Thr Ala
    1205                1210                1215

Ser Ser Leu Pro Pro Ala Thr Thr Thr Lys Thr Ser Glu Gln Thr
    1220                1225                1230

Thr Leu Val Thr Val Thr Ser Cys Glu Ser His Val Cys Thr Glu
    1235                1240                1245

Ser Ile Ser Pro Ala Ile Val Ser Thr Ala Thr Val Thr Val Ser
    1250                1255                1260

Gly Val Thr Thr Glu Tyr Thr Thr Trp Cys Pro Ile Ser Thr Thr
    1265                1270                1275

Glu Thr Thr Lys Gln Thr Lys Gly Thr Thr Glu Gln Thr Thr Glu
    1280                1285                1290

Thr Thr Lys Gln Thr Thr Val Val Thr Ile Ser Ser Cys Glu Ser
    1295                1300                1305

Asp Val Cys Ser Lys Thr Ala Ser Pro Ala Ile Val Ser Thr Ser
    1310                1315                1320

Thr Ala Thr Ile Asn Gly Val Thr Thr Glu Tyr Thr Thr Trp Cys
    1325                1330                1335
```

| | | | | | | | | | | | |
|---|---|---|---|---|---|---|---|---|---|---|---|
| Pro | Ile | Ser | Thr | Thr | Glu | Ser | Arg | Gln | Gln | Thr | Thr | Leu | Val | Thr |
| | | 1340 | | | | 1345 | | | | 1350 | |

Pro Ile Ser Thr Thr Glu Ser Arg Gln Gln Thr Thr Leu Val Thr
          1340                1345                1350

Val Thr Ser Cys Glu Ser Gly Val Cys Ser Glu Thr Ala Ser Pro
    1355                1360                1365

Ala Ile Val Ser Thr Ala Thr Ala Thr Val Asn Asp Val Val Thr
    1370                1375                1380

Val Tyr Pro Thr Trp Arg Pro Gln Thr Ala Asn Glu Glu Ser Val
    1385                1390                1395

Ser Ser Lys Met Asn Ser Ala Thr Gly Glu Thr Thr Thr Asn Thr
    1400                1405                1410

Leu Ala Ala Glu Thr Thr Thr Asn Thr Val Ala Ala Glu Thr Ile
    1415                1420                1425

Thr Asn Thr Gly Ala Ala Glu Thr Lys Thr Val Val Thr Ser Ser
    1430                1435                1440

Leu Ser Arg Ser Asn His Ala Glu Thr Gln Thr Ala Ser Ala Thr
    1445                1450                1455

Asp Val Ile Gly His Ser Ser Ser Val Val Ser Val Ser Glu Thr
    1460                1465                1470

Gly Asn Thr Lys Ser Leu Thr Ser Ser Gly Leu Ser Thr Met Ser
    1475                1480                1485

Gln Gln Pro Arg Ser Thr Pro Ala Ser Ser Met Val Gly Tyr Ser
    1490                1495                1500

Thr Ala Ser Leu Glu Ile Ser Thr Tyr Ala Gly Ser Ala Asn Ser
    1505                1510                1515

Leu Leu Ala Gly Ser Gly Leu Ser Val Phe Ile Ala Ser Leu Leu
    1520                1525                1530

Leu Ala Ile Ile
    1535

<210> SEQ ID NO 4
<211> LENGTH: 180
<212> TYPE: DNA
<213> ORGANISM: Artificial Sequence
<220> FEATURE:
<223> OTHER INFORMATION: Plasmid

<400> SEQUENCE: 4
ataaacacac agtatgtttt taaggacaat agctcgacga ttgaaggtag atacccatac      60
gacgttccag actacgctct gcaggctagt ggtggtggtg gttctggtgg tggtggttct    120
ggtggtggtg gttctgctag cgacgtcgtt atgactcaaa caccactatc acttcctgtt    180

<210> SEQ ID NO 5
<211> LENGTH: 51
<212> TYPE: DNA
<213> ORGANISM: Artificial Sequence
<220> FEATURE:
<223> OTHER INFORMATION: Plasmid

<400> SEQUENCE: 5
tcctcagaac aaaagcttat ttctgaagaa gacttgtaat agctcgagat c              51

<210> SEQ ID NO 6
<211> LENGTH: 5009
<212> TYPE: DNA
<213> ORGANISM: Artificial Sequence
<220> FEATURE:
<223> OTHER INFORMATION: Plasmid

```
<400> SEQUENCE: 6
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caatgtaat aaaagtatca acaaaaaatt gttaatatac      420
ctctatactt taacgtcaag gagaaaaaac cccggatcgg actactagca gctgtaatac     480
gactcactat agggaatatt aagctaattc tacttcatac attttcaatt aagatgcagt     540
tacttcgctg tttttcaata ttttctgtta ttgcttcagt tttagcacag gaactgacaa     600
ctatatgcga gcaaatcccc tcaccaactt tagaatcgac gccgtactct tgtcaacga     660 ctactatttt ggccaacggg aaggcaatgc aaggagtttt tgaatattac aaatcagtaa     720 cgttgtcag taattgcggt tctcacccct caacaactag caaaggcagc cccataaaca      780
cacagtatgt ttttaagctt ctgcaggcta gtggtggtgg tggttctggt ggtggtggtt     840
ctggtggtgg tggttctgct agcatgactg gtggacagca aatgggtcgg gatctgtacg     900
acgatgacga taaggtacca ggatccagtg tggtggaatt ctgcagatat ccagcacagt     960
ggcggccgct cgagtctaga gggcccttcg aaggtaagcc tatccctaac cctctcctcg    1020
gtctcgattc tacgcgtacc ggtcatcatc accatcacca ttgagtttaa acccgctgat    1080
ctgataacaa cagtgtagat gtaacaaaat cgactttgtt cccactgtac ttttagctcg    1140
tacaaaatac aatatacttt tcatttctcc gtaaacaaca tgttttccca tgtaatatcc    1200
ttttctattt ttcgttccgt taccaacttt acacatactt tatatagcta ttcacttcta    1260
tacactaaaa aactaagaca atttaatttt tgctgcctgc catatttcaa tttgttataa    1320
attcctataa tttatcctat tagtagctaa aaaagatga atgtgaatcg aatcctaaga    1380
gaattgggca agtgcacaaa caatacttaa ataaatacta ctcagtaata acctatttct    1440
tagcattttt gacgaaattt gctattttgt tagagtcttt tacaccattt gtctccacac    1500
ctccgcttac atcaacacca ataacgccat ttaatctaag cgcatcacca acattttctg    1560
gcgtcagtcc accagctaac ataaaatgta agctctcggg gctctcttgc cttccaaccc    1620
agtcagaaat cgagttccaa tccaaaagtt cacctgtccc acctgcttct gaatcaaaca    1680
agggaataaa cgaatgaggt ttctgtgaag ctgcactgag tagtatgttg cagtcttttg    1740
gaaatacgag tcttttaata actggcaaac cgaggaactc ttggtattct tgccacgact    1800
catctccgtg cagttggacg atatcaatgc cgtaatcatt gaccagagcc aaaacatcct    1860
ccttaggttg attacgaaac acgccaacca agtatttcgg agtgcctgaa ctatttttat    1920
atgcttttac aagacttgaa attttccttg caataaccgg gtcaattgtt ctctttctat    1980
tgggcacaca tataataccc agcaagtcag catcggaatc tagagcacat tctgcggcct    2040
ctgtgctctg caagccgcaa actttcacca atggaccaga actacctgtg aaattaataa    2100
cagacatact ccaagctgcc tttgtgtgct taatcacgta tactcacgtg ctcaatagtc    2160
accaatgccc tccctcttgg ccctctcctt ttctttttc gaccgaattt cttgaagacg    2220
aaagggcctc gtgatacgcc tatttttata ggttaatgtc atgataataa tggtttctta    2280
ggacggatcg cttgcctgta acttacacgc gcctcgtatc ttttaatgat ggaataattt    2340
```

```
gggaatttac tctgtgttta tttattttta tgttttgtat ttggatttta gaaagtaaat    2400
aaagaaggta gaagagttac ggaatgaaga aaaaaaaata aacaaaggtt taaaaaattt    2460
caacaaaaag cgtactttac atatatattt attagacaag aaaagcagat taaatagata    2520
tacattcgat taacgataag taaaatgtaa atcacagga ttttcgtgtg tggtcttcta    2580
cacagacaag atgaaacaat tcggcattaa tacctgagag caggaagagc aagataaaag    2640
gtagtatttg ttggcgatcc ccctagagtc ttttacatct tcggaaaaca aaaactatt    2700 tttcttaat ttcttttttt actttctatt tttaatttat atatttatat taaaaattt    2760 aaattataat tattttata gcacgtgatg aaaaggaccc aggtggcact ttcggggaa    2820 atgtgcgcgg aaccctatt tgtttatttt tctaaataca ttcaaatatg tatccgctca    2880
tgagacaata accctgataa atgcttcaat aatattgaaa aggaagagt atgagtattc    2940 aacattccg tgtcgccctt attcctttt ttgcggcatt ttgccttcct gtttttgctc    3000
acccagaaac gctggtgaaa gtaaaagatg ctgaagatca gttgggtgca cgagtgggtt    3060
acatcgaact ggatctcaac agcggtaaga tccttgagag ttttcgcccc gaagaacgtt    3120
ttccaatgat gagcactttt aaagttctgc tatgtggcgc ggtattatcc cgtgttgacg    3180
ccgggcaaga gcaactcggt cgccgcatac actattctca gaatgacttg gttgagtact    3240
caccagtcac agaaaagcat cttacggatg gcatgacagt aagagaatta tgcagtgctg    3300
ccataaccat gagtgataac actgcggcca acttacttct gacaacgatc ggaggaccga    3360
aggagctaac cgcttttttg cacaacatgg gggatcatgt aactcgcctt gatcgttggg    3420
aaccggagct gaatgaagcc ataccaaacg acgagcgtga ccacgatg cctgtagcaa    3480 tggcaacaac gttgcgcaaa ctattaactg gcgaactact tactctagct tcccggcaac    3540
aattaataga ctggatggag gcggataaag ttgcaggacc acttctgcgc tcggcccttc    3600
cggctggctg gtttattgct gataaatctg gagccggtga gcgtgggtct cgcggtatca    3660
ttgcagcact ggggccagat ggtaagccct cccgtatcgt agttatctac acgacgggca    3720
gtcaggcaac tatggatgaa cgaaatagac agatcgctga gataggtgcc tcactgatta    3780
agcattggta actgtcagac caagtttact catatatact ttagattgat ttaaaacttc    3840 attttaatt taaaggatc taggtgaaga tcctttttga taatctcatg accaaaatcc    3900
cttaacgtga gttttcgttc cactgagcgt cagaccccgt agaaaagatc aaaggatctt    3960
cttgagatcc ttttttttctg cgcgtaatct gctgcttgca acaaaaaaa ccaccgctac    4020 cagcggtggt ttgtttgccg gatcaagagc taccaactct ttttccgaag gtaactggct    4080
tcagcagagc gcagatacca aatactgtcc ttctagtgta gccgtagtta ggccaccact    4140
tcaagaactc tgtagcaccg cctacatacc tcgctctgct aatcctgtta ccagtggctg    4200
ctgccagtgg cgataagtcg tgtcttaccg ggttggactc aagacgatag ttaccggata    4260
aggcgcagcg gtcgggctga acggggggtt cgtgcacaca gcccagcttg gagcgaacga    4320
cctacaccga actgagatac ctacagcgtg agcattgaga aagcgccacg cttcccgaag    4380
ggagaaaggc ggacaggtat ccggtaagcg gcagggtcgg aacaggagag cgcacgaggg    4440
agcttccagg ggggaacgcc tggtatcttt atagtcctgt cgggtttcgc cacctctgac    4500
ttgagcgtcg atttttgtga tgctcgtcag ggggggccgag cctatggaaa aacgccagca    4560
acgcggcctt tttacggttc ctggcctttt gctggccttt tgctcacatg ttctttcctg    4620
cgttatcccc tgattctgtg gataaccgta ttaccgcctt tgagtgagct gataccgctc    4680
gccgcagccg aacgaccgag cgcagcgagt cagtgagcga ggaagcggaa gagcgcccaa    4740
```

```
tacgcaaacc gcctctcccc gcgcgttggc cgattcatta atgcagctgg cacgacaggt    4800
ttcccgactg gaaagcgggc agtgagcgca acgcaattaa tgtgagttac ctcactcatt    4860
aggcacccca ggctttacac tttatgcttc cggctcctat gttgtgtgga attgtgagcg    4920
gataacaatt tcacacagga aacagctatg accatgatta cgccaagctc ggaattaacc    4980
ctcactaaag ggaacaaaag ctggctagt                                      5009
```

<210> SEQ ID NO 7
<211> LENGTH: 919
<212> TYPE: DNA
<213> ORGANISM: Artificial Sequence
<220> FEATURE:
<223> OTHER INFORMATION: Plasmid

<400> SEQUENCE: 7

```
aaactgcata accactttaa ctaatacttt caacattttc ggtttgtatt acttcttatt      60
caaatgtaat aaaagtatca acaaaaaatt gttaatatac ctctatactt taacgtcaag     120
gagaaaaaac cccggatcgg actactagca gctgtaatac gactcactat agggaatatt     180
aagctaattc tacttcatac attttcaatt aagatgcagt tacttcgctg ttttcaata     240 ttttctgtta ttgcttcagt tttagcacag gaactgacaa ctatatgcga gcaaatcccc     300
tcaccaactt tagaatcgac gccgtactct ttgtcaacga ctactatttt ggccaacggg    360
aaggcaatgc aaggagtttt tgaatattac aaatcagtaa cgtttgtcag taattgcggt     420
tctcacccct caacaactag caaaggcagc cccataaaca cacagtatgt ttttaagctt     480
ctgcaggcta gtggtggtgg tggttctggt ggtggtggtt ctggtggtgg tggttctgct     540
agcatgactg gtggacagca aatgggtcgg gatctgtacg acgatgacga taaggtacca     600
ggatccagtg tggtggaatt ctgcagatat ccagcacagt ggcggccgct cgagtctaga     660
gggcccttcg aaggtaagcc tatccctaac cctctcctcg gtctcgattc tacgcgtacc     720
ggtcatcatc accatcacca ttgagtttaa acccgctgat ctgataacaa cagtgtagat     780
gtaacaaaat cgactttgtt cccactgtac ttttagctcg tacaaaatac aatatacttt     840
tcatttctcc gtaaacaaca tgttttccca tgtaatatcc ttttctattt ttcgttccgt     900
taccaacttt acacatact                                                  919
```

<210> SEQ ID NO 8
<211> LENGTH: 87
<212> TYPE: PRT
<213> ORGANISM: Saccharomyces cerevisiae

<400> SEQUENCE: 8

```
Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe
            85
```

```
<210> SEQ ID NO 9
<211> LENGTH: 451
<212> TYPE: DNA
<213> ORGANISM: Saccharomyces cerevisiae

<400> SEQUENCE: 9
acggattaga agccgccgag cgggtgacag ccctccgaag gaagactctc ctccgtgcgt      60
cctcgtcttc accggtcgcg ttcctgaaac gcagatgtgc ctcgcgccgc actgctccga     120
acaataaaga ttctacaata ctagctttta tggttatgaa gaggaaaaat tggcagtaac     180
ctggccccac aaaccttcaa atgaacgaat caaattaaca accataggat gataatgcga     240
ttagtttttt agccttattt ctggggtaat taatcagcga agcgatgatt tttgatctat     300
taacagatat ataaatgcaa aaactgcata accactttaa ctaatacttt caacattttc     360
ggtttgtatt acttcttatt caaatgtaat aaaagtatca acaaaaaatt gttaatatac     420
ctctatactt taacgtcaag gagaaaaaac c                                    451

<210> SEQ ID NO 10
<211> LENGTH: 2178
<212> TYPE: DNA
<213> ORGANISM: Saccharomyces cerevisiae

<400> SEQUENCE: 10
atgacattat ctttcgctca ttttacctac ctgttcacaa tattgttggg attaactaat      60
attgccttgg catctgatcc agaaacgatt ctagtgacga taaccaagac aaacgatgca     120
aatggggttg ttacaactac agtttcaccc gcgctagtct ccacatccac tatcgttcaa     180
gctggcacta cgacattgta tacgacttgg tgtccattga cggtatccac ttcatctgct     240
gccgaaataa gtccttcaat atcgtacgct actaccctat ccagatttag tactttgaca     300
ttatctacag aagtctgctc ccatgaggca tgtccttcgt catcgacgtt gccaaccacc     360
accttatctg tgacttccaa gttcacttca tatatttgcc ctacttgtca cacaaccgct     420
atcagctcat tatccgaagt aggaactaca accgtggtat catccagcgc cattgaacca     480
tcaagtgcct ctataatctc acctgtcacc tctacacttt cgagtacaac atcgtccaat     540
ccaactacta cctcccctaag ttcgacatct acatctccaa gctctacatc tacatctcca     600
agctctacat ctacctcatc aagttcgaca tctacctcat caagttcgac atctacctca     660
tcaagttcga catctacatc tccaagttcg acatccacat cttcaagttt gacatccaca     720
tcttcaagtt ctacatctac atcccaaagt tctacatcta cctcatcaag ttcgacatct     780
acatctccaa gctctacatc tacctcatca agttcaacat ctacatctcc aagttctaaa     840
tctacttctg caagctccac ttccacttct tcatattcaa catctacatc ccaagtttg      900 acttcttcat ctccaacttt ggcttccact tctccaagtt caacatctat agctctact      960 tttactgatt caacttcatc ccttggctcc tctatagcat cttcatcaac gtctgtgtca    1020
ttatacagcc catccacacc tgtttactcc gtccctttcga cttcgtcaaa tgttgcaact    1080
ccttctatga cttcttcaac tgttgaaaca actgttagtt cacaaagttc gtctgaatat    1140
atcaccaaat cctcaatttc tactactatc ccatcatttt ccatgtctac atatttcacc    1200
actgttagtg gagtcactac aatgtatacg acatggtgtc cttatagctc tgaatctgag    1260
actagcacat taaccagtat gcatgaaacg gttacaacga cgctacagt ctgcactcac    1320 gagtcttgca tgccctcgca gacaacaagt tgattacat cttctataaa aatgtccact    1380
aaaaacgtcg caacttctgt aagcacctca acggttgaat cctcatatgc atgctccaca    1440
tgtgctgaaa cgtcacactc gtattcttcc gtgcaaacag cttcatcaag ttctgtaaca    1500
```

```
cagcagacca catccacaaa gagttgggta agttcaatga caacttcgga tgaagatttc    1560
aataagcacg ctaccggtaa gtatcatgta acatcttcag gtacctcaac catttcgact    1620
agtgtaagtg aagccacgag tacatcaagc attgactcag aatctcaaga acaatcatca    1680
cacttattat cgacatcggt cctttcatcc tcctccttgt ctgctacatt atcctctgac    1740
agtactattt tgctattcag ttctgtatca tcactaagtg tcgaacagtc accagttacc    1800
acacttcaaa tttcttcaac atcagagatt ttacaaccca cttcttccac agctattgct    1860
acaatatctg cctctacatc atcactttcc gcaacatcta tctctacacc atctacctct    1920
gtggaatcga ctattgaatc ttcatcattg actccgacgg tatcttctat tttcctctca    1980
tcatcatctg ctccctcttc tctacaaaca tctgttacca ctacagaagt ttccactact    2040
tcaatctcca tacaatacca aacttcatca atggtaacaa ttagccaata tatgggcagt    2100
ggatcgcaaa cgcgtttgcc attaggaaag ttggtcttcg ccatcatggc agttgcttgc    2160
aatgtaattt tcagttaa                                                  2178

<210> SEQ ID NO 11
<211> LENGTH: 264
<212> TYPE: DNA
<213> ORGANISM: Saccharomyces cerevisiae

<400> SEQUENCE: 11
atgcagttac ttcgctgttt ttcaatattt tctgttattg cttcagtttt agcacaggaa      60
ctgacaacta tatgcgagca atcccctca ccaactttag aatcgacgcc gtactctttg     120
tcaacgacta ctattttggc caacgggaag gcaatgcaag gagtttttga atattacaaa    180
tcagtaacgt ttgtcagtaa ttgcggttct caccccctcaa caactagcaa aggcagcccc    240
ataaacacac agtatgtttt ttga                                            264

<210> SEQ ID NO 12
<211> LENGTH: 1953
<212> TYPE: DNA
<213> ORGANISM: Saccharomyces cerevisiae

<400> SEQUENCE: 12
atgttcactt ttctcaaaat tattctgtgg cttttttcct tggcattggc ctctgctata      60
aatatcaacg atatcacatt ttccaattta gaaattactc cactgactgc aaataaacaa    120
cctgatcaag gttggactgc cacttttgat tttagtattg cagatgcgtc ttccattagg    180
gagggcgatg aattcacatt atcaatgcca catgtttata ggattaagct attaaactca    240
tcgcaaacag ctactatttc cttagcggat ggtactgagg ctttcaaatg ctatgtttcg    300
caacaggctg catacttgta tgaaaatact actttcacat gtactgctca aaatgacctg    360
tcctcctata atacgattga tggatccata acattttcgc taaattttag tgatggtggt    420
tccagctatg aatatgagtt agaaaacgct aagtttttca atctgggcc aatgcttgtt    480 aaacttggta atcaaatgtc agatgtggtg aatttcgatc ctgctgcttt tacagagaat    540 gttttttcact ctgggcgttc aactggttac ggttcttttg aaagttatca tttgggtatg    600
tattgtccaa acggatattt cctggtggt actgagaaga ttgattacga cagttccaat    660
aacaatgtcg atttggattg ttcttcagtt caggtttatt catccaatga ttttaatgat    720
tggtggttcc cgcaaagtta caatgatacc aatgctgacg tcacttgttt tggtagtaat    780
ctgtggatta cacttgacga aaaactatat gatggggaaa tgttatgggt taatgcatta    840
caatctctac ccgctaatgt aaacacaata gatcatgcgt tagaatttca atacacatgc    900
```

| | |
|---|---:|
| cttgatacca tagcaaatac tacgtacgct acgcaattct cgactactag ggaatttatt | 960 |
| gtttatcagg gtcggaacct cggtacagct agcgccaaaa gctcttttat ctcaaccact | 1020 |
| actactgatt taacaagtat aaacactagt gcgtattcca ctggatccat ttccacagta | 1080 |
| gaaacaggca atcgaactac atcagaagtg atcagccatg tggtgactac cagcacaaaa | 1140 |
| ctgtctccaa ctgctactac cagcctgaca attgcacaaa ccagtatcta ttctactgac | 1200 |
| tcaaatatca cagtaggaac agatattcac accacatcag aagtgattag tgatgtggaa | 1260 |
| accattagca gagaaacagc ttcgaccgtt gtagccgctc caacctcaac aactggatgg | 1320 |
| acaggcgcta tgaatactta catctcgcaa tttacatcct cttctttcgc aacaatcaac | 1380 |
| agcacaccaa taatctcttc atcagcagta tttgaaacct cagatgcttc aattgtcaat | 1440 |
| gtgcacactg aaaatatcac gaatactgct gctgttccat ctgaagagcc cacttttgta | 1500 |
| aatgccacga gaaactcctt aaattccttc tgcagcagca acagccatc cagtccctca | 1560 |
| tcttatacgt cttccccact cgtatcgtcc ctctccgtaa gcaaaacatt actaagcacc | 1620 |
| agttttacgc cttctgtgcc aacatctaat acatatatca aaacgaaaaa tacgggttac | 1680 |
| tttgagcaca cggctttgac aacatcttca gttggcctta attcttttag tgaaacagca | 1740 |
| gtctcatctc agggaacgaa aattgacacc ttttagtgt catccttgat cgcatatcct | 1800 |
| tcttctgcat caggaagcca attgtccggt atccaacaga atttcacatc aacttctctc | 1860 |
| atgatttcaa cctatgaagg taaagcgtct atattttct cagctgagct cggttcgatc | 1920 |
| atttttctgc ttttgtcgta cctgctattc taa | 1953 |

<210> SEQ ID NO 13
<211> LENGTH: 4614
<212> TYPE: DNA
<213> ORGANISM: Saccharomyces cerevisiae

<400> SEQUENCE: 13

| | |
|---|---:|
| atgacaatgc ctcatcgcta tatgtttttg gcagtcttta cacttctggc actaactagt | 60 |
| gtggcctcag gagccacaga ggcgtgctta ccagcaggcc agaggaaaag tgggatgaat | 120 |
| ataaattttt accagtattc attgaaagat tcctccacat attcgaatgc agcatatatg | 180 |
| gcttatggat atgcctcaaa aaccaaaacta ggttctgtcg gaggacaaac tgatatctcg | 240 |
| attgattata atattccctg tgttagttca tcaggcacat ttccttgtcc tcaagaagat | 300 |
| tcctatggaa actggggatg caaaggaatg ggtgcttgtt ctaatagtca aggaattgca | 360 |
| tactggagta ctgatttatt tggtttctat actaccccaa caaacgtaac cctagaaatg | 420 |
| acaggttatt ttttaccacc acagacgggt tcttacacat tcaagtttgc tacagttgac | 480 |
| gactctgcaa ttctatcagt aggtggtgca accgcgttca actgttgtgc tcaacagcaa | 540 |
| ccgccgatca catcaacgaa ctttaccatt gacggtatca agccatgggg tggaagtttg | 600 |
| ccacctaata tcgaaggaac cgtctatatg tacgctggct actattatcc aatgaaggtt | 660 |
| gtttactcga acgctgtttc ttggggtaca cttccaatta gtgtgacact tccagatggt | 720 |
| accactgtaa gtgatgactt cgaagggtac gtctattcct ttgacgatga cctaagtcaa | 780 |
| tctaactgta ctgtccctga cccttcaaat tatgctgtca gtaccactac aactacaacg | 840 |
| gaaccatgga ccggtacttt cacttctaca tctactgaaa tgaccaccgt caccggtacc | 900 |
| aacggcgttc caactgacga aaccgtcatt gtcatcagaa ctccaacaac tgctagcacc | 960 |
| atcataacta caactgagcc atggaacagc acttttacct ctacttctac cgaattgacc | 1020 |
| acagtcactg gcaccaatgg tgtacgaact gacgaaacca tcattgtaat cagaacacca | 1080 |

```
acaacagcca ctactgccat aactacaact gagccatgga acagcacttt tacctctact   1140
tctaccgaat tgaccacagt caccggtacc aatggtttgc caactgatga gaccatcatt   1200
gtcatcagaa caccaacaac agccactact gccatgacta caactcagcc atggaacgac   1260
acttttacct ctacttctac cgaattgacc acagtcaccg gtaccaatgg tttgccaact   1320
gatgagacca tcattgtcat cagaacacca acaacagcca ctactgccat gactacaact   1380
cagccatgga acgacacttt tacctctact tctaccgaat tgaccacagt caccggtacc   1440
aatggtttgc caactgatga gaccatcatt gtcatcagaa caccaacaac agccactact   1500
gccatgacta caactcagcc atggaacgac acttttacct ctacatccac tgaaatcacc   1560
accgtcaccg gtaccaatgg tttgccaact gatgagacca tcattgtcat cagaacacca   1620
acaacagcca ctactgccat gactacacct cagccatgga acgacacttt tacctctaca   1680
tccactgaaa tgaccaccgt caccggtacc aacggtttgc caactgatga aaccatcatt   1740
gtcatcagaa caccaacaac agccactact gccataacta caactgagcc atggaacagc   1800
acttttacct ctacatccac tgaaatgacc accgtcaccg gtaccaacgg tttgccaact   1860
gatgaaacca tcattgtcat cagaacacca acaacagcca ctactgccat aactacaact   1920
cagccatgga acgacacttt tacctctaca tccactgaaa tgaccaccgt caccggtacc   1980
aacggtttgc caactgatga aaccatcatt gtcatcagaa caccaacaac agccactact   2040
gccatgacta caactcagcc atggaacgac acttttacct ctacatccac tgaaatcacc   2100
accgtcaccg gtaccaccgg tttgccaact gatgagacca tcattgtcat cagaacacca   2160
acaacagcca ctactgccat gactacaact cagccatgga acgacacttt tacctctaca   2220
tccactgaaa tgaccaccgt caccggtacc aacggcgttc caactgacga aaccgtcatt   2280
gtcatcagaa ctccaactag tgaaggtcta atcagcacca ccactgaacc atggactggt   2340
actttcacct ctacatccac tgagatgacc accgtcaccg gtactaacgg tcaaccaact   2400
gacgaaaccg tgattgttat cagaactcca accagtgaag gtttggttac aaccaccact   2460
gaaccatgga ctggtacttt tacttctaca tctactgaaa tgaccaccat tactggaacc   2520
aacggcgttc caactgacga aaccgtcatt gtcatcagaa ctccaaccag tgaaggtcta   2580
atcagcacca ccactgaacc atggactggt acttttactt ctacatctac tgaaatgacc   2640
accattactg gaaccaatgg tcaaccaact gacgaaaccg ttattgttat cagaactcca   2700
actagtgaag gtctaatcag cactacaacg gaaccatgga ccggtacttt cacttctaca   2760
tctactgaaa tgacgcacgt caccggtacc aacggcgttc caactgacga aaccgtcatt   2820
gtcatcagaa ctccaaccag tgaaggtcta atcagcacca ccactgaacc atggactggc   2880
actttcactt cgacttccac tgaggttacc accatcactg gaaccaacgg tcaaccaact   2940
gacgaaactg tgattgttat cagaactcca accagtgaag gtctaatcag caccaccact   3000
gaaccatgga ctggtacttt cacttctaca tctactgaaa tgaccaccgt caccggtact   3060
aacggtcaac caactgacga aaccgtgatt gttatcagaa ctccaaccag tgaaggtttg   3120
gttacaacca ccactgaacc atggactggt acttttactt cgacttccac tgaaatgtct   3180
actgtcactg gaaccaatgg cttgccaact gatgaaactg tcattgttgt caaaactcca   3240
actactgcca tctcatccag tttgtcatca tcatcttcag acaaatcac cagctctatc   3300 acgtcttcgc gtccaattat taccccattc tatcctagca atggaacttc tgtgatttct   3360
tcctcagtaa tttcttcctc agtcacttct tctctattca cttcttctcc agtcatttct   3420
tcctcagtca tttcttcttc tacaacaacc tccacttcta tattttctga atcatctaaa   3480
```

-continued

```
tcatccgtca ttccaaccag tagttccacc tctggttctt ctgagagcga aacgagttca    3540
gctggttctg tctcttcttc ctcttttatc tcttctgaat catcaaaatc tcctacatat    3600
tcttcttcat cattaccact tgttaccagt gcgacaacaa gccaggaaac tgcttcttca    3660
ttaccacctg ctaccactac aaaaacgagc gaacaaacca ctttggttac cgtgacatcc    3720
tgcgagtctc atgtgtgcac tgaatccatc tccctgcga ttgtttccac agctactgtt    3780
actgttagcg gcgtcacaac agagtatacc acatggtgcc ctatttctac tacagagaca    3840
acaaagcaaa ccaagggac aacagagcaa accacagaaa caacaaaaca aaccacggta    3900
gttacaattt cttcttgtga atctgacgta tgctctaaga ctgcttctcc agccattgta    3960
tctacaagca ctgctactat taacggcgtt actacagaat acacaacatg gtgtcctatt    4020
tccaccacag aatcgaggca acaaacaacg ctagttactg ttacttcctg cgaatctggt    4080
gtgtgttccg aaactgcttc acctgccatt gtttcgacgg ccacggctac tgtgaatgat    4140
gttgttacgg tctatcctac atggaggcca cagactgcga tgaagagtc tgtcagctct    4200
aaaatgaaca gtgctaccgg tgagacaaca accaatactt tagctgctga aacgactacc    4260
aatactgtag ctgctgagac gattaccaat actggagctg ctgagacgaa acagtagtc    4320
acctcttcgc tttcaagatc taatcacgct gaaacacaga cggcttccgc gaccgatgtg    4380
attggtcaca gcagtagtgt tgtttctgta tccgaaactg gcaacaccaa gagtctaaca    4440
agttccgggt tgagtactat gtcgcaacag cctcgtagca caccagcaag cagcatggta    4500
ggatatagta cagcttcttt agaaatttca acgtatgctg gcagtgccaa cagcttactg    4560
gccggtagtg gtttaagtgt cttcattgcg tccttattgc tggcaattat ttaa           4614
```

<210> SEQ ID NO 14
<211> LENGTH: 239
<212> TYPE: PRT
<213> ORGANISM: Saccharomyces cerevisiae

<400> SEQUENCE: 14

```
Met Lys Phe Ser Thr Ala Leu Ser Val Ala Leu Phe Ala Leu Ala Lys
1               5                   10                  15

Met Val Ile Ala Asp Ser Glu Glu Phe Gly Leu Val Ser Ile Arg Ser
            20                  25                  30

Gly Ser Asp Leu Gln Tyr Leu Ser Val Tyr Ser Asp Asn Gly Thr Leu
        35                  40                  45

Lys Leu Gly Ser Gly Ser Gly Ser Phe Glu Ala Thr Ile Thr Asp Asp
    50                  55                  60

Gly Lys Leu Lys Phe Asp Asp Asp Lys Tyr Ala Val Val Asn Glu Asp
65                  70                  75                  80

Gly Ser Phe Lys Glu Gly Ser Glu Ser Asp Ala Ala Thr Gly Phe Ser
                85                  90                  95

Ile Lys Asp Gly His Leu Asn Tyr Lys Ser Ser Gly Phe Tyr Ala
            100                 105                 110

Ile Lys Asp Gly Ser Ser Tyr Ile Phe Ser Lys Gln Ser Asp Asp
        115                 120                 125

Ala Thr Gly Val Ala Ile Arg Pro Thr Ser Lys Ser Gly Ser Val Ala
    130                 135                 140

Ala Asp Phe Ser Pro Ser Asp Ser Ser Ser Ser Ser Ala Ser Ala
145                 150                 155                 160

Ser Ser Ala Ser Ala Ser Ser Ser Thr Lys His Ser Ser Ser Ile Glu
                165                 170                 175
```

```
Ser Val Glu Thr Ser Thr Thr Val Glu Thr Ser Ser Ala Ser Ser Pro
            180                 185                 190

Thr Ala Ser Val Ile Ser Gln Ile Thr Asp Gly Gln Ile Gln Ala Pro
            195                 200                 205

Asn Thr Val Tyr Glu Gln Thr Glu Asn Ala Gly Ala Lys Ala Ala Val
        210                 215                 220

Gly Met Gly Ala Gly Ala Leu Ala Val Ala Ala Ala Tyr Leu Leu
225                 230                 235

<210> SEQ ID NO 15
<211> LENGTH: 92
<212> TYPE: PRT
<213> ORGANISM: Saccharomyces cerevisiae

<400> SEQUENCE: 15

Met Gln Phe Ser Thr Val Ala Ser Val Ala Phe Val Ala Leu Ala Asn
1               5                   10                  15

Phe Val Ala Ala Glu Ser Ala Ala Ala Ile Ser Gln Ile Thr Asp Gly
            20                  25                  30

Gln Ile Gln Ala Thr Thr Thr Ala Thr Thr Glu Ala Thr Thr Thr Ala
        35                  40                  45

Ala Pro Ser Ser Thr Val Glu Thr Val Ser Pro Ser Ser Thr Glu Thr
    50                  55                  60

Ile Ser Gln Gln Thr Glu Asn Gly Ala Ala Lys Ala Ala Val Gly Met
65                  70                  75                  80

Gly Ala Gly Ala Leu Ala Ala Ala Ala Met Leu Leu
                85                  90

<210> SEQ ID NO 16
<211> LENGTH: 210
<212> TYPE: PRT
<213> ORGANISM: Saccharomyces cerevisiae

<400> SEQUENCE: 16

Met Ser Val Ser Lys Ile Ala Phe Val Leu Ser Ala Ile Ala Ser Leu
1               5                   10                  15

Ala Val Ala Asp Thr Ser Ala Ala Glu Thr Ala Glu Leu Gln Ala Ile
            20                  25                  30

Ile Gly Asp Ile Asn Ser His Leu Ser Asp Tyr Leu Gly Leu Glu Thr
        35                  40                  45

Gly Asn Ser Gly Phe Gln Ile Pro Ser Asp Val Leu Ser Val Tyr Gln
    50                  55                  60

Gln Val Met Thr Tyr Thr Asp Asp Ala Tyr Thr Thr Leu Phe Ser Glu
65                  70                  75                  80

Leu Asp Phe Asp Ala Ile Thr Lys Thr Ile Val Lys Leu Pro Trp Tyr
                85                  90                  95

Thr Thr Arg Leu Ser Ser Glu Ile Ala Ala Leu Ala Ser Val Ser
            100                 105                 110

Pro Ala Ser Ser Glu Ala Ala Ser Ser Glu Ala Ala Ser Ser Ser
            115                 120                 125

Lys Ala Ala Ser Ser Glu Ala Thr Ser Ser Ala Pro Ser Ser
        130                 135                 140

Ser Ala Ala Pro Ser Ser Ala Ala Pro Ser Ser Ala Glu Ser
145                 150                 155                 160

Ser Ser Lys Ala Val Ser Ser Val Ala Pro Thr Ser Ser Val
                165                 170                 175
```

```
Ser Thr Ser Thr Val Glu Thr Ala Ser Asn Ala Gly Gln Arg Val Asn
            180                 185                 190

Ala Gly Ala Ala Ser Phe Gly Ala Val Val Ala Gly Ala Ala Ala Leu
        195                 200                 205

Leu Leu
    210

<210> SEQ ID NO 17
<211> LENGTH: 254
<212> TYPE: PRT
<213> ORGANISM: Saccharomyces cerevisiae

<400> SEQUENCE: 17

Met Ala Tyr Thr Lys Ile Ala Leu Phe Ala Ala Ile Ala Ala Leu Ala
1               5                   10                  15

Ser Ala Gln Thr Gln Asp Gln Ile Asn Glu Leu Asn Val Ile Leu Asn
            20                  25                  30

Asp Val Lys Ser His Leu Gln Glu Tyr Ile Ser Leu Ala Ser Asp Ser
        35                  40                  45

Ser Ser Gly Phe Ser Leu Ser Ser Met Pro Ala Gly Val Leu Asp Ile
    50                  55                  60

Gly Met Ala Leu Ala Ser Ala Thr Asp Asp Ser Tyr Thr Thr Leu Tyr
65                  70                  75                  80

Ser Glu Val Asp Phe Ala Gly Val Ser Lys Met Leu Thr Met Val Pro
                85                  90                  95

Trp Tyr Ser Ser Arg Leu Glu Pro Ala Leu Lys Ser Leu Asn Gly Asp
            100                 105                 110

Ala Ser Ser Ser Ala Ala Pro Ser Ser Ala Ala Pro Thr Ser Ser
        115                 120                 125

Ala Ala Pro Ser Ser Ser Ala Ala Pro Thr Ser Ser Ala Ala Ser Ser
    130                 135                 140

Ser Ser Glu Ala Lys Ser Ser Ala Ala Pro Ser Ser Ser Glu Ala
145                 150                 155                 160

Lys Ser Ser Ser Ala Ala Pro Ser Ser Ser Glu Ala Lys Ser Ser Ser
                165                 170                 175

Ala Ala Pro Ser Ser Ser Glu Ala Lys Ser Ser Ser Ala Ala Pro Ser
            180                 185                 190

Ser Thr Glu Ala Lys Ile Thr Ser Ala Ala Pro Ser Ser Thr Gly Ala
        195                 200                 205

Lys Thr Ser Ala Ile Ser Gln Ile Thr Asp Gly Gln Ile Gln Ala Thr
    210                 215                 220

Lys Ala Val Ser Glu Gln Thr Glu Asn Gly Ala Ala Lys Ala Phe Val
225                 230                 235                 240

Gly Met Gly Ala Gly Val Val Ala Ala Ala Met Leu Leu
                245                 250

<210> SEQ ID NO 18
<211> LENGTH: 338
<212> TYPE: PRT
<213> ORGANISM: Saccharomyces cerevisiae

<400> SEQUENCE: 18

Met Lys Leu Ser Thr Val Leu Leu Ser Ala Gly Leu Ala Ser Thr Thr
1               5                   10                  15

Leu Ala Gln Phe Ser Asn Ser Thr Ser Ala Ser Ser Thr Asp Val Thr
            20                  25                  30
```

-continued

```
Ser Ser Ser Ser Ile Ser Thr Ser Ser Gly Ser Val Thr Ile Thr Ser
            35                  40                  45

Ser Glu Ala Pro Glu Ser Asp Asn Gly Thr Ser Thr Ala Ala Pro Thr
 50                  55                  60

Glu Thr Ser Thr Glu Ala Pro Thr Thr Ala Ile Pro Thr Asn Gly Thr
 65                  70                  75                  80

Ser Thr Glu Ala Pro Thr Thr Ala Ile Pro Thr Asn Gly Thr Ser Thr
                85                  90                  95

Glu Ala Pro Thr Asp Thr Thr Glu Ala Pro Thr Thr Thr Glu Ala
            100                 105                 110

Thr Asn Gly Thr Ser Thr Glu Ala Pro Thr Asp Thr Thr Glu Ala
            115                 120                 125

Pro Thr Thr Gly Leu Pro Thr Asn Gly Thr Thr Ser Ala Phe Pro Pro
        130                 135                 140

Thr Thr Ser Leu Pro Pro Ser Asn Thr Thr Thr Thr Pro Pro Tyr Asn
145                 150                 155                 160

Pro Ser Thr Asp Tyr Thr Thr Asp Tyr Thr Val Val Thr Glu Tyr Thr
                165                 170                 175

Thr Tyr Cys Pro Glu Pro Thr Thr Phe Thr Thr Asn Gly Lys Thr Tyr
            180                 185                 190

Thr Val Thr Glu Pro Thr Thr Leu Thr Ile Thr Asp Cys Pro Cys Thr
            195                 200                 205

Ile Glu Lys Pro Thr Thr Thr Ser Thr Thr Glu Tyr Thr Val Val Thr
        210                 215                 220

Glu Tyr Thr Thr Tyr Cys Pro Glu Pro Thr Thr Phe Thr Thr Asn Gly
225                 230                 235                 240

Lys Thr Tyr Thr Val Thr Glu Pro Thr Thr Leu Thr Ile Thr Asp Cys
                245                 250                 255

Pro Cys Thr Ile Glu Lys Ser Glu Ala Pro Glu Ser Ser Val Pro Val
            260                 265                 270

Thr Glu Ser Lys Gly Thr Thr Thr Lys Glu Thr Gly Val Thr Thr Lys
            275                 280                 285

Gln Thr Thr Ala Asn Pro Ser Leu Thr Val Ser Thr Val Val Pro Val
        290                 295                 300

Ser Ser Ser Ala Ser Ser His Ser Val Val Ile Asn Ser Asn Gly Ala
305                 310                 315                 320

Asn Val Val Val Pro Gly Ala Leu Gly Leu Ala Gly Val Ala Met Leu
                325                 330                 335

Phe Leu

<210> SEQ ID NO 19
<211> LENGTH: 313
<212> TYPE: PRT
<213> ORGANISM: Saccharomyces cerevisiae

<400> SEQUENCE: 19

Met Asn Ser Phe Ala Ser Leu Gly Leu Ile Tyr Ser Val Val Asn Leu
1               5                   10                  15

Leu Thr Arg Val Glu Ala Gln Ile Val Phe Tyr Gln Asn Ser Ser Thr
            20                  25                  30

Ser Leu Pro Val Pro Thr Leu Val Ser Thr Ser Ile Ala Asp Phe His
        35                  40                  45

Glu Ser Ser Ser Thr Gly Glu Val Gln Tyr Ser Ser Ser Tyr Ser Tyr
    50                  55                  60
```

```
Val Gln Pro Ser Ile Asp Ser Phe Thr Ser Ser Ser Phe Leu Thr Ser
 65                  70                  75                  80

Phe Glu Ala Pro Thr Glu Thr Ser Ser Ser Tyr Ala Val Ser Ser Ser
                 85                  90                  95

Leu Ile Thr Ser Asp Thr Phe Ser Ser Tyr Ser Asp Ile Phe Asp Glu
            100                 105                 110

Glu Thr Ser Ser Leu Ile Ser Thr Ser Ala Ala Ser Ser Glu Lys Ala
        115                 120                 125

Ser Ser Thr Leu Ser Ser Thr Ala Gln Pro His Arg Thr Ser His Ser
130                 135                 140

Ser Ser Ser Phe Glu Leu Pro Val Thr Ala Pro Ser Ser Ser Ser Leu
145                 150                 155                 160

Pro Ser Ser Thr Ser Leu Thr Phe Thr Ser Val Asn Pro Ser Gln Ser
                165                 170                 175

Trp Thr Ser Phe Asn Ser Glu Lys Ser Ser Ala Leu Ser Ser Thr Ile
            180                 185                 190

Asp Phe Thr Ser Ser Glu Ile Ser Gly Ser Thr Ser Pro Lys Ser Leu
        195                 200                 205

Glu Ser Phe Asp Thr Thr Gly Thr Ile Thr Ser Ser Tyr Ser Pro Ser
210                 215                 220

Pro Ser Ser Lys Asn Ser Asn Gln Thr Ser Leu Leu Ser Pro Leu Glu
225                 230                 235                 240

Pro Leu Ser Ser Ser Gly Asp Leu Ile Leu Ser Ser Thr Ile Gln
                245                 250                 255

Ala Thr Thr Asn Asp Gln Thr Ser Lys Thr Ile Pro Thr Leu Val Asp
            260                 265                 270

Ala Thr Ser Ser Leu Pro Pro Thr Leu Arg Ser Ser Ser Met Ala Pro
        275                 280                 285

Thr Ser Gly Ser Asp Ser Ile Ser His Asn Phe Thr Ser Pro Pro Ser
290                 295                 300

Lys Thr Ser Gly Asn Tyr Asp Val Leu
305                 310

<210> SEQ ID NO 20
<211> LENGTH: 744
<212> TYPE: PRT
<213> ORGANISM: Saccharomyces cerevisiae

<400> SEQUENCE: 20

Met Asn Ser Phe Ala Ser Leu Gly Leu Ile Tyr Ser Val Val Asn Leu
 1               5                  10                  15

Leu Thr Arg Val Glu Ala Gln Ile Val Phe Tyr Gln Asn Ser Ser Thr
             20                  25                  30

Ser Leu Pro Val Pro Thr Leu Val Ser Thr Ser Ile Ala Asp Phe His
         35                  40                  45

Glu Ser Ser Ser Thr Gly Glu Val Gln Tyr Ser Ser Tyr Ser Tyr
     50                  55                  60

Val Gln Pro Ser Ile Asp Ser Phe Thr Ser Ser Ser Phe Leu Thr Ser
 65                  70                  75                  80

Phe Glu Ala Pro Thr Glu Thr Ser Ser Ser Tyr Ala Val Ser Ser Ser
                 85                  90                  95

Leu Ile Thr Ser Asp Thr Phe Ser Ser Tyr Ser Asp Ile Phe Asp Glu
            100                 105                 110

Glu Thr Ser Ser Leu Ile Ser Thr Ser Ala Ala Ser Ser Glu Lys Ala
        115                 120                 125
```

```
Ser Ser Thr Leu Ser Ser Thr Ala Gln Pro His Arg Thr Ser His Ser
    130                 135                 140

Ser Ser Ser Phe Glu Leu Pro Val Thr Ala Pro Ser Ser Ser Ser Leu
145                 150                 155                 160

Pro Ser Ser Thr Ser Leu Thr Phe Thr Ser Val Asn Pro Ser Gln Ser
                165                 170                 175

Trp Thr Ser Phe Asn Ser Glu Lys Ser Ser Ala Leu Ser Ser Thr Ile
                180                 185                 190

Asp Phe Thr Ser Ser Glu Ile Ser Gly Ser Thr Ser Pro Lys Ser Leu
            195                 200                 205

Glu Ser Phe Asp Thr Thr Gly Thr Ile Thr Ser Ser Tyr Ser Pro Ser
    210                 215                 220

Pro Ser Ser Lys Asn Ser Asn Gln Thr Ser Leu Leu Ser Pro Leu Glu
225                 230                 235                 240

Pro Leu Ser Ser Ser Ser Gly Asp Leu Ile Leu Ser Ser Thr Ile Gln
                245                 250                 255

Ala Thr Thr Asn Asp Gln Thr Ser Lys Thr Ile Pro Thr Leu Val Asp
                260                 265                 270

Ala Thr Ser Ser Leu Pro Pro Thr Leu Arg Ser Ser Ser Met Ala Pro
            275                 280                 285

Thr Ser Gly Ser Asp Ser Ile Ser His Asn Phe Thr Ser Pro Pro Ser
    290                 295                 300

Lys Thr Ser Gly Asn Tyr Asp Val Leu Thr Ser Asn Ser Ile Asp Pro
305                 310                 315                 320

Ser Leu Phe Thr Thr Thr Ser Glu Tyr Ser Ser Thr Gln Leu Ser Ser
                325                 330                 335

Leu Asn Arg Ala Ser Lys Ser Glu Thr Val Asn Phe Thr Ala Ser Ile
                340                 345                 350

Ala Ser Thr Pro Phe Gly Thr Asp Ser Ala Thr Ser Leu Ile Asp Pro
            355                 360                 365

Ile Ser Ser Val Gly Ser Thr Ala Ser Ser Phe Val Gly Ile Ser Thr
    370                 375                 380

Ala Asn Phe Ser Thr Gln Gly Asn Ser Asn Tyr Val Pro Glu Ser Thr
385                 390                 395                 400

Ala Ser Gly Ser Ser Gln Tyr Gln Asp Trp Ser Ser Ser Ser Leu Pro
                405                 410                 415

Leu Ser Gln Thr Thr Trp Val Val Ile Asn Thr Thr Asn Thr Gln Gly
                420                 425                 430

Ser Val Thr Ser Thr Ser Pro Ala Tyr Val Ser Thr Ala Thr Lys
            435                 440                 445

Thr Val Asp Gly Val Ile Thr Glu Tyr Val Thr Trp Cys Pro Leu Thr
    450                 455                 460

Gln Thr Lys Ser Gln Ala Ile Gly Val Ser Ser Ile Ser Ser Val
465                 470                 475                 480

Pro Gln Ala Ser Ser Phe Ser Gly Ser Ser Ile Leu Ser Ser Asn Ser
                485                 490                 495

Ser Thr Leu Ala Ala Ser Asn Asn Val Pro Glu Ser Thr Ala Ser Gly
                500                 505                 510

Ser Ser Gln Tyr Gln Asp Trp Ser Ser Ser Leu Pro Leu Ser Gln
            515                 520                 525

Thr Thr Trp Val Val Ile Asn Thr Thr Asn Thr Gln Gly Ser Val Thr
    530                 535                 540

Ser Thr Thr Ser Pro Ala Tyr Val Ser Thr Ala Thr Lys Thr Val Asp
545                 550                 555                 560
```

```
Gly Val Ile Thr Glu Tyr Val Thr Trp Cys Pro Leu Thr Gln Thr Lys
                565                 570                 575
Ser Gln Ala Ile Gly Ile Ser Ser Thr Ile Ser Ala Thr Gln Thr
        580                 585                 590
Ser Lys Pro Ser Ser Ile Leu Thr Leu Gly Ile Ser Thr Leu Gln Leu
        595                 600                 605
Ser Asp Ala Thr Phe Lys Gly Thr Glu Thr Ile Asn Thr His Leu Met
        610                 615                 620
Thr Glu Ser Thr Ser Ile Thr Glu Pro Thr Tyr Phe Ser Gly Thr Ser
625                 630                 635                 640
Asp Ser Phe Tyr Leu Cys Thr Ser Glu Val Asn Leu Ala Ser Ser Leu
                645                 650                 655
Ser Ser Tyr Pro Asn Phe Ser Ser Glu Gly Ser Thr Ala Thr Ile
                660                 665                 670
Thr Asn Ser Thr Val Thr Phe Gly Ser Thr Ser Lys Tyr Pro Ser Thr
                675                 680                 685
Ser Val Ser Asn Pro Thr Glu Ala Ser Gln His Val Ser Ser Ser Val
        690                 695                 700
Asn Ser Leu Thr Asp Phe Thr Ser Asn Ser Thr Glu Thr Ile Ala Val
705                 710                 715                 720
Ile Ser Asn Ile His Lys Thr Ser Ser Asn Lys Asp Tyr Ser Leu Thr
                725                 730                 735
Thr Thr Gln Leu Lys Thr Ser Gly
                740

<210> SEQ ID NO 21
<211> LENGTH: 720
<212> TYPE: DNA
<213> ORGANISM: Saccharomyces cerevisiae

<400> SEQUENCE: 21
atgaaattct ccactgcttt gtctgtcgct ttattcgcct tggctaagat ggtcattgcc      60
gattccgaag aattcggcct ggtgagtatc cgttccggct cggatttaca atacttgagt     120
gtttacagtg ataacggcac tttgaaactt ggcagcggta gtggctcatt tgaggcaact     180
attaccgatg acggtaaact gaaatttgac gacgataagt atgctgttgt caatgaggat     240
ggctcattca agaaggttc tgagagcgat gctgccactg ttttttctat taagatggc      300 catctaaact acaagagctc ttctggtttc tacgctatca aggacgggtc gtcttacatt     360
ttctcttcta gcaatccga cgacgctacc ggtgttgcga ttagaccaac tagtaagagc      420
ggatctgttg cagcagattt ttctccaagc gactctagtt cctcttcatc tgcttctgct     480
tcgtctgctt ccgcatcatc ttctacaaag catagttcga gtatagaatc tgtcgagacc     540
tctactactg tggaaacttc ctctgctagc tccccaactg cttcagttat ctctcaaatt     600
actgatggac aaatccaagc tccaaacaca gtttacgaac aaacagaaaa tgcaggtgcc     660
aaggctgccg tcggcatggg tgctggtgct ctagcggtcg cagctgctta cttgttgtaa    720

<210> SEQ ID NO 22
<211> LENGTH: 279
<212> TYPE: DNA
<213> ORGANISM: Saccharomyces cerevisiae

<400> SEQUENCE: 22
atgcaattct ctactgtcgc ttccgttgct ttcgtcgctt ggctaacttg tgttgccgct      60
gaatccgctg ccgccatttc tcaaatcact gacggtcaaa tccaagctac taccactgct     120
```

| | | |
|---|---|---|
| accaccgaag ctaccaccac tgctgcccca tcttccaccg ttgaaactgt ttctccatcc | 180 | |
| agcaccgaaa ctatctctca acaaactgaa aatggtgctg ctaaggccgc tgtcggtatg | 240 | |
| ggtgccggtg ctctagctgc tgctgctatg ttgttataa | 279 | |

<210> SEQ ID NO 23
<211> LENGTH: 633
<212> TYPE: DNA
<213> ORGANISM: Saccharomyces cerevisiae

<400> SEQUENCE: 23

| | |
|---|---|
| atgtccgttt ccaagattgc tttcgtttta agtgccattg cctctttggc cgtcgctgac | 60 |
| accagcgccg ccgaaactgc tgaattgcaa gctattatcg gtgacatcaa ctctcatctt | 120 |
| tctgactact tgggtctaga aactggcaac agtggattcc aaattccatc tgatgtcttg | 180 |
| agtgtgtatc aacaagtcat gacttacacc gatgacgctt acactacctt gtttagtgaa | 240 |
| ttggactttg atgctatcac taagacaatt gttaaattgc catggtacac cacaagattg | 300 |
| agttctgaaa tcgctgctgc tcttgcctcc gtttccccag cttcttccga ggctgcatct | 360 |
| tcttccgagg ctgcatcttc ttccaaggct gcatcttctt ccgaagctac atcctctgcc | 420 |
| gctccatcct cttctgctgc cccatcttct tctgctgccc catcatcatc tgccgaatca | 480 |
| tcttctaagg ccgtttcttc ttctgtcgct ccaactacct cttctgtcag cacttctaca | 540 |
| gtcgaaactg cttccaatgc cggtcaaaga gtcaatgcag gcgctgcctc tttcggtgct | 600 |
| gttgttgcag gtgcagctgc tttattgtta taa | 633 |

<210> SEQ ID NO 24
<211> LENGTH: 765
<212> TYPE: DNA
<213> ORGANISM: Saccharomyces cerevisiae

<400> SEQUENCE: 24

| | |
|---|---|
| atggcttaca ctaagatcgc tttattcgct gctattgctg ctttggcttc cgctcaaacc | 60 |
| caagatcaaa ttaacgaatt gaacgttatt ttgaacgatg tcaaatctca cttgcaagag | 120 |
| tacattagct tagcttctga ttcttcctct ggattttcct taagcagtat gccagctggt | 180 |
| gttttggata tcggtatggc tttagcttcc gccactgacg actcctacac tactttgtac | 240 |
| tctgaggttg actttgctgg tgttagcaag atgttgacca tggttccatg gtactcctct | 300 |
| agattggaac cagctttgaa gtcttttgaat ggtgatgctc cttcttctgc tgccccaagc | 360 |
| tcttctgctg ctccaacttc ttctgctgcc ccaagctcat ctgctgcccc aacttcttct | 420 |
| gctgcctcaa gctcttctga agctaagtct tcttctgctg ccccaagctc ttctgaagct | 480 |
| aagtcttctt ctgctgcccc aagctcttct gaagctaagt cttcttctgc tgccccaagc | 540 |
| tcttctgaag ctaagtcttc ttctgctgct ccaagctcca ctgaagctaa gataacttct | 600 |
| gctgctccaa gctccactgg tgccaagacc tctgccatct ctcaaattac cgatggtcaa | 660 |
| atccaagcta ccaaggctgt ttctgagcaa actgaaaacg gtgctgctaa ggcctttgtt | 720 |
| ggtatgggtg ctggtgttgt cgcagctgcc gctatgttgt tataa | 765 |

<210> SEQ ID NO 25
<211> LENGTH: 4830
<212> TYPE: DNA
<213> ORGANISM: Saccharomyces cerevisiae

<400> SEQUENCE: 25

```
atgaactcat ttgcgtcatt aggtctgata tattcagtag taaacctttt aactagagta      60
gaggctcaaa ttgtgttcta ccagaatagt agtacttcac tgcctgtccc tactttagta     120
tccacctcaa tagcagattt tcacgagtcc tcatcaactg gcgaagtgca gtattcatcc     180
tcttattcgt atgtgcagcc ctcaatagac tccttcactt catctagctt cttaacaagt     240
tttgaagctc ctaccgaaac ttcttccagc tatgcagttt cttcctcatt gataacttct     300
gatactttt cttcatactc tgatatcttc gatgaagaaa caagttcatt aatatcaacc      360
tcagctgcct catcggagaa agcctcgtcc acctttctt caactgcaca acctcatagg      420
acatctcact cttcctcttc attcgagcta ccagtcactg ctccatcatc tctagttta     480
ccgtcctcaa cttcattgac atttacgtca gttaatccat ctcaaagttg gacttcattt     540
aactcagaaa aatctagcgc tctttcctca accatagatt ttacttcttc tgagatttca     600
ggttcaacat ctccaaagag cctggaaagt ttcgatacca ccggtactat aacttcatct     660
tattctcctt ctccttcttc aaaaaattct aaccagacct cactactcag cccattggag     720
cctctgtcca gttcttcagg agatttaata ttgagttcaa ctattcaagc tactaccaat     780
gaccaaactt caaaaactat tccaactctt gttgacgcca catcgtcatt accaccaaca     840
ttgaggtcat ccagtatggc accaacaagt ggttctgatt caatctcaca caactttacg     900
agccccccct ctaaaacaag tggtaactac gatgttttga cttcaaactc aatagatcct     960
tctctattta caactacgag tgaatattca tctacacaat gtcgagtttt aaatcgggcc    1020
tcaaaaagtg aaacagttaa tttcactgct tctattgctt ccacaccatt tggtacagat    1080
tcggctactt ctctaataga ccccattagt tcagtgggtt ctacagcatc tagcttgtg    1140
ggaatttcaa ccgccaattt tagtacacaa gggaactcga actatgttcc tgaatcaact    1200
gcaagtggaa gttcacaata ccaggactgg tcagctctt ctcttccgct gtcacaaacc    1260
acttgggttg tcatcaacac aactaataca caagggtctg taacgtcaac cacatccccg    1320
gcttatgttt ctacggccac caaaacggtt gacggggtga tcaccgaata tgttacatgg    1380
tgtcctctaa cacaaaccaa atcacaagca attggggtca gttcgtccat ttctagcgtt    1440
ccacaagcct cctcatttag cggtagttct attttgagct ccaattccag cactcttgct    1500
gcctcgaaca acgttcctga atcaactgca agcggaagtt cacaatacca ggactggtca    1560
agctcttctc ttccgctgtc acaaaccact tgggttgtca tcaacacaac taatacacaa    1620
gggtctgtaa cgtcaaccac atccccggct tatgtttcta cggccaccaa aacggttgac    1680
ggggtgatca ccgaatatgt tacatggtgt cctctaacac aaaccaaatc acaagcaatt    1740
gggatcagtt catccacgat tagcgccaca caaacctcta aaccatcttc aatattaaca    1800
ttggggatat cgaccttaca attgtctgat gccacattta aggggactga actataaac    1860
acccatctca tgaccgaaag tacttcaatc acagagccca cctattttag tggcacatcg    1920
gatagtttt atttgtgcac cagtgaagtt aatcttgcgt cttccttatc ttcttatcca    1980
aattttcat cttcagaagg ctctacggcg accattacta actctaccgt tacatttgga    2040
tcgaccagca agtatccatc tactagtgta tctaacccaa cagaagccag ccaacatgtg    2100
agctctagtg tgaactcact cactgatttt acttcaaatt caaccgaaac catcgcagtt    2160
atatctaata ttcacaaaac ttcgtcaaat aaagactatt cattgacgac tacgcaatta    2220
aagaccagcg gaatgcaaac gcttgtgctt tctactgtca caacaacggt gaacggtgct    2280
gctacggaat acacaacgtg gtgcccggca tcaagtattg cttatacgac atccatatca    2340
```

-continued

```
tataaaacat tagttttgac cactgaagtc tgctctcatt ctgagtgtac tccaacggtt    2400
attaccagtg ttactgcaac aagctctaca atcccccttt tatcaacctc tagctctacg    2460
gtattatctt ctacagtatc cgaaggtgca aaaaatcccg ctgcttctga agtaactatt    2520
aatacccaag tttctgctac ttccgaagct actagtacta gcactcaagt gtctgctact    2580
tctgcgacgg ccactgctag cgagagttca accacatccc aggtttctac tgcttccgaa    2640
actattagca ctctcggtac tcaaaacttt accactactg gaagcttact tttcccggct    2700
ttgtctactg aaatgataaa tactactgtg gtttcccgaa aaaccctaat tattagtaca    2760
gaggtatgtt cccattccaa atgtgtccca acagtcatta ccgaggttgt tacttcgaaa    2820
ggcacgcctt ctaatggaca ttcttctcaa actctacaaa cggaggcagt agaggtgaca    2880
ttgtcatccc atcaaaccgt aactatgagt accgaagtat gttctaattc gatttgcaca    2940
ccgactgtta ttacatctgt gcaaatgaga agtactcctt ttccatactt aacttcttca    3000
acgtcaagtt cctcttttagc ctccaccaaa aaaagttcct tagaagcctc ctcagaaatg    3060 tccaccttttt ctgtcagtac gcaaagtttg cctttggcat tcacaagttc agaaaaacgc    3120
tccaccacat ctgtctctca atggtcaaat accgttttaa ctaatacaat aatgtcctct    3180
tcttctaatg tcatatcaac aaatgaaaag cccagtagta ctacctctcc atacaacttc    3240
tcttcggggt actcttttacc ttcttcttct acaccttccc aatattcact atctacagct    3300
actacaacaa tcaacggaat caaaactgtg tacacaactt ggtgtccatt ggcagaaaaa    3360
tctactgtag ctgcttcttc tcaatcttcc cgcagtgttg acaggtttgt ttcgtcgtca    3420
aaaccatcct catctttatc tcagacctct attcaatata cattatctac tgctaccacc    3480
accataagtg gttttgaagac tgtatacacg acttggtgtc cattaacaag taaatcgact    3540
ttaggtgcta ctactcaaac ttcctcgaca gccaaagtta gaattacttc cgcttcatct    3600
gcaacatcta cttctatttc tttgagcact tcaacagaat cagaatcttc atctggatat    3660
ttgtcgaaag gagtatgctc aggtactgaa tgtacgcaag atgtgccaac acaatcatcc    3720
tcacctgctt caacgttagc atattccccc tctgttttcta catcatcatc atcatcattc    3780
tcaacaacaa ctgcatcaac actaacgtca acacacacct ctgtcccgtt attaccatca    3840
tctagctcta tatcagcatc ttcgccatca tcaacttcgt tgttatccac ttctttacca    3900
tctcccgctt ttacgtcatc aacacttcca acagcaacag cagtatcttc ctccactttc    3960
atagcgtctt ctctaccatt gtcctctaaa tcatcattgt cgttatcgcc agtctcgtcg    4020 tctatttttga tgtctcagtt ttcatcatca tcatcatcat catcatcatt ggcatcgttg    4080
ccatctcttt ctatatcacc aactgttgac actgtttctg ttctacaacc aactacttcc    4140
atcgcaacac taacttgcac agactcacaa tgccaacagg aggtatccac tatctgtaat    4200
ggatccaact gtgacgatgt gacttcaact gccactactc ctccatctac ggttactgat    4260
actatgacat gtactggatc tgagtgccag aaaaccacat ctagcagctg tgatggttac    4320
tcgtgtaaag tatccgaaac gtataaatca agcgctacaa tatctgcatg tagtggagaa    4380
ggatgccaag cttccgctac aagtgagcta aattctcaat acgtcacgat gacgtctgtc    4440
attaccccaa gtgccataac aacaacatca gtggaagtgc attcaactga atccactata    4500
tcaattacta cagtgaagcc agttacatat acatccagtg atactaatgg agaactgata    4560
accataacaa gttccagcca aactgtaatt ccatcagtaa cgacgataat aacgagaaca    4620
aaagtggcca taacttcagc accaaagcca acaactacga cctatgtcga gcaacgactt    4680
tcctccagtg ggattgctac ttcttttgtt gctgctgcat cctcaacttg gattactaca    4740
```

```
cccattgtca gtacgtatgc tggttcggcg tcaaaatttc tctgtagtaa gttctttatg      4800
ataatggtaa tggtgatcaa cttcatttaa                                       4830
```

<210> SEQ ID NO 26
<211> LENGTH: 152
<212> TYPE: PRT
<213> ORGANISM: Gallus gallus

<400> SEQUENCE: 26

```
Met Val His Ala Thr Ser Pro Leu Leu Leu Leu Leu Leu Ser Leu
1               5                   10                  15

Ala Leu Val Ala Pro Gly Leu Ser Ala Arg Lys Cys Ser Leu Thr Gly
            20                  25                  30

Lys Trp Asp Asn Asp Leu Gly Ser Asn Met Thr Ile Gly Ala Val Asn
        35                  40                  45

Ser Lys Gly Glu Phe Thr Gly Thr Tyr Thr Thr Ala Val Thr Ala Thr
    50                  55                  60

Ser Asn Glu Ile Lys Glu Ser Pro Leu His Gly Thr Gln Asn Thr Ile
65                  70                  75                  80

Asn Lys Arg Thr Gln Pro Thr Phe Gly Phe Thr Val Asn Trp Lys Phe
                85                  90                  95

Ser Glu Ser Thr Thr Val Phe Thr Gly Gln Cys Phe Ile Asp Arg Asn
            100                 105                 110

Gly Lys Glu Val Leu Lys Thr Met Trp Leu Leu Arg Ser Ser Val Asn
        115                 120                 125

Asp Ile Gly Asp Asp Trp Lys Ala Thr Arg Val Gly Ile Asn Ile Phe
    130                 135                 140

Thr Arg Leu Arg Thr Gln Lys Glu
145                 150
```

<210> SEQ ID NO 27
<211> LENGTH: 183
<212> TYPE: PRT
<213> ORGANISM: Streptomyces avidinii

<400> SEQUENCE: 27

```
Met Arg Lys Ile Val Val Ala Ala Ile Ala Val Ser Leu Thr Thr Val
1               5                   10                  15

Ser Ile Thr Ala Ser Ala Ser Ala Asp Pro Ser Lys Asp Ser Lys Ala
            20                  25                  30

Gln Val Ser Ala Ala Glu Ala Gly Ile Thr Gly Thr Trp Tyr Asn Gln
        35                  40                  45

Leu Gly Ser Thr Phe Ile Val Thr Ala Gly Ala Asp Gly Ala Leu Thr
    50                  55                  60

Gly Thr Tyr Glu Ser Ala Val Gly Asn Ala Glu Ser Arg Tyr Val Leu
65                  70                  75                  80

Thr Gly Arg Tyr Asp Ser Ala Pro Ala Thr Asp Gly Ser Gly Thr Ala
                85                  90                  95

Leu Gly Trp Thr Val Ala Trp Lys Asn Asn Tyr Arg Asn Ala His Ser
            100                 105                 110

Ala Thr Thr Trp Ser Gly Gln Tyr Val Gly Gly Ala Glu Ala Arg Ile
        115                 120                 125

Asn Thr Gln Trp Leu Leu Thr Ser Gly Thr Thr Glu Ala Asn Ala Trp
    130                 135                 140

Lys Ser Thr Leu Val Gly His Asp Thr Phe Thr Lys Val Lys Pro Ser
145                 150                 155                 160
```

```
Ala Ala Ser Ile Asp Ala Ala Lys Lys Ala Gly Val Asn Asn Gly Asn
            165                 170                 175

Pro Leu Asp Ala Val Gln Gln
            180

<210> SEQ ID NO 28
<211> LENGTH: 459
<212> TYPE: DNA
<213> ORGANISM: Gallus gallus

<400> SEQUENCE: 28
atggtgcacg caacctcccc gctgctgctg ctgctgctgc tcagcctggc tctggtggct      60
cccggcctct ctgccagaaa gtgctcgctg actgggaaat ggaccaacga tctgggctcc     120
aacatgacca tcgggctgt gaacagcaga ggtgaattca caggcaccta catcacagcc      180
gtaacagcca catcaaatga gatcaaagag tcaccactgc atgggacaca aacaccatc      240 aacaaggaga cccagcccac ctttggcttc accgtcaatt ggaagttttc agagtccacc     300
actgtcttca cgggccagtg cttcatagac aggaatggga aggaggtcct gaagaccatg     360
tggctgctgc ggtcaagtgt taatgacatt ggtgatgact ggaaagctac cagggtcggc     420
atcaacatct tcactcgcct gcgcacacag aaggagtga                           459

<210> SEQ ID NO 29
<211> LENGTH: 552
<212> TYPE: DNA
<213> ORGANISM: Streptomyces avidinii

<400> SEQUENCE: 29
atgcgcaaga tcgtcgttgc agccatcgcc gtttccctga ccacggtctc gattacggcc      60
agcgcttcgg cagacccctc caaggactcg aaggcccagg tctcggccgc cgaggccggc     120
atcaccggca cctggtacaa ccagctcggc tcgaccttca tcgtgaccgc gggcgccgac     180
ggcgccctga ccggaaccta cgagtcggcc gtcggcaacg ccgagagccg ctacgtcctg     240
accggtcgtt acgacagcgc cccggccacc gacggcagcg gcaccgccct cggttggacg     300
gtggcctgga agaataacta ccgcaacgcc cactccgcga ccacgtggag cggccagtac     360
gtcggcggcg ccgaggcgag gatcaacacc cagtggctgc tgacctccgg caccaccgag     420
gccaacgcct ggaagtccac gctggtcggc cacgacacct tcaccaaggt gaagccgtcc     480
gccgcctcca tcgacgcggc gaagaaggcc ggcgtcaaca acggcaaccc gctcgacgcc     540
gttcagcagt ag                                                        552

<210> SEQ ID NO 30
<211> LENGTH: 33
<212> TYPE: DNA
<213> ORGANISM: artificial sequence
<220> FEATURE:
<223> OTHER INFORMATION: forward avidin PCR primer

<400> SEQUENCE: 30
cgaactggat cctctcccag aaagtgctcg ctg                                  33

<210> SEQ ID NO 31
<211> LENGTH: 30
<212> TYPE: DNA
<213> ORGANISM: artificial sequence
<220> FEATURE:
<223> OTHER INFORMATION: reverse avidin PCR primer
```

```
<400> SEQUENCE: 31
cggatcctcg agtcactcct tctgtgtgcg                                    30

<210> SEQ ID NO 32
<211> LENGTH: 27
<212> TYPE: DNA
<213> ORGANISM: artificial sequence
<220> FEATURE:
<223> OTHER INFORMATION: forward streptavidin primer

<400> SEQUENCE: 32
gcgaattcag acccctccaa ggactcg                                       27

<210> SEQ ID NO 33
<211> LENGTH: 26
<212> TYPE: DNA
<213> ORGANISM: artificial sequence
<220> FEATURE:
<223> OTHER INFORMATION: streptavidin primer reverse

<400> SEQUENCE: 33
gcaagcttct actgctgaac ggcgtc                                        26

<210> SEQ ID NO 34
<211> LENGTH: 28
<212> TYPE: DNA
<213> ORGANISM: artificial sequence
<220> FEATURE:
<223> OTHER INFORMATION: truncated fadL forward primer

<400> SEQUENCE: 34
ggaattcatg gtcatgagcc agaaaacc                                      28

<210> SEQ ID NO 35
<211> LENGTH: 26
<212> TYPE: DNA
<213> ORGANISM: artificial sequence
<220> FEATURE:
<223> OTHER INFORMATION: truncated fadL primer reverse

<400> SEQUENCE: 35
gctctagaac gattctgtgc aggaac                                        26

<210> SEQ ID NO 36
<211> LENGTH: 26
<212> TYPE: DNA
<213> ORGANISM: artificial sequence
<220> FEATURE:
<223> OTHER INFORMATION: streptavidin forward pct primer

<400> SEQUENCE: 36
gctctagaga cccctccaag gactcg                                        26

<210> SEQ ID NO 37
<211> LENGTH: 5769
<212> TYPE: DNA
<213> ORGANISM: artificial sequence
<220> FEATURE:
<223> OTHER INFORMATION: fusion protein

<400> SEQUENCE: 37
gtttgacagc ttatcatcga ctgcacggtg caccaatgct tctggcgtca ggcagccatc    60
ggaagctgtg gtatggctgt gcaggtcgta atcactgcta taattcgtgt cgctcaaggc   120
gcactcccgt tctggataat gttttttgcg ccgacatcat aacggttctg gcaaatattc   180
```

```
tgaaatgagc tgttgacaat taatcatccg gctcgtataa tgtgtggaat tgtgagcgga      240
taacaatttc acacaggaaa cagaccatgg aattcatggt catgagccag aaaaccctgt      300
ttacaaagtc tgctctcgca gtcgcagtgg cacttatctc cacccaggcc tggtcggcag      360
gctttcagtt aaacgaattt tcttcctctg gcctgggccg ggcttattca ggggaaggcg      420
caattgccga tgatgcaggt aacgtcagcc gtaaccccgc attgattact atgtttgacc      480
gcccgacatt ttctgcgggt gcggtttata ttgacccgga tgtaaatatc agcggaacgt      540
ctccatctgg tcgtagcctg aaagccgata acatcgcgcc tacggcatgg gttccgaaca      600
tgcactttgt tgcaccgatt aacgaccaat ttggttgggg cgcttctatt acctctaact      660
atggtctggc tacagagttt aacgatactt atgcaggcgg ctctgtcggg ggtacaaccg      720
accttgaaac catgaacctg aacttaagcg gtgcgtatcg cttaaataat gcatggagct      780
ttggtcttgg tttcaacgcc gtctacgctc gcgcgaaaat tgaacgtttc gcaggcgatc      840
tggggcagtt ggttgctggc caaattatgc aatctcctgc tggccaaact cagcaagggc      900
aagcattggc agctaccgcc aacggtattg acagtaatac caaaatcgct catctgaacg      960
gtaaccagtg gggctttggc tggaacgccg gaatcctgta tgaactggat aaaaataacc     1020
gctatgcact gacctaccgt tctgaagtga aaattgactt caaaggtaac tacagcagcg     1080
atcttaatcg tgcgttttaat aactacggtt tgccaattcc taccgcgaca ggtgcgcaa     1140 cgcaatcggg ttatctgacg ctgaacctgc ctgaaatgtg ggaagtgtca ggttataacc     1200
gtgttgatcc acagtgggcg attcactata gcctggctta caccagctgg agtcagttcc     1260
agcagctgaa agcgacctca accagtggcg acacgctgtt ccagaaacat gaaggcttta     1320
aagatgctta ccgcatcgcg ttgggtacca cttattacta cgatgataac tggaccttcc     1380
gtaccggtat cgcctttgat gacagcccag ttcctgcaca gaatcgttct agagacccct     1440
ccaaggactc gaaggcccag gtctcggccg ccgaggccgg catcaccggc acctggtaca     1500
accagctcgg ctcgaccttc atcgtgaccg cgggcgccga cggcgccctg accggaacct     1560
acgagtcggc cgtcggcaac gccgagagcc gctacgtcct gaccggtcgt tacgacagcg     1620
cccccggcca cgacggcagc ggcaccgccc tcggttggac ggtggcctgg aagaataact     1680
accgcaacgc ccactccgcg accacgtgga gcggccagta cgtcggcggc gccgaggcga     1740
ggatcaacac ccagtggctg ctgacctccg gcaccaccga ggccaacgcc tggaagtcca     1800
cgctggtcgg ccacgacacc ttcaccaagg tgaagccgtc cgccgcctcc atcgacgcgg     1860
cgaagaaggc cggcgtcaac aacggcaacc cgctcgacgc cgttcagcag tagaagcttg     1920
gctgttttgg cggatgagag aagattttca gcctgataca gattaaatca gaacgcagaa     1980
gcggtctgat aaaacagaat ttgcctggcg gcagtagcgc ggtggtccca cctgacccca     2040
tgccgaactc agaagtgaaa cgccgtagcg ccgatggtag tgtgggtct ccccatgcga     2100 gagtagggaa ctgccaggca tcaaataaaa cgaaaggctc agtcgaaaga ctgggccttt     2160
cgttttatct gttgtttgtc ggtgaacgct ctcctgagta ggacaaatcc gccgggagcg     2220
gatttgaacg ttgcgaagca acggcccgga gggtggcggg caggacgccc gccataaact     2280
gccaggcatc aaattaagca gaaggccatc ctgacggatg ccttttttgc gtttctacaa     2340 actcttttg tttattttc taaatacatt caaatatgta tccgctcatg agacaataac     2400
cctgataaat gcttcaataa tattgaaaaa ggaagagtat gagtattcaa catttccgtg     2460
tcgcccttat tccctttttt gcggcatttt gccttcctgt ttttgctcac ccagaaacgc     2520
tggtgaaagt aaaagatgct gaagatcagt tgggtgcacg agtgggttac atcgaactgg     2580
```

-continued

```
atctcaacag cggtaagatc cttgagagtt ttcgccccga agaacgtttt ccaatgatga    2640
gcacttttaa agttctgcta tgtggcgcgg tattatcccg tgttgacgcc gggcaagagc    2700
aactcggtcg ccgcatacac tattctcaga atgacttggt tgagtactca ccagtcacag    2760
aaaagcatct tacggatggc atgacagtaa gagaattatg cagtgctgcc ataaccatga    2820
gtgataacac tgcggccaac ttacttctga caacgatcgg aggaccgaag gagctaaccg    2880
cttttttgca caacatgggg gatcatgtaa ctcgccttga tcgttgggaa ccggagctga    2940
atgaagccat accaaacgac gagcgtgaca ccacgatgcc tacagcaatg gcaacaacgt    3000
tgcgcaaact attaactggc gaactactta ctctagcttc ccggcaacaa ttaatagact    3060
ggatggaggc ggataaagtt gcaggaccac ttctgcgctc ggcccttccg gctggctggt    3120
ttattgctga taaatctgga gccggtgagc gtgggtctcg cggtatcatt gcagcactgg    3180
ggccagatgg taagccctcc cgtatcgtag ttatctacac gacggggagt caggcaacta    3240
tggatgaacg aaatagacag atcgctgaga taggtgcctc actgattaag cattggtaac    3300
tgtcagacca agtttactca tatatacttt agattgattt aaaacttcat ttttaattta    3360
aaaggatcta ggtgaagatc ctttttgata atctcatgac caaaatccct taacgtgagt    3420
tttcgttcca ctgagcgtca gaccccgtag aaaagatcaa aggatcttct tgagatcctt    3480
tttttctgcg cgtaatctgc tgcttgcaaa caaaaaaacc accgctacca gcggtggttt    3540
gtttgccgga tcaagagcta ccaactcttt ttccgaaggt aactggcttc agcagagcgc    3600
agataccaaa tactgtcctt ctagtgtagc cgtagttagg ccaccacttc aagaactctg    3660
tagcaccgcc tacatacctc gctctgctaa tcctgttacc agtggctgct gccagtggcg    3720
ataagtcgtg tcttaccggg ttggactcaa gacgatagtt accggataag gcgcagcggt    3780
cgggctgaac ggggggttcg tgcacacagc ccagcttgga gcgaacgacc tacaccgaac    3840
tgagatacct acagcgtgag ctatgagaaa gcgccacgct tcccgaaggg agaaaggcgg    3900
acaggtatcc ggtaagcggc agggtcggaa caggagagcg cacgagggag cttccagggg    3960
gaaacgcctg gtatctttat agtcctgtcg ggtttcgcca cctctgactt gagcgtcgat    4020
ttttgtgatg ctcgtcaggg gggcggagcc tatggaaaaa cgccagcaac gcggcctttt    4080
tacggttcct ggccttttgc tggccttttg ctcacatgtt ctttcctgcg ttatcccctg    4140
attctgtgga taaccgtatt accgcctttg agtgagctga taccgctcgc cgcagccgaa    4200
cgaccgagcg cagcgagtca gtgagcgagg aagcggaaga gcgcctgatg cggtattttc    4260
tccttacgca tctgtgcggt atttcacacc gcatatggtg cactctcagt acaatctgct    4320
ctgatgccgc atagttaagc cagtatacac tccgctatcg ctacgtgact gggtcatggc    4380
tgcgccccga cacccgccaa cacccgctga cgcgccctga cgggcttgtc tgctcccggc    4440
atccgcttac agacaagctg tgaccgtctc cgggagctgc atgtgtcaga ggttttcacc    4500
gtcatcaccg aaacgcgcga ggcagcagat caattcgcgc gcgaaggcga agcggcatgc    4560
atttacgttg acaccatcga atggtgcaaa acctttcgcg gtatggcatg atagcgcccg    4620
gaagagagtc aattcagggt ggtgaatgtg aaaccagtaa cgttatacga tgtcgcagag    4680
tatgccggtg tctcttatca gaccgtttcc cgcgtggtga accaggccag ccacgtttct    4740
gcgaaaacgc gggaaaaagt ggaagcggcg atggcggagc tgaattacat tcccaaccgc    4800
gtggcacaac aactggcggg caaacagtcg ttgctgattg gcgttgccac ctccagtctg    4860
gccctgcacg cgccgtcgca aattgtcgcg gcgattaaat ctcgcgccga tcaactgggt    4920
gccagcgtgg tggtgtcgat ggtagaacga agcggcgtcg aagcctgtaa agcggcggtg    4980
```

```
cacaatcttc tcgcgcaacg cgtcagtggg ctgatcatta actatccgct ggatgaccag    5040
gatgccattg ctgtggaagc tgcctgcact aatgttccgg cgttatttct tgatgtctct    5100
gaccagacac ccatcaacag tattattttc tcccatgaag acggtacgcg actgggcgtg    5160
gagcatctgg tcgcattggg tcaccagcaa atcgcgctgt tagcgggccc attaagttct    5220
gtctcggcgc gtctgcgtct ggctggctgg cataaatatc tcactcgcaa tcaaattcag    5280
ccgatagcgg aacgggaagg cgactggagt gccatgtccg gttttcaaca aaccatgcaa    5340
atgctgaatg agggcatcgt tcccactgcg atgctggttg ccaacgatca gatgcgcctg    5400
ggcgcaatgc gcgccattac cgagtccggg ctgcgcgttg gtgcggatat ctcggtagtg    5460
ggatacgacg ataccgaaga cagctcatgt tatatcccgc cgtcaaccac catcaaacag    5520
gattttcgcc tgctggggca aaccagcgtg accgcttgc tgcaactctc tcagggccag    5580
gcggtgaagg gcaatcagct gttgcccgtc tcactggtga aagaaaaac caccctggcg    5640 cccaatacgc aaaccgcctc tccccgcgcg ttggccgatt cattaatgca gctggcacga    5700
caggtttccc gactggaaag cgggcagtga gcgcaacgca attaatgtga gttagcgcga    5760
attgatctg                                                              5769

<210> SEQ ID NO 38
<211> LENGTH: 1017
<212> TYPE: DNA
<213> ORGANISM: Saccharomyces cerevisiae

<400> SEQUENCE: 38
atgaaattat caactgtcct attatctgcc ggtttagcct cgactacttt ggcccaattt      60
tccaacagta catctgcttc ttccaccgat gtcacttcct cctcttccat ctccacttcc     120
tctggctcag taactatcac atcttctgaa gctccagaat ccgacaacgg taccagcaca     180
gctgcaccaa ctgaaaccc aacagaggct ccaaccactg ctatcccaac taacggtacc     240
tctactgaag ctccaaccac tgctatccca actaacggta cctctactga agctccaact     300
gatactacta ctgaagctcc aaccaccgct cttccaacta acggtacttc tactgaagct     360
ccaactgata ctactactga agctccaacc accggtcttc caaccaacgg taccacttca     420
gctttcccac caactacatc tttgccacca agcaacacta ccaccactcc tccttacaac     480
ccatctactg actacaccac tgactacact gtagtcactg aatatactac ttactgtcca     540
gaaccaacca ctttcaccac aaacggtaag acttacaccg tcactgaacc aaccacattg     600
actatcactg actgtccatg caccattgaa agccaacaa ccacatcaac caccgaatac     660
actgtagtca ctgagtacac tacttactgt ccagaaccaa ccactttcac cacaaacggt     720
aagacttaca ccgtcactga accaaccact ttgactatca ctgactgtcc atgtactatt     780 gaaagagcg aagcccctga gtcttctgtc ccagttaccg aatctaaggg cactaccacc     840
aaagaaacag tgttactac aaacaaacc acagccaacc aagtctaac cgtctcccaca    900 gtcgtcccag tttcatcctc tgcttcttct cattccgttg tcatcaacag taacggtgct     960
aacgtcgtcg ttccaggtgc tttaggtttg gctggtgttg ctatgttatt cttataa      1017

<210> SEQ ID NO 39
<211> LENGTH: 1167
<212> TYPE: DNA
<213> ORGANISM: Escherichia coli
```

-continued

<400> SEQUENCE: 39

```
ggaattcatg gtcatgagcc agaaaaccct gtttacaaag tctgctctcg cagtcgcagt      60
ggcacttatc tccacccagg cctggtcggc aggctttcag ttaaacgaat tttcttcctc     120
tggcctgggc cgggcttatt caggggaagg cgcaattgcc gatgatgcag gtaacgtcag     180
ccgtaacccc gcattgatta ctatgtttga ccgcccgaca ttttctgcgg gtgcggttta     240
tattgacccg gatgtaaata tcagcggaac gtctccatct ggtcgtagcc tgaaagccga     300
taacatcgcg cctacggcat gggttccgaa catgcacttt gttgcaccga ttaacgacca     360
atttggttgg ggcgcttcta ttacctctaa ctatggtctg gctacagagt ttaacgatac     420
ttatgcaggc ggctctgtcg ggggtacaac cgaccttgaa accatgaacc tgaacttaag     480
cggtgcgtat cgcttaaata atgcatggag ctttggtctt ggtttcaacg ccgtctacgc     540
tcgcgcgaaa attgaacgtt tcgcaggcga tctggggcag ttggttgctg ccaaattat      600
gcaatctcct gctggccaaa ctcagcaagg caagcattg gcagctaccg caacggtat       660
tgacagtaat accaaaatcg ctcatctgaa cggtaaccag tggggctttg gctggaacgc     720
cggaatcctg tatgaactgg ataaaaataa ccgctatgca ctgacctacc gttctgaagt     780
gaaaattgac ttcaaaggta actacagcag cgatcttaat cgtgcgttta ataactacgg     840
tttgccaatt cctaccgcga caggtggcgc aacgcaatcg ggttatctga cgctgaacct     900
gcctgaaatg tgggaagtgt caggttataa ccgtgttgat ccacagtggg cgattcacta     960
tagcctggct tacaccagct ggagtcagtt ccagcagctg aaagcgacct caaccagtgg    1020
cgacacgctg ttccagaaac atgaaggctt taaagatgct taccgcatcg cgttgggtac    1080
cacttattac tacgatgata actggacctt ccgtaccggt atcgcctttg atgacagccc    1140
agttcctgca cagaatcgtt ctagagc                                        1167
```

<210> SEQ ID NO 40
<211> LENGTH: 386
<212> TYPE: PRT
<213> ORGANISM: Escherichia coli

<400> SEQUENCE: 40

```
Met Val Met Ser Gln Lys Thr Leu Phe Thr Lys Ser Ala Leu Ala Val
1               5                   10                  15

Ala Val Ala Leu Ile Ser Thr Gln Ala Trp Ser Ala Gly Phe Gln Leu
            20                  25                  30

Asn Glu Phe Ser Ser Gly Leu Gly Arg Ala Tyr Ser Gly Glu Gly
        35                  40                  45

Ala Ile Ala Asp Asp Ala Gly Asn Val Ser Arg Asn Pro Ala Leu Ile
    50                  55                  60

Thr Met Phe Asp Arg Pro Thr Phe Ser Ala Gly Ala Val Tyr Ile Asp
65                  70                  75                  80

Pro Asp Val Asn Ile Ser Gly Thr Ser Pro Ser Gly Arg Ser Leu Lys
                85                  90                  95

Ala Asp Asn Ile Ala Pro Thr Ala Trp Val Pro Asn Met His Phe Val
            100                 105                 110

Ala Pro Ile Asn Asp Gln Phe Gly Trp Gly Ala Ser Ile Thr Ser Asn
        115                 120                 125

Tyr Gly Leu Ala Thr Glu Phe Asn Asp Thr Tyr Ala Gly Gly Ser Val
    130                 135                 140

Gly Gly Thr Thr Asp Leu Glu Thr Met Asn Leu Asn Leu Ser Gly Ala
145                 150                 155                 160
```

```
Tyr Arg Leu Asn Asn Ala Trp Ser Phe Gly Leu Gly Phe Asn Ala Val
            165                 170                 175

Tyr Ala Arg Ala Lys Ile Glu Arg Phe Ala Gly Asp Leu Gly Gln Leu
        180                 185                 190

Val Ala Gly Gln Ile Met Gln Ser Pro Ala Gly Gln Thr Gln Gln Gly
        195                 200                 205

Gln Ala Leu Ala Ala Thr Ala Asn Gly Ile Asp Ser Asn Thr Lys Ile
        210                 215                 220

Ala His Leu Asn Gly Asn Gln Trp Gly Phe Gly Trp Asn Ala Gly Ile
225                 230                 235                 240

Leu Tyr Glu Leu Asp Lys Asn Asn Arg Tyr Ala Leu Thr Tyr Arg Ser
                245                 250                 255

Glu Val Lys Ile Asp Phe Lys Gly Asn Tyr Ser Ser Asp Leu Asn Arg
            260                 265                 270

Ala Phe Asn Asn Tyr Gly Leu Pro Ile Pro Thr Ala Thr Gly Gly Ala
        275                 280                 285

Thr Gln Ser Gly Tyr Leu Thr Leu Asn Leu Pro Glu Met Trp Glu Val
        290                 295                 300

Ser Gly Tyr Asn Arg Val Asp Pro Gln Trp Ala Ile His Tyr Ser Leu
305                 310                 315                 320

Ala Tyr Thr Ser Trp Ser Gln Phe Gln Gln Leu Lys Ala Thr Ser Thr
                325                 330                 335

Ser Gly Asp Thr Leu Phe Gln Lys His Glu Gly Phe Lys Asp Ala Tyr
            340                 345                 350

Arg Ile Ala Leu Gly Thr Thr Tyr Tyr Tyr Asp Asp Asn Trp Thr Phe
        355                 360                 365

Arg Thr Gly Ile Ala Phe Asp Asp Ser Pro Val Pro Ala Gln Asn Arg
        370                 375                 380

Ser Arg
385

<210> SEQ ID NO 41
<211> LENGTH: 390
<212> TYPE: DNA
<213> ORGANISM: Gallus gallus

<400> SEQUENCE: 41
tctgccagaa agtgctcgct gactgggaaa tggaccaacg atctgggctc caacatgacc      60
atcggggctg tgaacagcag aggtgaattc acaggcacct acatcacagc cgtaacagcc     120
acatcaaatg agatcaaaga gtcaccactg catgggacac aaaacaccat caacaagagg     180
acccagccca cctttggctt caccgtcaat tggaagtttt cagagtccac cactgtcttc     240
acgggccagt gcttcataga caggaatggg aaggaggtcc tgaagaccat gtggctgctg     300
cggtcaagtg ttaatgacat tggtgatgac tggaaagcta ccagggtcgg catcaacatc     360
ttcactcgcc tgcgcacaca gaaggagtga                                      390

<210> SEQ ID NO 42
<211> LENGTH: 129
<212> TYPE: PRT
<213> ORGANISM: Gallus gallus

<400> SEQUENCE: 42

Ser Ala Arg Lys Cys Ser Leu Thr Gly Lys Trp Thr Asn Asp Leu Gly
1               5                   10                  15

Ser Asn Met Thr Ile Gly Ala Val Asn Ser Arg Gly Glu Phe Thr Gly
            20                  25                  30
```

Thr Tyr Ile Thr Ala Val Thr Ala Thr Ser Asn Glu Ile Lys Glu Ser
            35                  40                  45

Pro Leu His Gly Thr Gln Asn Thr Ile Asn Lys Arg Thr Gln Pro Thr
 50                  55                  60

Phe Gly Phe Thr Val Asn Trp Lys Phe Ser Glu Ser Thr Thr Val Phe
65                  70                  75                  80

Thr Gly Gln Cys Phe Ile Asp Arg Asn Gly Lys Glu Val Leu Lys Thr
                85                  90                  95

Met Trp Leu Leu Arg Ser Ser Val Asn Asp Ile Gly Asp Asp Trp Lys
            100                 105                 110

Ala Thr Arg Val Gly Ile Asn Ile Phe Thr Arg Leu Arg Thr Gln Lys
            115                 120                 125

Glu

<210> SEQ ID NO 43
<211> LENGTH: 480
<212> TYPE: DNA
<213> ORGANISM: Streptomyces avidinii

<400> SEQUENCE: 43
gacccctcca aggactcgaa ggcccaggtc tcggccgccg aggccggcat caccggcacc      60
tggtacaacc agctcggctc gaccttcatc gtgaccgcgg gcgccgacgg cgccctgacc     120
ggaacctacg agtcggccgt cggcaacgcc gagagccgct acgtcctgac cggtcgttac     180
gacagcgccc cggccaccga cggcagcggc accgccctcg gttggacggt ggcctggaag     240
aataactacc gcaacgccca ctccgcgacc acgtggagcg gccagtacgt cggcggcgcc     300
gaggcgagga tcaacaccca gtggctgctg acctccggca ccaccgaggc caacgcctgg     360
aagtccacgc tggtcggcca cgacaccttc accaaggtga agccgtccgc cgcctccatc     420
gacgcggcga agaaggccgg cgtcaacaac ggcaacccgc tcgacgccgt tcagcagtag     480

<210> SEQ ID NO 44
<211> LENGTH: 159
<212> TYPE: PRT
<213> ORGANISM: Streptomyces avidinii

<400> SEQUENCE: 44

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
            35                  40                  45

Asn Ala Glu Ser Arg Tyr Val Leu Thr Gly Arg Tyr Asp Ser Ala Pro
 50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
            115                 120                 125

-continued

```
Thr Phe Thr Lys Val Lys Pro Ser Ala Ala Ser Ile Asp Ala Ala Lys
        130             135             140

Lys Ala Gly Val Asn Asn Gly Asn Pro Leu Asp Ala Val Gln Gln
145             150                 155
```